United States Patent [19]

Gries et al.

[11] Patent Number: 5,403,572
[45] Date of Patent: Apr. 4, 1995

[54] MACROCYCLIC POLYAZA COMPOUNDS CONTAINING 5 OR 6 MEMBERED RINGS, PROCESS FOR PRODUCING THEM AND PHARMACEUTICAL MEDIA CONTAINING THEM

[75] Inventors: Heinz Gries; Bernd Radüchel; Johannes Platzek; Hanns-Joachim Weinmann; Wolf-Rüdiger Press; Ulrich Speck, all of Berlin, Germany

[73] Assignee: Schering Aktiengesellschaft, Berlin and Bergkamen, Germany

[21] Appl. No.: 213,431

[22] Filed: Mar. 15, 1994

Related U.S. Application Data

[60] Division of Ser. No. 907,929, Jul. 6, 1992, Pat. No. 5,334,371, which is a continuation-in-part of Ser. No. 381,887, Jul. 19, 1989, abandoned, and a continuation-in-part of Ser. No. 642,961, Jan. 18, 1991, abandoned.

[30] Foreign Application Priority Data

Jul. 20, 1988 [DE] Germany ................. 38 25 040.3
Jan. 18, 1990 [DE] Germany ................. 40 01 655.2

[51] Int. Cl.$^6$ ................. A61B 5/055; C07D 267/22
[52] U.S. Cl. ................. 424/9; 424/450; 540/465; 540/469; 540/472; 436/173
[58] Field of Search ................. 424/9, 450; 540/465, 540/469, 472; 128/653.4, 654; 436/173

[56] References Cited

U.S. PATENT DOCUMENTS

| | | | |
|---|---|---|---|
| 4,174,319 | 11/1979 | Kobuke | 260/239 BC |
| 4,639,365 | 1/1987 | Sherry | 424/9 |
| 4,647,447 | 3/1987 | Gries et al. | 424/9 |
| 4,678,667 | 7/1987 | Meares et al. | 424/85 |
| 4,920,195 | 4/1990 | Kankare et al. | 534/16 |
| 4,983,376 | 1/1991 | Sherry | 424/9 |
| 5,322,681 | 6/1994 | Klaveness | 424/9 |

FOREIGN PATENT DOCUMENTS

| | | |
|---|---|---|
| 2030472 | 5/1991 | Canada . |
| 0391766 | 10/1990 | European Pat. Off. . |
| 3825040 | 1/1990 | Germany . |
| 64/68363 | 3/1989 | Japan . |
| 91/10645 | 7/1991 | WIPO . |
| 91/10669 | 7/1991 | WIPO . |
| 93/11800 | 6/1993 | WIPO . |

OTHER PUBLICATIONS

Rakowski et al., Inorg. Chem., 14(5):1194–1200 (1975).
Nelson et al., Proc. R. Ir. Acad., 77B(19–47):523$\frac{2}{8}$532 (1977).
Stetter et al., Tetrahedron, 37:767–772 (1981).
Wu et al., Youji Huaxue, 6:437–439, 414 (1983).
Kimura et al., J. Am. Chem. Soc., 109:6212–6213 (1987).
Grant & Hackh's Chem. Dic., 5th ed., McGraw-Hill, p. 217 (1987).
Takalo et al., J. Heterocyclic Chem., 27:167–169 (1990).

*Primary Examiner*—Gary E. Hollinden
*Attorney, Agent, or Firm*—Millen, White, Zelano & Branigan

[57] ABSTRACT

The macrocyclic compounds of the following formula I and IV, defined herein and their salts with inorganic and/or organic bases, amino acids or amino acid amides are valuable diagnostic and therapeutic agents.

60 Claims, No Drawings

MACROCYCLIC POLYAZA COMPOUNDS CONTAINING 5 OR 6 MEMBERED RINGS, PROCESS FOR PRODUCING THEM AND PHARMACEUTICAL MEDIA CONTAINING THEM

RELATED APPLICATIONS

This application is a division of application Ser. No. 07/907,929, filed Jul. 6, 1992, U.S. Pat. No. 5,334,371 which is a continuation-in-part of Ser. No. 07/381,887, filed Jul. 19, 1989, abandoned and Ser. No. 07/642,961, filed Jan. 18, 1991, abandoned.

SUMMARY OF THE INVENTION

The invention relates to macrocyclic polyaza complexing agents, polyaza complexes and polyaza complex salts containing 5- or 6-membered rings, media containing these compounds, their use as diagnostic and therapeutic media as well as processes for the production of these compounds and media.

The invention further relates to macrocyclic tetraaza complexing compounds, complexes, and complex salts containing a six-membered ring, agents containing these compounds, their use as diagnostic aids and therapeutic agents, as well as processes for the preparation of these compounds and agents.

Metal complexes came into consideration as contrast media for radiology at the beginning of the 1950's. But the compounds used at that time were so toxic, that their use in human beings was unsuitable. It was, therefore, completely surprising that certain complex salts have proven to be sufficiently compatible, so that a routine use in humans for diagnostic purposes could be considered. The first recorded representative of this class of substances is the dimeglumine salt of Gd-DTPA [MAGNEVIST®, Schering, A.G.; gadolinium(III) complex of diethylenetriaminepentaacetic acid] described in European Patent Application Publication No. 71,564. This compound has proven its worth very well up to now as a contrast medium for nuclear magnetic resonance imaging or MRI in clinical testing on over 7,000 patients. Presently, the main focus for use is for diseases of the central nervous system.

A significant reason for the good compatibility of Gd-DTPA in clinical use is in the high efficacy in nuclear magnetic resonance imaging, particularly with many brain tumors. Because of its good effectiveness, Gd-DTPA, with 0.1 mmol/kg of body weight, can be administered in much lower doses than, for example, X-ray contrast media in many X-ray examinations.

As another representative of the complex salts, the meglumine salt of Gd-DOTA (gadolinium(III) complex of 1,4,7,10-tetraazacyclododecane-tetraacetic acid) described in German Patent Application No. 34 01 052 has also proven itself well for diagnostic purposes.

However, it is desirable to use chelates at even higher doses. This is especially the case for detection of certain diseases outside the central nervous system with the aid of nuclear spin tomography (nuclear magnetic resonance imaging or NMR diagnosis), but especially in the use of chelates as X-ray contrast media.

To keep the volume load of the body as small as possible, it is necessary to use highly concentrated chelate solutions. The chelates known until now are not very suitable for this purpose, especially because of their excessively high osmolality.

There is, therefore, a need for chelates which exhibit a lower osmolality than that of the previously known chelates. However, at the same time, the prerequisites for the use of these compounds on humans regarding the range between the effective dose and the toxic dose in animal testing (the therapeutic range), organ specificity, stability, contrast-enhancing effect, compatibility, as well as solubility of the chelate complex compounds must be fulfilled.

Thus, an object of the invention is to make available such compounds and media, as well as to provide a process that is as simple as possible for their production.

Upon further study of the specification and appended claims, further objects and advantages of this invention will become apparent to those skilled in the art.

The complex compounds according to the invention and the solutions prepared therefrom fulfill the requirements mentioned in a surprising manner. They have a decreased osmolality as well as a more favorable therapeutic range and/or stability and storage property of the chemical components of the solution and/or organ specificity and/or contrast-enhancing effect (e.g., relaxivity) and/or compatibility (e.g., decreased cardiovascular or allergy-like side effects) than the diagnostic agents in use until now.

Even without specific measures, their pharmacokinetics allows for an improvement in the diagnosis of numerous diseases. The complexes, for the most part, remain unchanged and are quickly excreted, so that particularly even if relatively toxic metal ions are used, no harmful effects are observed despite high doses.

The practical use of the new complexes and complexing agents is also made easier by their favorable chemical stability.

An additional significant advantage of the described complexes and complexing agents is their extraordinary chemical versatility. Besides the central atom, the characteristics can be adapted to the requirements for effectiveness, pharmacokinetics, compatibility, solubility, manageability, etc., by the choice of diverse substituents, the 5- or 6-membered ring in the macrocycle and/or the counterions. Thus, for example, a very desirable specificity of the compounds for diagnosis and therapy can be obtained for structures in the organism, for certain biochemical substances, for metabolic processes and/or for conditions of tissues or body fluids.

The macrocyclic compounds according to an aspect of the invention are characterized by general formula I

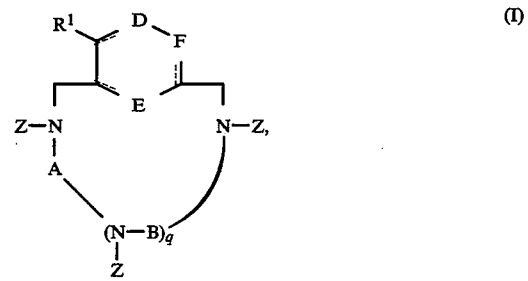

in which
stands for a single bond or double bond,
q stands for the numbers 0-5,
A and B, which are the same or different, each stands for a straight chain or branched alkylene group with 2 to 6 carbon atoms, D stands for a nitrogen atom, oxygen atom, the group =C=O, =NR² with R² meaning a hydrogen atom or a C₁-C₆ alkyl group, the group

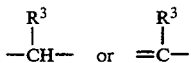

with R³ meaning a hydrogen atom or a halogen atom, a phenyl or a C₁-C₆ alkyl group, which alkyl optionally is substituted by one or more phenyl and/or hydroxy group(s), the radical OR⁵ wherein R⁵ stands for C₁-C₆ alkyl radical optionally substituted by 1 to 3 hydroxy groups, the substituent

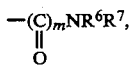

in which m stands for the numbers 0 and 1 and R⁶ and R⁷, independently of one another, stand for hydrogen atoms, the radical R⁵, phenyl or benzyl radicals optionally substituted by 1 to 3 hydroxy groups, or R⁶ and R⁷ together with the nitrogen atom stand for a saturated or unsaturated 5- or 6-membered ring optionally containing an additional nitrogen atom, oxygen atom, sulfur atom or a carbonyl group, which is optionally substituted by 1 to 3 radicals R⁵, or one of the substituents R⁶ or R⁷ stands for the radical

or substituent G, in which G stands for a second macrocycle of general formula II bonded by a direct bond, a bis(carbonylamino) group (—NH—CO—CO—NH—) or by a C₁-C₂₀-alkylene group, which optionally carries carbonyl (CO) groups or carbonylamino (—NH—CO—) groups or oxygen atoms on the ends and optionally contains one or more oxygen atom(s), hydroxymethylene (—CHOH—), Z—, acyl- or hydroxyacyl-substituted imino groups or one to two C—C double bonds and/or C—C triple bonds

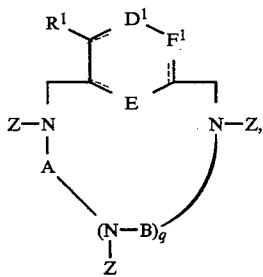

in which

D¹ has the same meaning as D, with the exception that D¹ does not contain the substituent G, or stands for the radical

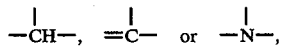

and

F¹ has the same meaning as F, with the exception that F¹ does not contain the substituent G, or stands for the radical

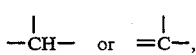

E stands for a nitrogen atom, sulfur atom, oxygen atom the

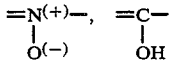

or NR⁴ group with R⁴ meaning a hydroxy group, R² or an optionally hydroxylated or carboxylated C₁-C₆ alkyl group, F stands for (—CHR⁸—)$_n$ or (=CR⁸—)$_n$ with n meaning the numbers 0 or 1 and R⁸ meaning R¹ or G, R¹ stands for a hydrogen atom or a halogen atom or a C₁-C₆ alkyl group, Z stands for a hydrogen atom or the group —CH₂COOY with Y meaning a hydrogen atom and/or a metal ion equivalent of an element with atomic numbers 21-29, 31, 32, 37-39, 42-44, 49 or 57-83, and its salts with inorganic and/or organic bases, amino acids or amino acid amides provided that at least two of substituents Z stand for the radical —CH₂COOY and the macrocyclic compound of general formula I contains not more than one radical G.

If n stands for the number 0 and the 5-membered ring thus formed is to be unsaturated, then the double bonds are located between positions 2,3 and 4,5 of the 5-membered ring.

Compounds of general formula I with Y meaning hydrogen are designated as complexing agents and with at least two of the substituents Y meaning a metal ion equivalent are designated as metal complexes.

According to a further aspect of the invention, the macrocyclic compounds are characterized by Formula IV:

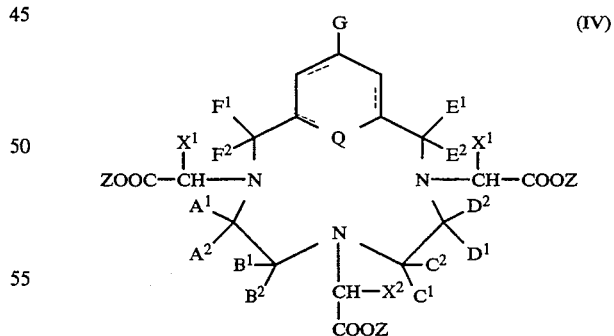

wherein is a single or double bond,

Q is a nitrogen atom or the residue NH,

X¹ is a hydrogen atom, a —(CH₂)$_n$—R¹ group or a —(CH₂)$_m$—(CH)$_n$—CH₂OH group wherein means the numbers 1 to 5, means the numbers 0 to 2, and R¹ means a hydrogen atom or a hydroxy group, X² means X¹ or a —(CH₂)$_n$—(O)$_l$—(CH₂)$_k$—(C₆H₄)$_q$—R² group wherein k means the numbers 0 to 4, l and q mean the number 0 or 1, and $R^2$ means a hydrogen atom, a $C_1$-$C_4$-alkoxy group, a functional group, or, bound via this functional group, a bio- or macromolecule, $A^1, A^2, B^1, B^2, C^1, C^2, D^1, D^2, E^1, E^2, F^1$ and $F^2$ mean in each case $X^2$, independently of one another, G means $R^2$ or a second macrocycle, bound via K, of general Formula V

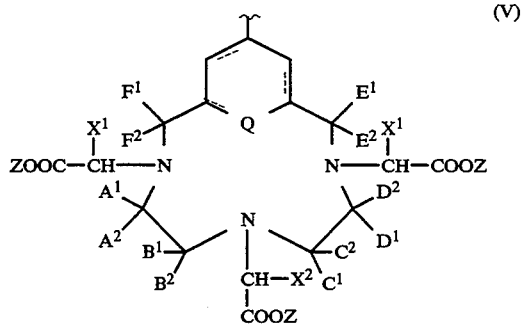

wherein

K means a direct bond, a bis(carbonylamino)group (—NH—CO—CO—NH—), or a $C_1$-$C_{14}$-alkylene group which optionally carries at the ends thereof carbonyl (>CO) or carbonylamino (—NH—CO—) groups or oxygen atoms, and which contains optionally one or several oxygen atom(s), hydroxymethylene (—CH—OH—), —CH($X^2$)COOZ, acyl-substituted or hydroxyacyl-substituted imino groups, or one to two C—C-double and/or C—C-triple bonds, Z is a hydrogen atom and/or a metal ion equivalent of an element of atomic numbers 21-29, 31, 32, 37-39, 42-44, 49 or 57-83, and their salts with inorganic and/or organic bases, amino acids or amino acid amides, with the provisos that the 12 ring substituents $A^1$ through $F^2$ stand for at least 8 hydrogen atoms, that $X^1$ and $X^2$ stand simultaneously for hydrogen only if at least one of the ring substituents $A^1$ through $F^2$ does not mean a hydrogen atom, and that the macrocycle of general Formula I contains no more than one bio- or macromolecule, and that, if desired, the remainder of the $CO_2H$ groups are each present as an ester or amide.

Preferred are tetraaza compounds of general Formula VI

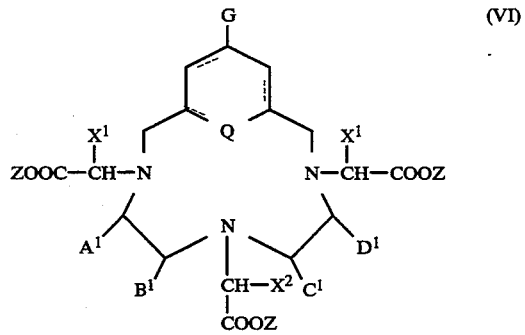

wherein is a single or double bond,

Q is a nitrogen atom or the residue NH, $X^1$ is a hydrogen atom, a —$(CH_2)_n$—$R^1$ group or a —$(CH_2)_m$—$(CH)_n$—$CH_2OH$ group wherein n means the numbers 1 to 5, m means the numbers 0 to 2, and $R^1$ means a hydrogen atom or a hydroxy group, $X^2$ means $X^1$ or a —$(CH_2)_n$—$(O)_l$—$(CH_2)_k$—$(C_6H_4)_q$—$R^2$ group wherein k means the numbers 0 to 4, l and q mean the number 0 or 1, and $R^2$ means a hydrogen atom, a $C_1$-$C_4$-alkoxy group, a functional group, or, bound via this functional group, a bio- or macromolecule, $A^1, B^1, C^1$ and $D^1$, independently of one another, mean $X^2$ in each case, G means $R^2$ or a second macrocycle, bound via K, of general Formula VII

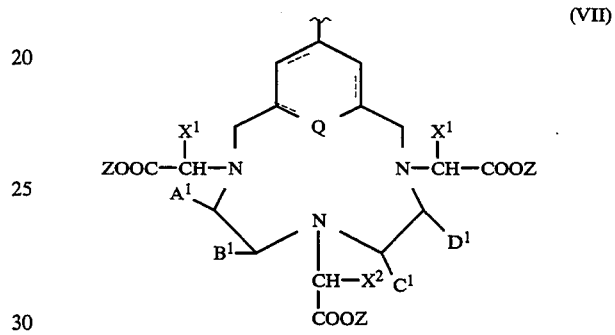

wherein

K means a direct bond, a bis(carbonylamino)group (—NH—CO—CO—NH—), or a $C_1$-$C_{14}$-alkylene group which optionally carries at the ends thereof carbonyl (>CO) or carbonylamino (—NH—CO—) groups or oxygen atoms, and which contains optionally one or several oxygen atom(s), hydroxymethylene (—CH—OH—), —CH($X^2$)—COOZ, acyl-substituted or hydroxyacyl-substituted imino groups or one to two C—C-double and/or C—C-triple bonds, Z is a hydrogen atom and/or a metal ion equivalent of an element of atomic numbers 21-29, 31, 32, 37-39, 42-44, 49 or 57-83, and their salts with inorganic and/or organic bases, amino acids or amino acid amides, with the provisos that $X^1$ and $X^2$ simultaneously mean hydrogen atoms only if at least one of the 4 ring substituents $A^1, B^1, C^1$ and $D^1$ does not stand for a hydrogen atom, and that, if desired, the remainder of the $CO_2H$ groups are each present as an ester or amide.

Compounds of general Formula IV, wherein Z means hydrogen, are denoted as complexing compounds, and with at least two of the substituents Z meaning a metal ion equivalent, are called metal complexes.

The element of the above-mentioned atomic number, which forms the central ion of the physiologically compatible complex salt, can also of course be radioactive for the intended purpose of use of the diagnostic agent according to the invention.

If the medium according to the invention is intended for use in NMR diagnosis, then the central ion of the complex salt must be paramagnetic. These are particularly the bivalent and trivalent ions of the elements with atomic numbers 21-29, 42, 44 and 58-70. Suitable ions are, e.g., the chromium(III), manganese(II), iron (II), cobalt (II), nickel (II), copper (II), praseodymium(III), neodymium(III), samarium(III) and ytterbium(III) ions. Because of their very strong magnetic moment, the gadolinium(III), terbium(III), dysprosium(III), holmium(III), erbium(III) and iron(III) ions are particularly preferred.

For the use of the media according to the invention in nuclear medicine, the central ion must be radioactive. Radioisotopes, for example, of the elements copper, cobalt, gallium, germanium, yttrium, strontium, technetium, indium, ytterbium, gadolinium, samarium and iridium are suitable.

If the medium according to the invention is intended for use in X-ray diagnosis, then the central ion should be derived from an element of a higher atomic number, to achieve sufficient absorption of the X-rays. It has been found that for this purpose diagnostic agents which contain a physiologically compatible complex salt with central ions of elements with atomic numbers of 21-29, 42, 44, 57-83 are suitable; these are, for example, the lanthanum(III) ion and the above-mentioned ions of the lanthanide series.

As alkyl substituents $R^1$, $R^2$, $R^3$ and $R^4$ of Formulae I and II, straight chain or branched hydrocarbons are suitable with up to 6, preferably up to 4 carbon atoms, which in the case of $R^3$ are optionally substituted by one or more, preferably 1 to 3, phenyl and/or hydroxy groups, in the case of $R^4$ optionally by one or more, preferably 1 to 3, hydroxy or carboxyl groups, and in the case of $R^5$ optionally by one or more, preferably 1 to 3, hydroxy groups.

Suitable optionally substituted alkyl groups are, for example, the methyl, hydroxymethyl, ethyl, 2-hydroxyethyl, 2-hydroxy-1-(hydroxymethyl)-ethyl, 1-(hydroxymethyl)-ethyl, propyl, isopropyl, 2- and 3-hydroxypropyl, 2,3-dihydroxypropyl, n-, sec.- and tert.-butyl, 2-, 3- and 4-hydroxybutyl, 2- and 3-hydroxy-isobutyl, pentyl, 2-, 3- and 4-hydroxy-2-methylbutyl, 2,3,4-trihydroxybutyl, 1,2,4-trihydroxybutyl, cyclopentyl, cyclohexyl, 2,3,4,5,6-pentahydroxyhexyl, benzyl, carboxymethyl and carboxyethyl.

The halogen atom contained in $R^1$ and $R^3$ of Formulae I and II can be, for example, fluorine, chlorine, bromine and iodine.

The heterocyclic 5- or 6-membered ring formed by $R^6$ and $R^7$ of formula I and II with inclusion of the nitrogen atom can be saturated, unsaturated and/or substituted and optionally can contain a nitrogen atom, oxygen atom, sulfur atom or a carbonyl group.

Suitable heterocycles include, for example, the pyrrolidinyl, piperidyl, pyrazolidinyl, pyrrolinyl, pyrazolinyl, piperazinyl, morpholinyl, imidazolidinyl, oxazolidinyl, thiazolidinyl, and pyrrolidonyl rings.

As alkylene groups A and B of Formula I and II, straight chain or branched chains with 2 to 6 carbon atoms, preferably the ethylene, methylethylene and propylene groups, are suitable.

The alkylene chain, on which the second macrocycle of Formula II is bonded, carries on the ends thereof optionally carbonyl (CO), carbonylamino (NH—CO) groups or oxygen atoms and contains 1-20 carbon atoms. It can be interrupted by one or more oxygen atoms(s), hydroxymethylene (—CHOH—), Z—, acyl- or hydroxyacyl-substituted imino groups or one to two C—C double bonds and/or C—C triple bonds. But, both macrocycles can also be connected by a direct bond. As optionally hydroxylated acyl groups in this case, acyl radicals with up to 10 carbon atoms are suitable. For example the acetyl, propionyl, butyryl, benzoyl and hydroxyacetyl radicals should be mentioned as species of optionally hydroxy-substituted hydrocarbonoyl of 1-10 carbon atoms.

The alkylene chain can be straight chain or branched chain, saturated or unsaturated and optionally interrupted as described. It can contain up to 4 oxygen atoms and/or up to 3 carboxymethylimino groups. Examples for the alkylene chain are:

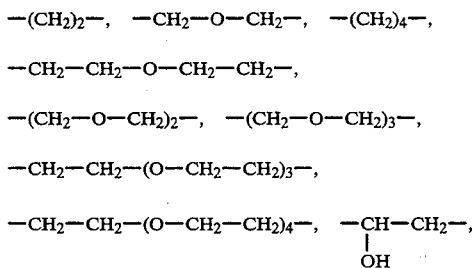

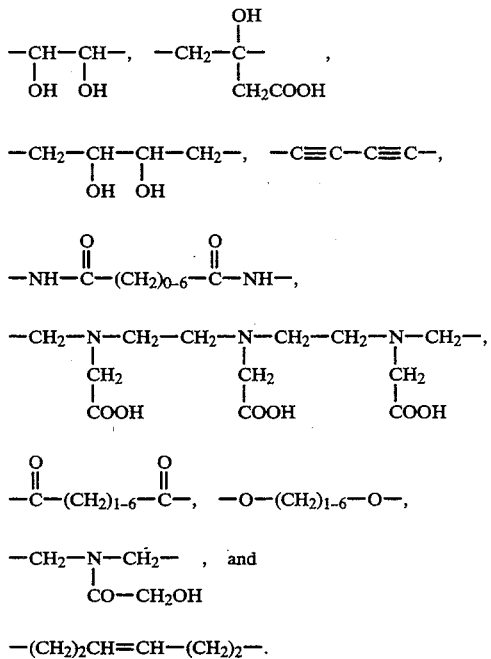

$-(CH_2)_2CH=CH-(CH_2)_2-$.

If not all acid hydrogen atoms are substituted by the central ion, one, several or all of the remaining hydrogen atom(s) can be replaced by cations of inorganic and/or organic bases or amino acids. Suitable inorganic cations are, e.g., the lithium ion, the potassium ion, the calcium ion, the magnesium ion and particularly the sodium ion. Suitable cations of organic bases are, among others, those of primary, secondary or tertiary amines, for example, such as ethanolamine, diethanolamine, morpholine, glucamine, N,N-dimethylglucamine and particularly N-methylglucamine. Suitable cations of amino acids are for example those of lysine, arginine and ornithine.

The production of the macrocyclic complexes of general formula I according to the invention takes place by compounds of general formula I' being alkylated in the manner known in the art

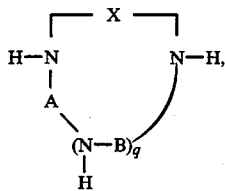

(I')

in which
X stands for

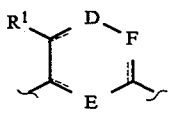

or for a 5- or 6-membered ring to be converted into the desired ring,
with a halogen compound of formula III

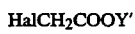

in which Hal stands for chlorine, bromine or iodine and Y' stands for a hydrogen atom or an acid protecting group,
and then, optionally after conversion of X into the desired 5- or 6-membered ring of the end product and also optionally after cleavage of the protecting groups Y', optionally the complexing agents of general formula I with Y meaning hydrogen thus obtained are reacted in the manner known in the art with at least one metal oxide or metal salt of an element with atomic numbers 21-29, 31, 32, 37-39, 42-44, 49 or 57-83 and then, if desired, acid hydrogen atoms still present are substituted by cations of inorganic and/or organic bases, amino acids or animo acid amides.

As acid protecting groups Y' lower alkyl, aryl and aralkyl groups, for example the methyl, ethyl, propyl, n-butyl, t-butyl, phenyl, benzyl, diphenylmethyl, triphenylmethyl, bis(p-nitrophenyl)methyl groups and trialkylsilyl groups are suitable.

The cleavage of protecting groups Y', which can be performed before or after conversion of X into the desired 5- or 6-membered ring of the end product, takes place according to the processes known to one skilled in the art, for example, by hydrolysis, hydrogenolysis, alkaline saponification of the esters with alkali in aqueous alcoholic solution at temperatures from 0° to 50° C. or, in the case of tertiary butyl esters, with the help of trifluoroacetic acid, for example.

The alkylization of educts I' with the halogen compounds of general formula III takes place in polar aprotic solvents such as, e.g., dimethylformamide, acetonitrile, dimethyl sulfoxide, aqueous tetrahydrofuran or hexamethylphosphoric triamide in the presence of an acid catcher, such as, for example, tertiary amine (e.g., triethylamine, trimethylamine or N,N-dimethylaminopyridine), 1,5-diazabicyclo [4.3.0] nonene-5 (DBN), 1,5-diazabicyclo [5.4.0] undecene-5 (DBU), alkali, alkaline earth carbonate, hydrogen carbonate or hydroxide (e.g., sodium, magnesium, calcium, barium, potassium carbonate, hydroxide and hydrogen carbonate) at temperatures between −10° C. and 120° C., preferably between 0° C. and 50° C.

The conversion of a precursor of the desired 5- or 6-membered ring obtained in the end product tales place according to the methods known to one skilled in the art, for example, the hydrogenation of, e.g., pyridine-[Advan. Catal. 14, 203 (1963)], pyrrol-[M. Freifelder, Practical Catalytic Hydrogenation, 577, Wiley-Interscience, New York-London-Sydney-Toronto 1971], furan-[U.S. Pat. No. 3,194,818], pryrimidine-[J. Med. Chem. 15, 291 (1972)], deoxygenation of nitroxide-[E. Klingsberg, The Chemistry of Heterocyclic Compounds, Volume 14, part 2, Interscience Publishers New York, p. 120 (1961)] rings, conversions and introduction of functional groups on the 5- or 6-membered ring, e.g., release of phenolic hydroxy groups [J. Org. Chem. 53, 5 (1988)], introduction of halogen substituents [E. Klingsberg, The Chemistry of Heterocyclic Compounds, Volume 14, Part 2, Interscience Publishers New York, p. 341 (1961)], Houben-Weyl, Methoden der organischen Chemic, Volume V/3, 651 (1962)], exchange of heteroatoms, e.g., conversion of a furan into a pyrrole (U.S. Pat. No. 2,478,456).

The functionalizing of 4-chloropyridine derivatives (e.g., azido exchange) in the phase transfer process with the use of 18-crown-6 or tetrabutyl ammonium bromide as a catalyst is described in "Phase Transfer Reactions" (Fluka Compendium, Vol. 2; Walter E. Keller, Georg Thieme Verlag, Stuttgart, New York).

The production of amides, i.e., of compounds of general formula I which contain the group —NR$^6$R$^7$, e.g., in which R$^5$ or R$^3$ stands for

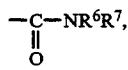

takes place by reaction of activated acid derivatives (e.g., mixed anhydride, acid chloride) with primary or second amines of the general formula

in which R$^6$ and R$^7$ have the meaning given above.

As suitable amines, the following should be mentioned as examples:
dimethylamine, diethylamine, di-n-propylamine, diisopropylamine, di-n-butylamine, diisobutylamine, di-sec.-butylamine, N-methylene-propylamine, dioctylamine, dicyclohexylamine, N-ethylcyclohexylamine, diisopropenylamine, benzylamine, aniline, 4-methoxyaniline, 4-dimethylaminoaniline, 3,5-dimethoxyaniline, morpholine, pyrrolidine, piperidine, N-methylpiperazine, N-ethylpiperazine, N-(2-hydroxyethyl)-piperazine, 2-(2-hydroxymethyl)-piperidine, 4-(2-hydroxyethyl)-piperidine, 2-hydroxymethylpiperidine, 4-hydroxymethyl-piperidine, 2-hydroxymethyl-pyrrolidine, 3-hydroxypiperidine, 4-hydroxypiperidine, 3-hydroxypiperidine, 4-hydroxypiperidine, 3-hydroxypyrrolidine, 4-piperidone, 3-pyrroline, 2,6-dimethylpiperidine, 2,6-dimethylmorpholine, pyrazoline, imidazoline, oxazolidine, thiazolidine, 2,3-dihydroxypropylamine, N-methyl-2,3-dihydroxypropylamine, 2-hydroxy-1-(hydroxymethyl)-ethylamine, N,N-bis(2-hydroxyethyl)amine, N-methyl-2,3,4,5,6-pentahydroxyhexylamine, 6-amino-2,2-dimethyl-1,3-dioxepin-5-ol, 2-hydroxyethylamine, 2-amino-1,3-propanediol, diethanoiamine and ethanolamine.

The polyhydroxyalkylamines can also be used advantageously in protected form for the reaction, for example, as O-acyl derivatives or as ketals. This is especially the case, when these derivatives are easier and cheaper to produce than the polyhydroxyalkylamines themselves. A typical example is 2-amino-1-(2,2-dimethyl-1,3-dioxylan-4-yl)-ethanol, the acetonide of 1-amino-2,3,4-trihydroxybutane, produced according to DE-OS 31 50 917.

The subsequent removal of the protecting groups can also be performed by, for example, treatment with an acidic ion exchanger in aqueous ethanol solution.

The synthesis of compounds with more than one ring takes place according to processes known in the literature, for example, by an addition/elimination reaction of an amine with a carbonyl compound (e.g., acid chloride, mixed anhydride, activated ester, aldehyde); of two amine substituted rings with a dicarbonyl compound (e.g., oxalyl chloride, glutaric dialdehyde); of two p-nitro substituted nitroxides with bisalcoholates [cf. E. Klingsberg, The Chemistry of Heterocyclic Compounds, Interscience Publishers New York, p. 514 (1961)]; of two rings, which each exhibit a nucleophilic group, with an alkylene compound carrying two leaving groups or in the case of terminal acetylenes by oxidative coupling (Cadiot Chodkiewicz in Viehe "Acetylenes" 597–647, Marcel Dekker, New York, 1969).

The chain connecting the rings can then be modified by consecutive reactions (hydrogenation, for example).

The synthesis of the educts of general formula I' to be alkylated takes place by cyclization of two reactants, of which one contains the substituent X, i.e., the desired 5 or 6-membered ring of the end product or a precursor to be converted into it.

The cyclization is performed according to methods known in the literature, (for example, Org. Synth. 58, 86 (1978), Makrocyclic Polyether Syntheses, Springer Verlag, Berlin, Heidelberg, New York 1982, Coord. Chem. Rev. 3, 3 (1968), Ann. Chem. 1976, 916, J. Org. Chem, 49, 110 [1984]): one of the two reactants carries on the end of the chain two leaving groups, the other contains two nitrogen atoms which displace these leaving groups in a nucleophilic manner. As an example there can be mentioned the reaction of terminal dichloro-, dibromo-, dimesyloxy-, ditosyloxy- or dialkoxycarbonylalkylene compounds containing the substituent X and optionally one to five nitrogen atom(s) with terminal diazaalkylene compounds, Optionally containing one to five additional nitrogen atoms in the alkylene chain. Instead, of this the substituent X can also be contained in the second reactant, i.e., the one with the terminal nucleophilic nitrogen atoms. The nitrogen atoms are optionally protected, for example as tosylates or trifluoroacetates, and are released before the subsequent alkylization reaction according to processes known in the literature (the tosylates, e.g., with mineral acids, alkali metals in liquid ammonia, hydrobromic acid and phenol, RedAl ®, lithium aluminum hydride, sodium amalgam, cf., e.g., Liebigs Ann. Chem. 1977, 1344, Tetrahedron Letters 1976, 3477; the trifluoroacetates, e.g., with mineral acids or ammonia in methanol, cf., e.g., Tetrahedron Letters 1967, 289).

For the production of macrocycles substituted in various manners on the nitrogen atoms (hydrogen or the $CH_2COOY$ group), these atoms can be provided in the educts with different protecting groups, e.g., with tosylate and benzyl groups. The latter are then also removed according to methods known in the literature, preferably by hydrogenation, e.g., EP-patent application 232751.

If diesters are used in the cyclization reaction, then the diketo compounds thus obtained must be reduced according to processes known to one skilled in the art, for example, with diborane.

Also, correspondingly, substituted terminal bisaldehydes with each of the respective desired terminal bisamines can be cyclized. The reduction of the Schiff's bases thus obtained takes place according to methods known in the literature, e.g., by catalytic hydrogenation [Helv. Chim. Acta 61, 1376 (1978)].

The production of the amines needed as initial substances for the cyclization takes place in a manner similar to methods known in the literature.

Starting from an N-protected amino acid, by reaction with a partially protected diamine (for example, according to the carbodiimide method), a triamine is obtained by cleavage of the protecting groups and diborane reduction.

The reaction of a diamine that can be obtained from amino acids (Eur. J. Med. Chem.-Chim. Ther. 21, 333 (1986)) with the double molar amount of an N-protected omega-amino acid yields a tetramine after suitable working up.

The desired diamines can also be produced by Gabriel reaction from, e.g., the corresponding tosylates or halides [cf., e.g., Inorg. Chem. 25, 4781 (1986)].

In both cases, the number of carbon atoms between the N-atoms can be determined by the kind of diamines or amino acids used as coupling partners.

The compounds of general formula I thus obtained with Y meaning a hydrogen atom represent complexing agents. They can be isolated and purified or can be converted without isolation into metal complexes of general formula I with at least two of the substituents Y meaning a metal ion equivalent.

Preferred groups for $X^1$ of Formulae IV, V, VI and VII that can be mentioned are $CH_2OH$, $CH_2CH_2OH$ and $CHOHCH_2OH$; and preferred groups for $X^2$, $A^1$, $B^1$, $C^1$ and/or $D^1$ are $CH_2OH$, $CH_2CH_2OH$, $CH_2OCH_2C_6H_5$, $CHOHCH_2OH$, $CH_2C_6H_4OCH_3$, $CH_2C_6H_5$, $CH_2C_6H_4O(CH_2)_3COOH$, $CH_2C_6H_4NCS$, wherein the remaining ring substituents $A^2$, $B^2$, $C^2$, $D^2$, $E^1$, $E^2$, $F^1$ and $F^2$ preferably each mean hydrogen.

The alkylene chain standing for K, to which the second macrocycle of formula V and VII, respectively, is linked, carries at the ends thereof optionally carbonyl (CO), carbonylamino (NH—CO) groups or oxygen atoms and contains 1–14 carbon atoms. This chain can be Interrupted by one or several oxygen atom(s), hydroxymethylene (—CHOH—), —CH($X^2$)COOZ, acyl- or hydroxyacyl-substituted imino groups or one to two C—C-double and/or C—C-triple bonds. The two macrocycles can, however, also be linked by a direct bond. Suitable optionally hydroxylated acyl groups are acyl residues or up to 10 carbon atoms. Examples in this connection are the acetyl, propionyl, butyryl, benzoyl and hydroxyacetyl residues.

The alkylene chain K can be straight- or branched-chain, saturated or unsaturated, and can be interrupted, if desired, as described above. This chain can contain up to 4 oxygen atoms and/or up to 3 carboxymethylimino groups.

Examples for the alkylene chain are:

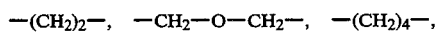

-continued

—CH₂—CH₂—O—CH₂—CH₂—,

—(CH₂—O—CH₂)₂—, —(CH₂—O—CH₂)₃—,

—CH₂—CH₂—(O—CH₂—CH₂)₃—,

—CH₂—CH₂—(O—CH₂—CH₂)₄—, —CH(OH)—CH(OH)—,

—CH₂—CH(OH)—CH(OH)—CH₂—, —C≡C—C≡C—,

—NH—C(=O)—(CH₂)₀₋₆—C(=O)—NH—

—CH₂—N(CHX²—COOZ)—CH₂—CH₂—N(CHX²—COOZ)—CH₂—CH₂—N(CHX²—COOZ)—CH₂—,

—C(=O)—(CH₂)₁₋₆—C(=O)—, —O—(CH₂)₁₋₆—O—,

—CH₂—N(CO—CH₂OH)—CH₂—, —(CH₂)₂—CH=CH—(CH₂)₂—.

Preferably, the group K linking the two macrocycles is a direct bond or the group $$-(O)_q-(CH_2)_n-\underset{OH}{(CH)_k}-(CH_2)_n-(O)_L-.$$

The functional groups are any moiety capable of reacting in a manner which will permit attachment of a biomolecule or macromolecule.

Preferred functional groups which $R^2$ of formulae IV, V, VI or VII can represent are, for example, maleimidobenzoyl, 3-sulfomaleimidobenzoyl, 4-(maleimidomethyl)cyclohexylcarbonyl, 4-[3-sulfo-(maleimidomethyl)]cyclohexylcarbonyl, 4-(p-maleimidophenyl)butyryl, 3-(2-pyridyldithio)propionyl, methacryloyl(pentamethylene) amido, bromoacetyl, iodoacetyl, 3-iodopropyl, 2-bromoethyl, 3-mercaptopropyl, 2-mercaptoethyl, phenyleneisothiocyanate, 3-aminopropyl, benzyl ester, ethyl ester, tert.-butyl ester, amino, hydroxy, $C_1$-$C_6$-alkylamino, aminocarbonyl, hydrazino, hydrazinocarbonyl, maleimido, methacrylamido, methacryloylhydrazinocarbonyl, maleimidamidocarbonyl, halogeno, mercapto, hydrazinotrimethylenehydrazinocarbonyl, aminodimethyleneamidocarbonyl, bromocarbonyl, phenylenediazonium, isothiocyanate, semicarbazide, thiosemicarbazide and isocyanate groups.

Several selected groups will be sent forth for the sake of explanation:

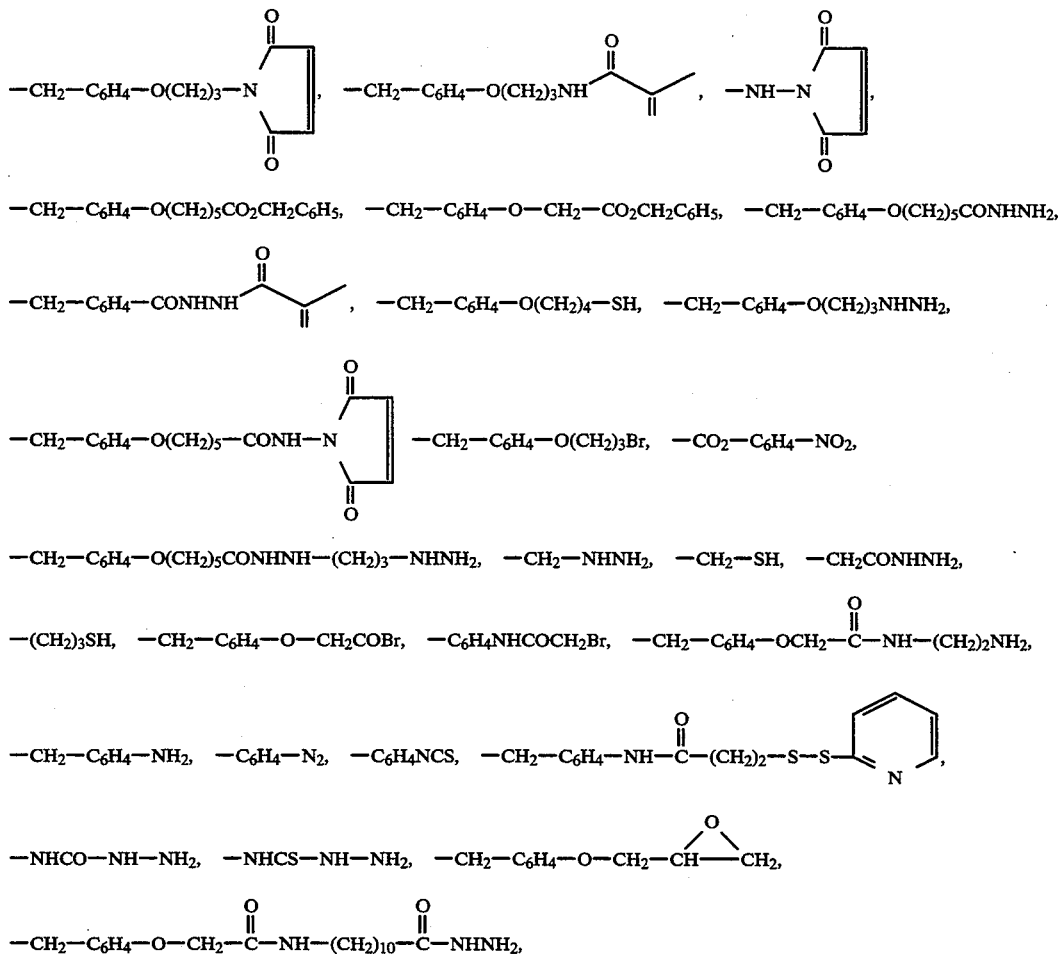

-continued

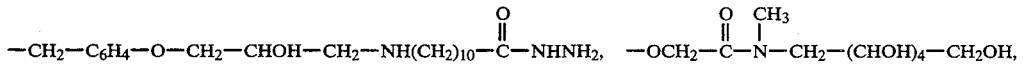

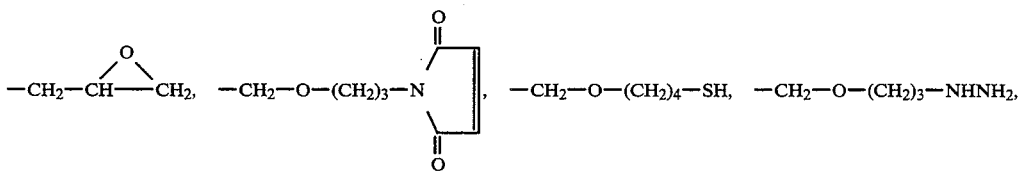

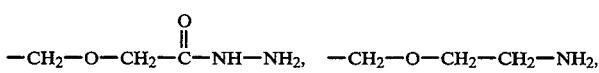

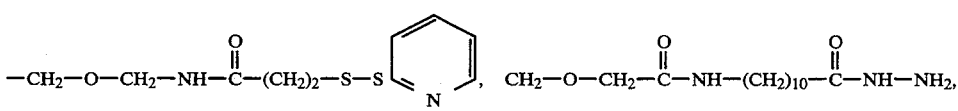

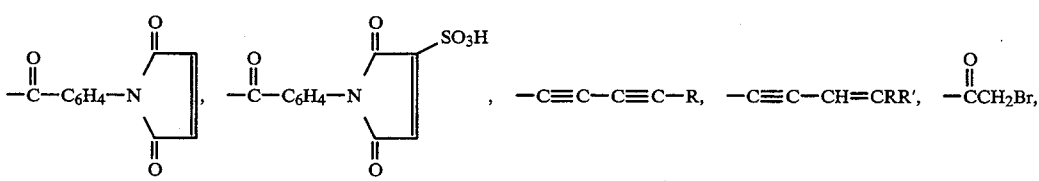

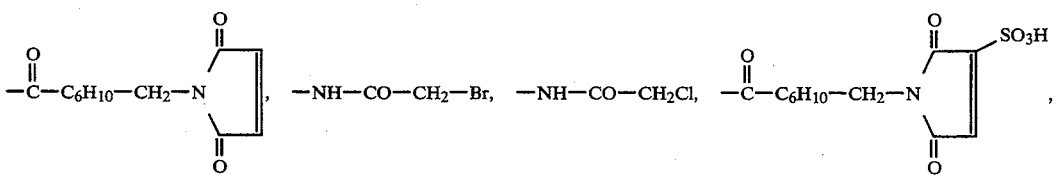

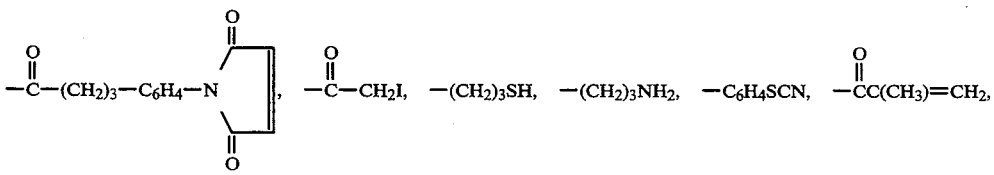

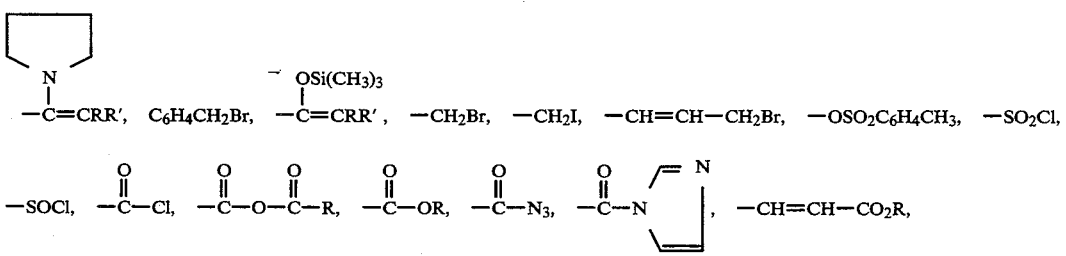

wherein R and R' are identical or different and in each case mean a hydrogen atom, a saturated or unsaturated $C_1$–$C_{20}$-alkyl residue optionally substituted by a phenyl group, or a phenyl group. The —NCS, —NO₂, —OH, —NHNH₂, —NHCOCH₂Br, —NHCOCH₂Cl, —CO₂H and —CON₃ groups are especially preferred.

The residual acidic hydrogen atoms, i.e., those that have not been substituted by the central ion, can optionally be replaced entirely or in part by cations of inorganic and/or organic bases or amino acids. The corresponding acid groups can also be entirely or partially converted into esters or amides.

Suitable inorganic cations are, for example, the lithium ion, the potassium ion, the calcium ion, the magnesium ion and especially the sodium ion. Suitable cations of organic bases are, inter alia, those of primary, secondary or tertiary amines, such as, for example, ethanolamine, diethanolamine, morpholine, glucamine, N,N-dimethylglucamine, and, in particular, N-methylglucamine. Suitable cations of amino acids are, for example, those of lysine, of arginine, and of ornithine, as well as the amides of otherwise acidic or neutral amino acids.

Suitable esters are preferably those with a $C_1$–$C_6$-alkyl residue; examples that can be mentioned are the methyl, ethyl and tert-butyl, benzyl and 4-methoxybenzyl residues.

If the carboxylic acid groups are to be present at least in part as amides, then suitable residues are saturated, unsaturated, straight- or branched-chain or cyclic hydrocarbons of up to 5 carbom atoms which are optionally substituted by 1-3 hydroxy or $C_1$–$C_4$-alkoxy groups. Examples that can be mentioned are the methyl, ethyl, 2-hydroxyethyl, 2-hydroxy-1-(hydroxymethyl) ethyl, 1-(hydroxymethyl)ethyl, propyl, isopropenyl, 2-hydroxypropyl, 3-hydroxypropyl, 2,3-dihydroxypropyl, butyl, isobutyl, isobutenyl, 2-hydroxybutyl, 3-hydroxybutyl, 4-hydoxybutyl, 2-, 3- and 4-hydroxy-2-methylbutyl, 2- and 3-hydroxyisobutyl, 2,3,4-trihydroxybutyl, 1,2,4-trihydroxybutyl, pentyl, cyclopental and 2-methoxyethyl groups. The amide residue can also be a heterocyclic 5- or 6-membered ring formed with the inclusion of the amide nitrogen. Examples that can be cited are: the pyrrolidinyl, piperidyl, pyrazolidinyl, pyrrolinyl, pyrazolinyl, piperazinyl, morpholinyl, imidazolidinyl, oxazolidinyl, thiazolidinyl rings.

The compounds of this invention exhibit the desired properties described in the foregoing. The complexes contain the metal ions, required for their usage, stably bound therein.

The value of the osmolality, responsible for side effects, such as pain, damage to the blood vessels, and cardiovascular disturbances, is markedly reduced as compared with MAGNEVIST® (compare Example 25b: 0.55 [osmol/kg] with MAGNEVIST® 1.96 [osmol/kg], 0.5 mol/l at 37° C.).

The value for the magnitude of relaxivity, representing a measure for imaging in MRI, is surprisingly high; the signal amplification in the plasma could be increased, for example in the case of the compound of Example 25b, by twice the value as compared with MAGNEVIST®.

A further advantage of the present invention resides in that complexes with hydrophilic or lipophilic substituents have now become accessible. This affords the possibility of controlling the compatibility and pharmacokinetics of these complexes by chemical substitution.

By the choice of suitable bio- or macromolecules (see farther below) in $R^2$ of formulae IV, V, VI and VII, complexes of this invention are obtained which exhibit a surprisingly high tissue and organ specificity.

The compounds of Formula IV are produced by splitting of the blocking groups conventionally in compounds of general Formula IV'

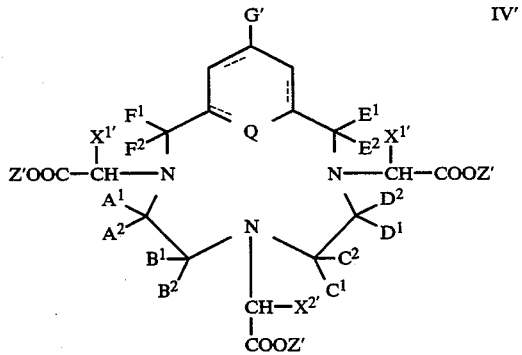

wherein $G'$, $X^{1'}$ and $X^{2'}$ in each case stand for G, $X^1$ and $X^2$ of Formula IV, the hydroxy groups and functional groups contained therein being present in the blocked form and, respectively, as a precursor, and $Z'$ means a hydrogen atom or an acid blocking group; optionally generating the desired functional group; reacting, if desired, the thus-obtained complexing compounds of general Formula I wherein Z means hydrogen in a manner known per se with at least one metal oxide or metal salt of an element of atomic numbers 21–29, 31, 32, 37–39, 42–44, 49 or 57–83; optionally binding the functional groups to a bio- or macromolecule—wherein the complexing can take place before or after the splitting off of the blocking groups for the hydroxy groups and functional groups and/or generation of the functional groups and linkage to a macro- or biomolecule—and subsequently, if desired, substituting any still present acidic hydrogen atoms by cations of inorganic and/or organic bases, amino acids or amino acid amides or, respectively, converting the corresponding acid groups entirely or partially into esters or amides.

Suitable acid blocking groups Z' are lower alkyl, aryl and aralkyl groups, e.g., the methyl, ethyl, propyl, n-butyl, tert.-butyl, phenyl, benzyl, diphenylmethyl, triphenylmethyl, bis(p-nitrophenyl)methyl groups as well as trialkylsilyl groups.

Z' can also stand for an alkali metal.

The blocking groups are split off in accordance with methods known to those skilled in the art, for example by hydrolysis, hydrogenolysis, alkaline saponification of the esters with alkali in an aqueous-alcoholic solution at temperatures of 0° to 50° C., acidic saponification with mineral acids or, in case of tert.-butyl esters, for example, with the aid of trifluoroacetic acid.

Suitable hydroxy blocking groups are, for example, the benzyl, 4-methoxybenzyl, 4-nitrobenzyl, trityl, diphenylmethyl, trimethylsilyl, dimethyl-tert.-butysilyl, diphenyl-tert.-butylsilyl groups.

The hydroxy groups can also be present, for example, as tetrahydropyranyl (THP) ethers, α-alkoxyethyl ethers, 2-methoxy-ethoxymethyl (MEM) ethers, or as esters with aromatic or aliphatic carboxylic acids, such as, for example, acetic acid or benzoic acid. In case of polyols, the hydroxy groups can also be blocked in the form of ketals with, for example, acetone, acetaldehyde, cyclohexanone or benzaldehyde.

The hydroxy groups present in and $X^{1'}$ and $X^{2'}$ can also be present in blocked form by intramolecular esterification with the α-positioned carboxy groups to obtain the corresponding lactones.

The hydroxy blocking groups can be liberated in accordance with literature methods known to a person skilled in the art, for example, by hydrogenolysis, reductive cleavage with lithium/ammonia, acid treatment of the ethers and ketals, or alkali treatment of the esters (see, for example, "Protective Groups in Organic Synthesis", T. W. Greene, John Wiley and Sons 1981).

The synthesis of dimeric compounds, i.e., compounds containing a second macrocycle of general Formula V or VII, takes place according to methods disclosed in the literature, for example, by way of an addition/elimination reaction of an amine with a carbonyl compound (e.g., acid chloride, mixed anhydride, activated ester, aldehyde); of two amine-substituted rings with a dicarbonyl compound (e.g., oxalyl chloride, glutaric dialdehyde); of two p-nitro-substituted nitroxides with bisalcoholates [cf. E. Klingsberg, The Chemistry of Heterocyclic Compounds, Interscience Publishers New York, p. 154 (1961)]; of two rings each exhibiting a nucleophilic group, with an alkylene compound carrying two leaving groups or, in case of terminal acetylenes, by oxidative coupling (Cadiot, Chodkiewicz in Viehe "Acetylenes", 597–647, Marcel Dekker, New York, 1969).

The ring-linking chain can subsequently be modified by secondary reactions (e.g., hydrogenation).

The synthesis of directly linked compounds (i.e., K meaning a direct bond, see Example 28) can be accomplished by cyclization of tetrahalogenomethyl-4,4'-bispyridines (see further below).

The synthesis of the educts IV' takes place by alkylation of compounds of general Formula VIII

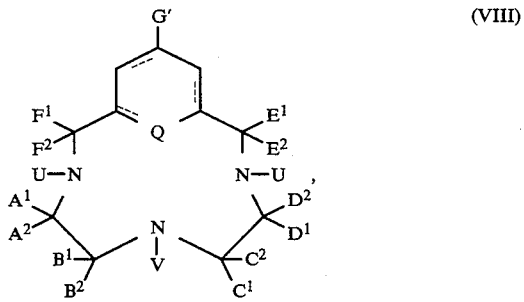

wherein
U is hydrogen and V is an amino blocking group or
U represents amino blocking groups and V is hydrogen,
wherein U and V can also be identical,
with compounds of general Formula IX

wherein Nf stands for a nucleofugal entity, such as, for example, Cl Br, I, $CH_3$—$C_6H_4SO_3$, $CH_3SO_3$, 4-$NO_2$—$C_6H_4SO_3$, $CF_3SO_3$.

The hydroxy groups that may be contained in $X^{1'}$ and $X^{2'}$ can also form a lactone together with the OZ' residue.

Examples for alkylating reagents are: bromoacetic acid, chloroacetic acid, bromoacetic acid methyl ester, bromoacetic acid tert.-butyl ester, chloroacetic acid benzyl ester, 2-chloro-3-benzyloxypropanoic acid sodium salt (EP 0,325,762), 2-bromo-3-benzyloxypropanoic acid tert-butyl ester (J. Gen. Chem., USSR 36:52, 1966), 3,4-O-isopropylidene-2-p-tolyl-sulfonyl-3,4-dihydroxybutyric acid ethyl ester (Synth. Comm. 19:3077, 1989), α-bromo-γ-butyrolactone.

Examples of amino blocking groups U and V, respectively, are: formyl, trifluoroacetate, benzoate, 4-nitrobenzoate, acetate, rosylate, mesylate, benzyl, 4-nitrobenzyl, 4-methoxybenzyl, trimethylsilyl, dimethyl tert.-butylsilyl.

Alkylation of the compounds of general Formula VIII to the educts of general Formula IV', with the compounds of general Formula IX or X takes place in polar aprotic solvents, such as, for example, dimethylformamide, acetonitrile, dimethyl sulfoxide, aqueous tetrahydrofuran, dioxane, or hexamethylphosphoric triamide in the presence of an acid captor, such as, for example, tertiary amine (e.g., triethylamine, trimethylamine, N, N-dimethylaminopyridine), 1,5-diazabicyclo[4.3.0]nonene-5 (DBN), 1,5-diazabicyclo[5.4.0]undecene-5 (DBU), alkali, alkaline earth carbonate, bicarbonate or hydroxide (e.g., sodium, lithium, magnesium, calcium, barium, potassium carbonate, hydroxide and bicarbonate) at temperatures of between −10° C. and 120° C., preferably between 0° C. and 50° C., it being possible to add, if desired, catalytic amounts of iodide or bromide.

After splitting off the remaining amino blocking group(s) according to methods known to one skilled in the art (for example acidic or alkaline hydrolysis, hydrogenolysis, reductive cleavage with alkali metals in liquid ammonia, reaction with tetrabutylammonium fluoride), the remaining amino function(s) is or are reacted in a second alkylating reaction with X and IX, respectively, so, that compounds-are obtained wherein $X^1 \neq X^2$.

The conversion of a precursor of the desired 6-membered ring contained in the final product takes place according to methods known to persons skilled in the art. Examples worth mentioning are the hydrogenation of pyridine [Advan. Catal. 14:203 (1963)], deoxygenation of nitroxide rings [E. Klingsberg, The Chemistry of Heterocyclic Compounds, vol. 14, part 2, Interscience Publishers New York, p. 120 (1961)], conversions and introduction of functional groups at the 6-membered ring, e.g., liberation of phenolic hydroxy groups [J. Org. Chem. 53:5 (1988)], introduction of halogen substituents [E. Klingsberg, The Chemistry of Heterocyclic Compounds, vol. 14, part 2, Interscience Publishers New York, p. 341 (1961); Houben-Weyl, Methoden der organischen Chemie, vo. V/3:651 (1962)].

Functionalization of 4-halopyridine derivatives (e.g., azide exchange) in the phase transfer process with the use of 18-crown-6 or tetrabutylammonium halogenide as the catalyst has been disclosed in "Phase Transfer Reactions" (Fluka Compendium vol. 2, Walter E. Keller, Georg Thieme publishers, Stuttgart, New York). A thus-obtained azide group can be converted into an amino function by using methods known to one skilled in the art (for example, catalytic hydrogenation, Houben-Weyl, "Methoden der organischen Chemie" vol. 11/1:539) or reaction with Raney nickel/hydrazine (German Patent Application 3,150,917). This amino function can be transformed into an isothiocyanate group by means of methods known from the literature (e.g. with thiophosgene in a two-phase system, S. Scharma, Synthesis 1978:803; D. K. Johnson, J. Med. Chem. 1989, vol. 32, 236).

By reacting an amino function with a haloacetic acid halogenide, an α-haloacetamide group can be generated (JACS 1969, vol. 90, 4508; Chem. Pharm. Bull. 29(1), 128, 1981), which is suitable, just as the isothiocyanate group, for example, for coupling to bio- and macromolecules.

The synthesis of the compounds of general Formula VII is conducted by cyclization according to methods known from the literature [for example, Org. Synth. 58:86 (1978), Macrocyclic Polyether Syntheses, Springer Publishers Berlin, Heidelberg, New York (1982); Coord. Chem. Rev. 3:3 (1968); Ann. Chem. 1976:916; J. Org. Chem. 49:110 (1984) ]; one of the two reactants carries two leaving groups at the chain end, the other carries two nitrogen atoms which displace these leaving groups in nucleophilic fashion.

An example that can be cited is the reaction of A'-$D^2$-substituted diethylenetriamines, the terminal-positioned nitrogen atoms of which displace, in nucleophilic fashion, the leaving groups of, for example, 2,6-dihalomethylpyridines, 2,6-ditosylmethylpyridines or 2,6-dimesylmethylpyridines. For the synthesis of directly linked dimers, 2,2',6,6'-tetrachloromethyl-4,4'-bispyridines (see, for example, Synthesis 552, 1989) are utilized in the cyclization reaction.

The nitrogen atoms are optionally blocked (for example as tosylates or trifluoroacetates) and are liberated prior to the subsequent alkylating reaction in accordance with methods known from the literature (the tosylates, for example, with mineral acids, alkali metals in liquid ammonia, hydrobromic acid and phenol, REDAL® (sodium-bis (2-methoxyethoxo) -aluminum-dihydride), lithium aluminum hydride, sodium amalgam, compare, for example, Liebigs Ann. Chem. 1977, 1344; Tetrahedron Letters 1976: 3477; the trifluoroacetates, for example, with mineral acids or ammonia in methanol, compare, for example, Tetrahedron Letters 1967: 289).

In order to prepare macrocycles with differing substitution on the nitrogen atoms, these atoms can be provided, in the educts, with different blocking groups, for example with rosylate and benzyl groups. The latter are then likewise removed according to conventional methods disclosed in the literature (preferably by hydrogenation, e.g., EP Patent Application 232,751).

In case diesters are utilized in the cyclization reaction, the resultant diketo compounds must be reduced according to methods known to one skilled in the art, for example, with diborane.

It is also possible to cyclize correspondingly substituted terminally positioned bisaldehydes or bisketones, e.g., 2,6-bisacetylpyridines, with the respectively desired terminal-positioned bisamines; the reduction of the thus-obtained Schiff bases takes place according to methods known from the literature, e.g., by catalytic hydrogenation (Helv. Chim. Acta 61: 1376 (1978)].

The amines required as starting materials for the cyclization are produced in analogy to methods known from the literature (e.g., EP 299,795). Starting with an N-blocked amine acid, a triamine is obtained by reaction with a partially blocked diamine (for example, according to the carbodiimide method), splitting off of the blocking groups, and diborane reduction.

Suitable substituents convertible into the functional group that can be linked to a macro- or biomolecule are, inter alia, hydroxy and nitrobenzyl, hydroxy and carboxyalkyl, as well as thioalkyl residues of up to 20 carbon atoms. They are converted, according to literature methods known to one skilled in the art [Chem. Pharm. Bull. 33:674 (1985); Compendium of Org. Synthesis vol. 1-5, Wiley and Sons, Inc.; Houben-Weyl, Methoden der organischen Chemie, vol. VIII, Georg Thieme publishers, Stuttgart; J. Biochem. 92:1413 (1982)], into the desired substituents (for example, with the amino, hydrazino, hydrazinocarbonyl, epoxy, anhydride, methacryloylhydrazinocarbonyl, maleimidamidocarbonyl, halogeno, halogenocarbonyl, mercapto, isothiocyanate group as the functional group). In case of the nitrobenzyl residue, catalytic hydrogenation (e.g., according to P. N. Rylander, Catalytic Hydrogenation over Platinum Metals, Academic Press 1967) to the aminobenzyl derivative must first be performed.

Examples of conversion of hydroxy or amine groups linked to aromatic or aliphatic residues are the reactions performed in suitable solvents, such as tetrahydrofuran, dimethoxyethane or dimethyl sulfoxide, two-phase aqueous systems, such as, for example, water/dichloromethane, in the presence of an acid captor, such as, for example, sodium hydroxide, sodium hydride, or alkali or alkaline earth carbonates, such as, for example, sodium, magnesium, potassium, calcium carbonate or poly(4-vinylpyridine) REILLEX®, at temperatures between 0° C. and the boiling point of the respective solvent, preferably, however, between 20° C. and 60° C., with a substrate of general Formula XI Nf—L—Fu  (XI)

wherein

L means an aliphatic, aromatic, arylaliphatic, branched, straight-chain or cyclic hydrocarbon residue of up to 20 carbon atoms, and Fu means the desired terminal-positioned functional group, optionally in the blocked form (DOS 3,417,413).

Examples of compounds of general Formula XI that can be cited are:

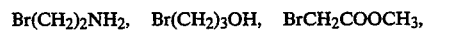

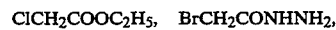

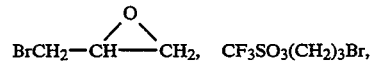

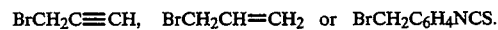

Conversions of carboxy groups can be conducted, for example, according to the carbodiimide method (Fieser, Reagents for Organic Syntheses 10:142), by way of a mixed anhydride [Org. Prep. Proc. Int. 7:215 (1975)], or via an activated ester (Adv. Org. Chem. part B, 472).

The thus-obtained complexing ligands (as well as the complexes) can also be linked to bio- or macromolecules of which it is known that they are particularly accumulated in the organ or organ part to be examined. Such molecules are, for example, enzymes, hormones, polysaccharides, such as dextrans or amyloses, porphyrins, bleomycins, insulin, prostaglandins, steroid hormones, amino sugars, amino acids, peptides, such as polylysine, proteins (e.g., immunoglobulins, monoclonal antibodies, lectins), lipids (also in the form of liposomes), and nucleotides of the DNA or RNA type. Especially to be emphasized are conjugates with albumins, such as human serum albumin, antibodies, e.g., monoclonal antibodies specific for tumor-associated antigens, or antimyosin. In place of biological macromolecules, it is also possible to use suitable synthetic polymers for the linkage, such as polyethylenimines, polyamides, polyureas, polyethers, such as polyethylene glycols and polythioureas. The pharmaceutical agents produced therefrom are suitable, for example, for use in tumor and infarction diagnostics as well as tumor therapy. Monoclonal antibodies (e.g., Nature 256:495, 1975) show the advantages over polyclonal antibodies that they are specific for an antigenic determinant, possess defined binding affinity, are homogeneous (thus substantially simplifying their preparation in pure form), and can be produced in cell cultures in large amounts. Suitable as such are, for example for tumor imaging, monoclonal antibodies and/or their fragments Fab and F(ab')₂ specific, for example, for human tumors of the gastrointestinal tract, the breast, the liver, the bladder, the gonads, and melanomas [Cancer Treatment Repts. 68:317 (1984); Bio. Sci. 34:150 (1984)], or acting against carcinoembryonic antigen (CEA), human chorionic gonadotropin (β-HCG), or other tumor-positioned antigens, such as glycoproteins [New Engl. J. Med. 298: 1384 (1973), U.S. Pat. No. 4,331,647]. Suitable are also, inter alia, antimyosin, antiinsulin, and antifibrin antibodies (U.S. Pat. No. 4,036,945).

Colon carcinomas can be detected with the aid of conjugates, complexed with gadolinium(III) ions, with the antibody 17-1A (Centocor, U.S.A.) by means of NMR diagnosis.

Suitable for liver examinations and, respectively, for tumor diagnosis are, for example, conjugates or inclusion compounds with liposomes which are used, for example, as unilamellar or multilamellar phosphatidyl-choline-cholesterol vesicles.

In case of the antibody conjugates, binding of the antibody of the complex or ligand must not lead to loss or reduction of binding affinity and binding specificity of the antibody to the antigen. This can be accomplished either by binding to the carbohydrate portion in the Fc part of the glycoprotein and/or in the Fab or F(ab')$_2$ fragments, or by binding to sulfur atoms of the antibody or, respectively, the antibody fragments.

In the first instance, an oxidative cleavage of sugar units must first be performed for the generation of formyl groups capable of coupling. This oxidation can be carried out by chemical methods with oxidizing agents such as, for example, periodic acid, sodium metaperiodate, or potassium metaperiodate in accordance with methods known from the literature (e.g., J. Histochem. and Cytochem. 22:1084, 1974) in an aqueous solution in concentrations of 1–100 mg/ml, preferably 1–20 mg/ml, and with a concentration of the oxidizing agent of between 0.001 and 10 millimoles, preferably 1 to 10 millimoles, in a pH range of about 4 to 8 at a temperature of between 0° and 37° C. and with a reaction period of between 15 minutes and 24 hours. The oxidation can also be performed by enzymatic methods, for example with the aid of galactose oxidase in an enzyme concentration of 10–100 units/ml, a substrate concentration of 1–20 mg/ml, at a pH of 5 to 8, a reaction period of 1–8 hours, and a temperature of between 20° and 40° C. (for example, J. Biol. Chem. 234:445, 1959).

Complexes or ligands with suitable functional groups, such as, for example hydrazinc, hydrazide, hydroxylamine, phenylhydrazine, semicarbazide and thiosemicarbazide, are bound to the aldehydes generated by oxidation; this is done by reacting between 0° and 37° C. with a reaction period of 1–65 hours, a pH of between about 5.5 and 8, an antibody concentration of 0.5–20 mg/ml, and a molar ratio of the complexing compound to the antibody aldehyde oil of 1:1 to 1000:1. The subsequent stabilization of the conjugate takes place by reduction of the double bond, for example with sodium borohydride or sodium cyanoborohydride; the reducing agent is utilized herein with a 10- to 100-fold excess (e,g., J. Biol. Chem. 254:4359, 1979).

The second possibility of forming antibody conjugates starts with a gentle reduction of the disulfide bridges of the immunoglobulin molecule; in this process, the more sensitive disulfide bridges between the H chains of the antibody molecule are cleaved whereas the S—S bonds of the antigen-binding region remain intact so that there is practically no reduction in binding affinity and specificity of the antibody (Biochem. 18:2226, 1979; Handbook of Experimental Immunology, vol. 1, 2nd ed., Blackwell Scientific Publications, London 1973, chapter 10). These free sulfhydryl groups of the inter-H-chain regions are then reacted with suitable functional groups of complexing compounds or metal complexes at 0°–37° C., a pH of about 4–7, and a reaction period of 3–72 hours with the formation of a covalent bond which does not affect the antigen binding region of the antibody. Suitable reactive groups are, for example: haloalkyl, haloacetyl, p-mercuribenzoate, isothiocyanate, thiol, epoxy groups, as well as groups to be subjected to a Michael addition reaction, such as, for example, maleinimides, methacrylo groups (e.g., J. Amer. Chem. Soc. 101:3097, 1979).

Additionally, for linking the antibody fragments with the polymer complexes or with the ligands, there is a number of suitable bifunctional "linkers" which are frequently also obtainable commercially (see, for example, Pierce, Handbook and General Catalogue 1986) which are reactive with respect to the SH groups of the fragments as well as with respect to the amino or hydrazino groups of the-complexes.

Examples that can be cited are:

m-maleimidobenzoyl-N-hydroxysuccinimide ester (MBS), m-maleimidobenzoyl-N-sulfosuccinimide ester (Sulfo-MBS), N-succinimidyl-[4-(iodoacetyl) amino]benzoic acid ester (SIAB), succinimidyl-4-(N-maleimidomethyl)cyclohexane-1-carboxylic acid ester (SMCC), succinimidyl-4-(p-maleimidophenyl)butyric acid ester (SMPB), N-succinimidyl-3-(2-pyridyldithio)propionic acid ester (SDPD), 4- [3-(2,5-dioxo-3-pyrrolinyl)propionyloxy]-3-oxo-2,5-diphenyl-2,3-dihydrothiophene-1,1-dioxide, acetylalanylleucylalanylaminobenzyl, acetamido-p-thioureidobenzyl.

It is also possible to utilize bonds not of the covalent type for coupling purposes wherein ionic as well as van der Waals and hydrogen bridge bonds can contribute toward the linkage in varying proportions and strengths (key and lock principle) (for example, avidin-biotin, antibody-antigen). Also inclusion compounds (host-guest) of relatively small complexes in relatively large cavities in the macromolecule are possible.

The coupling principle resides in first producing a bifunctional macromolecule by either fusing an antibody hybridoma directed against a tumor antigen with a second antibody hybridoma directed against a complex according to this invention, or linking the two antibodies chemically via a linker (e.g., in the way set forth in J. Amer. Chem. Soc. 101:3097, 1979) or binding the antibody directed against the tumor antigen to avidin (or biotin, respectively), optionally via a linker [D. J. Hnatowich et al., J. Nucl. Med. 28:1294 (1987)]. In place of the antibodies, it is also possible to employ their corresponding F(ab) or F(ab')$_2$ fragments. For pharmaceutical usage, first the bifunctional macromolecule is injected which is accumulated at the target site, and then, at a time interval, the complex compound of this invention is injected [optionally bound to biotin (or avidin) ] which is coupled on at the target site in vivo and there can deploy its diagnostic or therapeutic activity. Moreover, other coupling methods can likewise be utilized, such as, for example, "reversible radiolabeling" described in Protein Tailoring Food Med. Uses [Am. Chem. Soc. Symp. 349 (1985)].

A particularly simple method for the production of antibody conjugates or antibody fragment conjugates is available in the form of the so-called solid phase coupling procedure: The antibody is coupled to a stationary phase (e.g., an ion exchanger) located, for example, in a glass column. By successive flushing of the column with a solution suitable for generation of aldehyde groups, washing, rinsing with a solution of the functionalized complex, and finally elution of the conjugate, very high yields of conjugate are obtained.

This procedure permits the automatic and continuous production of any desired quantities of conjugates.

Also other coupling steps can be performed in this way.

Thus, for example, fragment conjugates can be prepared by the sequence of papain reduction/bifunctional linker/functionalized complex or ligand.

The thus-formed compounds are subsequently purified preferably by chromatography by way of ion exchangers on a fast protein liquid chromatography unit.

The production of the metal complexes according to the invention takes place in the manner, as it has been disclosed in the German Laid-Open Patent Application DE-OS 34 01 052, by dissolving or suspending the metal oxide or a metal salt (for example, the nitrate, acetate, carbonate, chloride or sulfate) of the element with atomic numbers 21–29, 31, 32, 37–39, 42–44, 57–83 in water and/or a lower alcohol (like methanol, ethanol or isopropanol) and reacting with the solution or suspension the equivalent amount of the complexing ligand, e.g., a complexing acid of general formula I with Y meaning a hydrogen atom, preferably at temperatures between 40° and 100° C., and then, if desired, substituting acid hydrogen atoms of acid groups present by cations of inorganic and/or organic bases, amino acids or amino acid amides.

Introduction of the desired metal ions can take place in this process before as well as after the splitting off of the blocking groups for the hydroxy groups and functional groups, or, respectively, before or after the generation of the functional groups and linkage to a macro- or biomolecule.

The neutralization takes place with the help of inorganic bases (for example, hydroxides, carbonates or bicarbonates) of, e.g., sodium, potassium, lithium, magnesium or calcium and/or organic bases such as, among others, primary, secondary and tertiary amines, such as, e.g., ethanolamine, morpholine, glucamine, N-methyl and N,N-dimethylglucamine, as well as basic amino acids, such as lysine, arginine and ornithine, for example, or of amides from originally neutral or acidic amino acids.

For the production of the neutral complex compounds, for example, as much of the desired bases can be added to the acid complex salts in aqueous solution or suspension that the neutral point is reached. The solution obtained can then be concentrated to dryness under vacuum. Often, it is advantageous to precipitate the neutral salts formed by addition of water-miscible solvents, as, for example, lower alcohols (methanol, ethanol, isopropanol and others), lower ketones (acetone and others), polar ethers (tetrahydrofuran, dioxane, 1,2-dimethoxyethane and others) and thus to obtain crystallizates easy to isolate and purify. It has been shown to be especially advantageous to add the desired base to the reaction mixture during the complexing, thereby saving a processing step.

If the acid complex compounds contain several free acid groups, then it is often expedient to produce neutral mixed salts, which contain both inorganic and organic counterions as ions of opposite charge.

This can take place, e.g., by reacting the complexing acid in aqueous suspension or solution with the oxide or salt of the element yielding the central ion and half of the amount of an organic base needed for the neutralization, isolating the complex salt formed, purifying it if desired, then mixing it for complete neutralization with the needed amount of inorganic base. The order of addition of the bases can also be reversed.

Another possibility of obtaining neutral complex compounds residues in converting the remaining acid groups in the complex entirely or partially into esters or amides, for example. This can be done by subsequent reaction of the finished complex (e.g., by exhaustive reaction of the free carboxy groups with dimethyl sulfate).

The conjugates of antibody and complex are dialyzed, prior to in vivo use, after incubation With a weak complexing agent, such as, for example, sodium citrate, sodium ethylenediaminetetraacetic acid, in order to remove weakly bound metal atoms.

In the case of the use of complex compounds containing radioisotopes, their production can be performed according to the methods described in "Radiotracers for Medical Applications," Volume 1, CRC-Press, Boca Raton, Fla.

The production of pharmaceutical agents according to the invention also takes place in a way known in the art, whereby the complex compounds according to the invention—optionally with the addition of the additives usual in galenicals—are suspended or dissolved in aqueous medium and then the suspension or solution is optionally sterilized. Suitable additives are, for example, physiologically harmless buffers (as, for example, tromethamine), small additions of complexing agents (as, for example, diethylenetriaminepentaacetic acid) or, if necessary, electrolytes such as, for example, sodium chloride or, if necessary, antioxidants as, for example, ascorbic acid.

If, for enteral administration or other purposes, suspensions or solutions of the media according to the invention in water or physiological saline solution are desired, they are mixed with one or more adjuvants usual in galenicals (e.g., methylcellulose, lactose, mannitol) and/or surfactant(s) (for example, lecithins, Tween ®, Myrj ® and/or flavorants such as aromatic substance(s) for taste modification (for example, ethereal oils).

In principle, it is also possible to produce the pharmaceutical agents according to the invention even without isolation of the complex salts. In any case, particular care must be used to perform the chelate formation so that the salts and salt solutions according to the invention are virtually free of uncomplexed metal ions with toxic effects.

This can be ensured, for example, with the help of color indicators such as xylenol orange, by control titrations during the production process. The invention therefore relates also to processes for the production of the complex compounds and their salts. As a final safety measure, purification of the isolated complex salt can be conducted.

The pharmaceutical media according to the invention preferably contain 1 $\mu$mol/l–1 mol/l of the complex salt and are as a rule dosed in amounts of about 0.1 $\mu$mol–5 mmol/kg of body weight, for example, about 0.001–5 mmol/kg. They are intended for enteral and parenteral application. The complex compounds according to the invention can be used 1. for NMR and X-ray diagnosis in the form of their complexes with the ions of the elements with atomic numbers 21–29, 42, 44 and 57–83; and
2. for radiodiagnosis and radiation therapy in the form of their complexes with the radioisotopes of the elements with atomic numbers 27, 29, 31, 32, 37–39, 43, 49, 62, 64, 70 and 77.

The media according to the invention fulfil the diverse prerequisites for suitability as contrast media for nuclear magnetic resonance imaging. Thus, they are eminently suitable, after oral or parenteral application, to improve the meaningfulness of the image obtained with the help of the nuclear magnetic resonance tomograph by increasing the signal intensity. Further, they show the high effectiveness that is necessary to load the body with the smallest possible amounts of foreign substances, and the good compatibility that is necessary to maintain the non-invasive character of the examinations.

The good water solubility and slight osmolality of the agents according to the invention make it possible to produce highly concentrated solutions, to keep the volume load of the circulation within justifiable limits and to balance the dilution by the body fluids. In other words, NMR diagnostic media should be 100 to 1000 times more water soluble than agents used for NMR spectroscopy. Furthermore, the media according to the invention exhibit not only a high stability in vitro, but also a surprising stability in vivo, so that a release or an exchange of the ions not covalently bonded in the complexes—and toxic in themselves—takes place only very slowly and within which time the new contrast media are completely excreted.

In general the media according to the invention are dosed for use as NMR diagnostic media in amounts of 0.0001–5 mmol/kg of body weight, for example about 0.001–5 mmol/kg of body weight, preferably 0.005–0.5 mmol/kg. Details of use are discussed, for example, in H. J. Weinmann et al., Am. J. of Roentgenology 142, 619 (1984).

Especially low dosages (under 1 mg/kg of body weight) of organ specific NMR diagnostic media can be used, for example, for the detection of tumors and of myocardial infarction.

Furthermore, the complex compounds according to the invention can be used advantageously as susceptibility reagents and as shift reagents for in vivo NMR spectroscopy.

The media according to the invention, on account of their favorable radioactive characteristics and the good stability of the complex compounds contained in them, are also suitable as radiodiagnostic media. Details of the use and dosage radiodiagnostic media are described, e.g., in "Radiotracers for Medical Applications," CRC-Press, Boca Raton, Fla.

A further imaging method with radioisotopes is positron emission tomography, which uses positron emitting isotopes such as, e.g., $^{43}$Sc, $^{44}$Sc, $^{52}$Fe, $^{55}$Co and $^{68}$Ga. (Heiss, W. D., Phelps, M. E., Positron Emission Tomography of Brain, Springer Verlag Berlin, Heidelberg, New York 1983).

The compounds according to the invention can also be used in radioimmuno or radiation therapy. This is distinguished from the corresponding diagnostics only by the amount and kind of isotope used. In this case, the objective is the destruction of tumor cells by energy rich shortwave radiation with the smallest possible range. Suitable beta-emitting ions are, for example, $^{46}$Sc, $^{47}$Sc, $^{48}$Sc, $^{72}$Ga, $^{73}$Ga and $^{90}$Y. Suitable alpha-emitting ions exhibiting small half-life periods are, for example, $^{211}$Bi, $^{212}$Bi, $^{213}$Bi and $^{214}$Bi, and $^{212}$Bi is preferred. A suitable photon and electron emitting ion is $^{158}$Gd, which can be obtained from $^{157}$Gd by neutron capture.

If the media of this invention is intended for use in the version of radiation therapy proposed by R. L. Mills et al. [Nature, vol. 336:787 (1988)], then the central ion must be derived from a Mössbauer isotope, such as, for example, $^{57}$Fe or $^{151}$Eu.

With in vivo application of the therapeutic media according to the invention, they can be administered together with a suitable vehicle as, for example, serum or physiological saline solution and together with another protein as, for example, human serum albumin. Here, the dosage is dependent on the kind of cellular disturbance, the metal ion used and the kind of imaging method, e.g., brachytherapy.

The therapeutic media according to the invention are applied parenterally, preferably i.v. (intravenously).

Details of the use of radiotherapeutic media are discussed, e.g., in R. W. Kozak et al., TIBTEC, October 1986, 262.

The media according to the invention are eminently suitable as X-ray contrast media, and it should be especially emphasized that, with the media according to the invention, no symptoms of the well known anaphylaxis type reactions to contrast media containing iodine are observed. They are especially valuable because of the good absorption characteristics in areas of higher tube voltages for digital substraction techniques.

In general, the media according to the invention for use as X-ray contrast media are dosed in analogy to meglumine-diatrizoate, for example, in amounts of about 0.1–5 mmol/kg, preferably 0.25–1 mmol/kg.

Details of the use of X-ray contrast media are discussed, for example, in Barke, Roentgenkontrastmittel (X-ray Contrast Media), G. Thieme, Leipzig (1970) and P. Thurn, E. Buecheler- "Einfuehrung in die Roentgendiagnostik" (Introduction to X-ray Diagnosis), G. Thieme, Stuttgart, New York (1977).

Overall there has been success in synthesizing new complexing media, metal complexes and metal complex salts, which open up new possibilities in diagnostic and therapeutic medicine. Especially the development of novel imaging processes in medical diagnosis makes this development appear desirable.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding applications German P 38 25 040.3, filed Jul. 20, 1988 and German P 40 01 655.2, filed Jan. 18, 1990, are hereby incorporated by reference.

The following examples will provide more a detailed explanation of the object of the invention.

EXAMPLES

Example 1 a) 3,6,9-tris(p-tolylsulfonyl)-3,6,9,15-tetraazabicyclo[9,3,1-]pentadeca-1(15),11,13-triene A solution of 35.2 g (200 mol) of 2,6-his-(chloromethyl)-pyridine (dissolved in 700 ml of dimethylformamide) is instilled into 121.9 g (200 mol) N,N',N''-tris(p-tolylsulfonyl)-diethylenetriamine-N,N''-disodium salt in 1600 ml of dimethylformamide at 100° C. within 3 hours. It is stirred overnight at 100° C. Into the hot solution, 2 l of water is instilled and it is allowed to cool to 0° C. The precipitate is suctioned off and washed with water. After drying in a vacuum (60° C.) it is recrystallized from acetonitrile. 92.3 g (69% of theory) of the title compound is obtained as colorless powder. Analysis: Calculated: C 57.46 H 5.43 N 8.38 O 14.35 S 14.38 Found: C 57.39 H 5.48 N 8.35 S 14.34 b) 3,6,9,15-tetraazabicyclo[9.3.1]pentadeca-1(15),11,13-triene tetrahydrosulfate 90.3 g (135 mmol) of the title compound from example 1a is added into 270 ml of concentrated sulfuric acid and stirred 48 hours at 100° C. It is cooled to 0° C. and 1.35 l of absolute ether is instilled into it. The precipitate is suctioned off and absorptively precipitated in 800 ml of methanol. After filtration and concentration by evaporation it is dried in a vacuum at 50° C.

Yield: 42.6 g (52.7% of theory) of a solid melting in the air. Analysis: Calculated: C 22.07 H 4.38 N 9.36 O 42.76 S 21.43 Found: C 22.10 H 4.42 N 9.31 S 21.40 c) 3,6,9,15-tetraazabicyclo[9.3.1]pentadeca-1(15),11,13-triene 40.0 g (66.8 mmol) of the title compound from example 1c is dissolved in 100 ml of water and is adjusted to pH 11 with 32% sodium hydroxide solution. It is extracted 8 times with 150 ml of methylene chloride and dried on magnesium sulfate. After concentration by evaporation in a vacuum, 9.79 g (71% of theory) of a yellowish powder is obtained. Analysis: Calculated: C 64.04 H 8.79 N 27.16 Found: C 63.91 H 8.85 N 26.98 d) 3,6,9-tris-(carboxymethyl)-3,6,9,15-tetraazabicyclo-[9.3.1]pentadeca-1(15),11,13-triene 33.1 g (55.1 mmol) of the title compound from example 1c is adjusted to pH 8.5 in 170 ml of water with 6 n potassium hydroxide solution. To this solution 20.84 g (220.5 mmol) of chloroacetic acid is added, adjusted with 6 n potassium hydroxide solution to pH 9.5 and heated to 45° C. It is stirred at this temperature for 12 hours and the pH is kept between 9.5–10 by addition of 6 n potassium hydroxide solution. After cooling to room temperature, it is adjusted to pH 2 with concentrated hydrochloric acid and is evaporated to dryness. The residue is extracted with 300 ml of ethanol/50 ml of acetone, the solid is filtered off and the filtrate is concentrated by evaporation in a vacuum. The residue is dissolved in a little water and poured onto a cation exchanger column (IR 120). After rinsing with water the ligand is eluted with 0.5 n aqueous ammonia solution. The fractions are concentrated by evaporation, taken up with a little water and poured on an anion exchanger column (IRA 67). It is first washed with water and then eluted with 0.5 n formic acid. It is concentrated by evaporation in a vacuum and the residue is dissolved in a little hot ethanol. By careful addition of acetone and cooling in the ice bath the title compound is crystallized out.

Yield: 12.37 g (59% of theory) of a strongly hygroscopic compound. Analysis: Calculated: C 53.67 H 6.36 N 14.73 O 25.24 Found: C 53.55 H 6.43 N 14.65 e) Gadolinium complex of 3,6,9-tris-(carboxymethyl)-3,6,9,15-tetraazabicyclo-[9.3.1]pentadeca-1(15),11,13-triene 5.0 g (13.14 mmol) of the title compound from example 1d is dissolved in 20 ml of deionized water and 2.38 g (6.57 mmol) of gadolinium oxide is added. It is stirred for 3 hours at 90° C. The solution is filtered and the filtrate is freeze-dried.

Yield: 7.74 g (100% of theory) of a white amorphous powder, which according to analysis contains 9.31% water. Analysis: Calculated: C 38.19 H 3.96 N 10.46 O 17.98 Gd 29.41 Found: C 38.11 H 4.05 N 10.38 Gd 29.32

The following relaxivity was measured in the plasma (the measurements of relaxation times $T_1$ took place in a minispec p20 (Bruker) at 0.46 tesla (=20MHz) at 40° C.):

$T_1$ relaxivity: 7.64 (L/mmol sec)

In comparison: dimeglumine salt of the gadolinium complex of diethylenetriaminepentaacetic acid (Gd-DPTA):

$T_1$ relaxivity: 4.95 (L/mmol sec)

Osmolality of a 0.5 molar solution at 37° C.:

0.55 (Osml/kg of water)

In comparison: dimeglumine salt of Gd-DTPA:

1.1 (Osml/kg of water).

In a similar way with iron(III) oxide, $Fe_2O_3$, the iron(III) complex of 3,6,9-tris(carboxymethyl)-3,6,9,15-tetraazabicyclo-[9.3.1]-pentadeca-1(15),11,13-triene is obtained as brown powder. Analysis (relative to anhydrous substance) Calculated: C 47.13 H 4.89 N 12.83 Fe 12.893 Found: C 47.04 H 4.96 N 12.84 Fe 12.81 $T_1$ relaxivity (L/mmol.sec), 40° C., water, 20 MHz: 0.49 f) Dysprosium complex of 3,6,9-tris-(carboxymethyl)-3,6,9,15-tetraazabicyclo[9.3.1]pentadeca-1(15),11,13-triene If instead of gadolinium oxide in example 1e dysprosium oxide is used, the title compound is obtained virtually in quantitative yield. Analysis: Calculated: C 37.82 H 3.92 N 10.38 O 17.78 Dy 30.10 Found: C 37.87 H 3.98 N 10.24 Dy 30.02 g) ytterbium complex of 3,6,9-tris-(carboxymethyl)-3,6,9,15-tetraazabicyclo[9.3.1]pentadeca-1(15),11,13-triene If instead of gadolinium oxide in example 1e ytterbium oxide is used, the title compound is obtained virtually in quantitative yield. Analysis: Calculated: C 37.09 H 3.85 N 10.18 O 17.44 Yb 31.44 Found: C 37.13 H 3.94 n 10.09 Yb 31.37 h) meglumine salt of manganese(II) complex of 3,6,9-tris-(carboxymethyl)-3,6,9,15-tetraazabicyclo[9.3.1]pentadeca-1(15),11,13-triene 3.0 g (7.89 mmol) of the title compound from example 1d is dissolved in 20 ml of deionized water and 907 mg (7.89 mmol) of manganese (II) carbonate is added. It is stirred for 2 hours at 80° C. The solution is filtered and the filtrate is adjusted to pH 7.2 with a 1 molar N-methyl-glucamine solution. Then it is freeze-dried.

Yield: 5.56 g (100% of theory) of a slightly pink looking amorphous powder, which according to analysis contains 12.2% water. Analysis: Calculated: C 45.86 H 6.25 N 11.14 O 28.00 Mn 8.74 Found: C 45.98 H 6.21 N 11.08 Mn 8.68

Example 2 a)
3,6,9-tris-(carboxymethyl)-3,6,9,15-tetraazabicyclo-[9.3.1]pentadecane 6.0 g (15.77 mmol) of the title compound from example 1d is dissolved in 200 ml of 5% hydrochloric acid and hydrogenated in an autoclave on a rhodium catalyst (5% Rd/C) at 30 bars, 45° C. After 4 hours it is filtered from the catalyst and concentrated by evaporation in a vacuum. The residue is purified in ion exchangers as described in example 1d. Crystallization from methanol/acetone yields 4.75 g (78% of theory) of an extremely hygroscopic compound. Analysis: Calculated: C 52.83 H 7.83 N 14.50 O 24.84 Found: C 52.94 H 7.89 N 14.37 b) Gadolinium complex of 3,6,9-tris(carboxymethyl)-3,6,9,15-tetraazabicyclo[9.3.1]pentadecane 2.02 g (5.57 mmol) of gadolinium oxide is added to 4.3 g (11.13 mmol) of the title compound from example 2a in 20 ml of deionized water and is stirred for 3 hours at 90° C. The solution is filtered and the filtrate is freeze-dried. 6.5 g (100% of theory) of a white, flaky powder is obtained, which according to analysis contains 10.3% water. Analysis: Calculated: C 37.76 H 5.03 N 10.36 O 17.76 Gd 29.08 Found: C 37.63 H 5.12 N 10.33 Gd 28.97

Example 3 a)
3,6,9-tris(acetyl)-3,6,9,15-tetraazabicyclo[9.3.1]-pentadeca-1(15),11,13-triene 15.8 g (76.6 mmol) of the title compound from example 1c, 42.7 ml of triethylamine (306.4 mmol) and 50 mg of dimethylaminopyridine (DMAP) are dissolved in 300 ml of absolute methylene chloride. 28.9 ml (306.4 mmol) of acetic anhydride is added and it is stirred overnight at room temperature. The solvent is concentrated by evaporation in a vacuum and the residue is taken up with 200 ml of 3% sodium carbonate solution. It is extracted 2 times with 150 ml of methylene chloride. After drying of the organic phase on magnesium sulfate it is concentrated by evaporation in a vacuum. The residue is recrystallized from ether/ethyl acetate. 23.93 g (94% of theory) of the title compound is obtained as white flakes. Analysis: Calculated: C 61.42 H 7.28 N 16.86 O 14.44 Found: C 61.48 H 7.37 N 16.80 b)
3,6,9-tris(acetyl)-3,6,9,15-tetraazabicyclo[9.3.1]-pentadeca-1(15),11,13-triene-15-N-oxide 22.5 g (67.7 mmol) of the title compound from example 3a is dissolved in 100 ml of glacial acetic acid. 7.7 ml of a 30% hydrogen peroxide solution is added and heated for 4 hours to 70° C. Then an additional 3.9 ml of 30% hydrogen peroxide solution is added and it is stirred an additional hour at 70° C. It is concentrated by evaporation in a vacuum to a third and is carefully mixed with saturated sodium carbonate solution until the alkaline reaction. It is extracted twice with 250 ml of methylene chloride and then the organic phases are dried on magnesium sulfate. After concentration by evaporation in a vacuum and crystallization from ether/ethyl acetate, 18.63 g (79% of theory) of the title compound is obtained as crystalline powder. Analysis: Calculated: C 58.60 H 6.94 N 16.08 O 16.07 Found: C 58.47 H 6.88 N 16.14 c)
13-nitro-3,6,9-tris(acetyl)-3,6,9,15-tetraazabicyclo-[9.3.1]pentadeca-1(15),11,13-triene-15-N-oxide 17 g (48.8 mmol) of the title compound from example 3b is dissolved in 40 ml of 90% sulfuric acid and heated to 60° C. To this solution 14 ml of concentrated nitric acid (d=1.36) is instilled and is stirred for 3 hours at 60° C. It is poured on ice, the precipitate is filtered and it is washed with much water. After drying in a vacuum an orange powder is obtained, which is recrystallized from acetone.

Yield: 9.2 g (48% of theory) yellow thombuses. Analysis: Calculated: C 51.90 H 5.89 N 17.80 O 24.40 Found: C 52.01 H 5.76 N 17.64 d)
13,13'-ethylenedioxy-bis[3,6,9-tris-(acetyl)-3,6,9,15tetraazabicyclo-[9.3.1]pentadeca-1(15),11,13-triene-15-N-oxide]

A freshly prepared solution of ethylene glycol disodium in dimethylformamide (produced from 620 mg of ethanediol and 600 mg of sodium hydride [80% suspension in paraffin oil] in 15 ml of anhydrous dimethylformamide) is instilled within 10 minutes in a 50° C. warm solution of 8 g (20.34 mmol) of the title compound from example 3c and is stirred overnight at this temperature. 10 ml of water is added and it is concentrated by evaporation in a vacuum. The residue is chromatographed on silica gel (mobile solvent: methanol/32% aqueous ammonia solution: 10/1). After crystallization from ether/ethyl acetate 3.15 g (41% of theory) of a yellowish crystalline powder is obtained. Analysis: Calculated: C 57.28 H 6.68 N 14.85 O 21.19 Found: C 57.40 H 6.61 N 14.79 e)
13,13'-ethylenedioxy-bis[3,6,9-tris-(acetyl)-3,6,9,15tetraazabicyclo[9.3.1]pentadeca-1(15),11,13-triene]

3 g (3.97 mmol) of the title compound from example 3d is dissolved in 100 ml of ethanol, 1 ml of concentrated hydrochloric acid is added and hydrogenated on Pd/C. It is filtered from the catalyst, concentrated by evaporation in a vacuum and the residue is taken up with 50 ml of a 3% sodium carbonate solution. It is extracted twice with 100 ml of methylene chloride. After drying of the organic phases on magnesium sulfate, the solvent is removed in a vacuum and is crystallized from ether/ethyl acetate.

Yield: 2.87 g (87% of theory) of white flakes Analysis: Calculated: C 59.81 H 6.97 N 15.50 O 17.71 Found: C 59.70 H 6.91 N 15.39 f)
13,13'-ethylenedioxy-bis[3,6,9,15-tetraazabicyclo[9.3.1]pentadeca-1(15),11,13-triene]

2.5 g (3.46 mmol) of the title compound from example 3e and 4.66 g (41.5 mmol) of potassium tert.-butylate are dissolved in 40 ml of dioxane under nitrogen and refluxed overnight. It is concentrated by evaporation in a vacuum, the residue is taken up with 50 ml of water and it is brought to pH 10 with 2 n sodium hydroxide solution. After extraction 6 times with 80 ml of methylene chloride each time, it is dried on magnesium sulfate and the solvent is removed in a vacuum.

Yield: 1.55 g (95% of theory) of a pale yellow oil, which crystallizes when allowed to stand. Analysis: Calculated: C 61.25 H 8.14 N 23.81 O 6.80 Found: C 61.17 H 8.20 N 23.93 g) 13,13'-ethylenedioxy-bis[3,6,9-tris-(carboxymethyl)-3,6,9,15-tetraazabicyclo[9.3.1]pentadeca-1(15),11,13-triene]

1.4 g (2.97 mmol) of the title compound from example 3f is dissolved in 20 ml of water and 2.25 g (23.8 mmol) of chloroacetic acid is added. With 6 n potassium hydroxide solution it is adjusted to pH 9.5. It is stirred for 12 hours at 45° C. and the pH is maintained between 9.5–10 by addition of 6 n potassium hydroxide solution. It is brought to pH 2 with concentrated hydrochloric acid and is purified on ion exchangers as described in example 1d. Crystallization from ethanol/acetone yields 1.3 g (57% of theory) of the title compound as a strongly hygroscopic solid. Analysis: Calculated: C 52.80 H 6.16 N 13.69 O 27.35 Found: C 52.67 H 6.07 N 13.75 h) gadolinium complex of 13,13'-ethylenedioxy-bis[3,6,9-tris(carboxymethyl)-3,6,9,15-tetraazabicyclo[9.3.1]pentadeca-1(15),11,13-triene]

1.2 g (1.47 mmol) of the title compound from example 3g is dissolved in 8 ml of deionized water and 533 mg (1.47 mmol) of gadolinium oxide is added. It is stirred for 3 hours at 90° C. The solution is filtered and the filtrate is freeze-dried.

Yield: 1.85 g (100% of theory) of an amorphous powder, which according to analysis contains 11.3% water. Analysis: Calculated: C 38.45 H 3.93 N 9.94 O 19.87 Gd 27.90 Found: C 38.60 H 3.98 N 10.03 Gd 27.79

Example 4 a) 13-ethinyl-3,6,9-tris(acetyl)-3,6,9,15-tetraazabicyclo[9.3.1]pentadeca-1(15),11,13-triene-15N-oxide 10 g (25.42 mmol) of the title compound from example 3c is dissolved in 200 ml of dimethoxyethane (DME) under nitrogen. 1.22 g (25.42 mmol) of sodium acetylide (18% suspension in xylene/light mineral oil) is added and it is stirred overnight at room temperature. 10 ml of water is added and it is evaporated to dryness. The residue is chromatographed on silica gel (mobile solvent: methanol/acetone=1:1). Crystallization from ether/ethyl acetate yields 5.02 g (53% of theory) of the title compound as a bright yellow powder. Analysis: Calculated: C 61.27 H 6.49 N 15.05 O 17.19 Found: C 61.31 H 6.55 N 14.94 b) 13,13'-(1,3-butadiyne-1,4-diyl)-bis([3,6,9-tris-(acetyl)-3,6,9,15-tetraazabicyclo[9.3.1]pentadeca-1(15),11,13-triene]-15-N-oxide)

4.75 g (12.75 mmol) of the title compound from example 4a is dissolved in 200 ml of pyridine and mixed with 2.52 g (25.5 mmol) of copper (I) chloride.. The solution is saturated with oxygen and then stirred for two days at room temperature. Here it must be guaranteed that an oxygen atmosphere is constantly maintained. After concentration of the solution by evaporation in a vacuum, the residue is chromatographed on silica gel (mobile solvent: methanol/acetone=1/2). Crystallization from ether/ethyl acetate yields 2.7 g (57% of theory) of a weakly yellowish powder. Analysis: Calculated: C 61.27 H 6.49 N 15.05 O 17.19 Found: C 61.31 H 6.55 N 14.94 c) 13,13'-(1,3-butadiyne-1,4-diyl)-bis[3,6,9-tris-(acetyl)-3,6,9,15-tetraazabicyclo[9.3.1]pentadeca-1(15),11,13-triene]

2.5 g (3.37 mmol) of the title compound from example 4b is dissolved in 50 ml of glacial acetic acid and heated to 60° C.

1.88 g (33.65 mmol) of iron powder is added and it is stirred for 2 hours at 60° C. It is filtered from the solid and the filtrate is evaporated to dryness. The residue is taken up with 100 ml of 3% sodium carbonate solution and extracted three times with 100 ml of chloroform. After drying on magnesium sulfate the solvent is removed in a vacuum and it is crystallized from ether/acetone.

Yield: 2.08 g (87% of theory) of a colorless powder Analysis: Calculated: C 64.21 H 6.52 N 15.77 O 13.51 Found: C 64.31 H 6.60 N 15.68 d) 13,13'-(1,3-butadiyne-1,4-diyl)-bis[3,6,9,15-tetraazabicyclo[9.3.1]pentadeca-1(15),11,13-triene]

1.9 g (2.67 mmol) of the title compound from example 4c is dissolved in 20 ml of dioxane under nitrogen. 2.4 g (21.38 mmol) of potassium tert.-butylate is added and it is refluxed overnight. The solvent is removed in a vacuum and the residue is taken up with 20 ml of water. It is adjusted with 2 n sodium hydroxide solution to pH 10 and is extracted six times with 60 ml of methylene chloride. After drying of the organic phases on magnesium sulfate it is concentrated by evaporation in a vacuum.

Yield: 1.09 g (89% of theory) of a pale yellow oil. Analysis: Calculated: C 68.09 H 7.47 N 24.44 Found: C 68.18 H 7.54 N 24.51 e) 13,13'-(1,3-butadiyne-1,4-diyl)-bis[3,6,9-tris-(carboxymethyl)-3,6,9,15-tetraazabicyclo[9.3.1]pentadeca-1(15),11,13-triene]

1.0 g (2.18 mmol) of the title compound from example 4d is dissolved in 15 ml of water and 1.65 g (17.44 mmol) of chloroacetic acid is added. It is adjusted with 6 n potassium hydroxide solution to pH 9.5 and stirred for 12 hours at 45° C. Here the pH is maintained between 9.5–10 by addition of 6 n potassium hydroxide solution. After acidifying with concentrated hydrochloric acid it is purified on ion exchangers as described in 1d. Crystallization from methanol/acetone yields 1.07 g (61% of theory) of a strongly hygroscopic solid. Analysis: Calculated: C 56.57 H 5.75 N 13.89 O 23.79 Found: C 56.64 H 5.81 N 13.79 f) Gadolinium complex of 13,13'-(1,3-butadiyne-1,4-diyl)-bis[3,6,9-tris(carboxymethyl)-3,6,9,15-tetraazabicyclo[9.3.1]pentadeca-1(15),11,13-triene]

900 mg (1.116 mmol) of the title compound from example 4e is dissolved in 8 ml of water and 404 mg (1.116 mmol) of gadolinium oxide is added. After three hours of stirring at 90° C. the solution is filtered and the filtrate is freeze-dried.

Yield: 1.35 g (100% of theory) of a white amorphous powder, which according to analysis contains 8.9% of water. Analysis: Calculated: C 40.92 H 3.62 N 10.05 O 17.22 Gd 28.20 Found: C 40.81 H 3.65 N 10.18 Gd 28.11

Example 5 a)
13-chloro-3,6,9-tris(acetyl)-3,6,9,15-tetraazabicyclo[9.3.1]pentadeca-1(15),11,13-triene-15-N-oxide 7.3 g (18.56 mmol) of the title compound from example 3c is heated in 50 ml of acetyl chloride for 4 hours to 50° C. It is concentrated by evaporation in a vacuum and the residue is taken up in 200 ml of 3% sodium carbonate solution. It is extracted three times with 100 ml of chloroform and dried on magnesium sulfate. After removal of the solvent in a vacuum, it is re-crystallized from ether/ethyl acetate.

Yield: 6.18 g (87% of theory) of a colorless crystalline powder. Analysis: Calculated: C 53.33 H 6.05 N 14.64 O 16.72 Cl 9.26 Found: C 53.48 H 5.98 N 14.71 Cl 9.20 b)
13-chloro-3,6,9-tris(acetyl)-3,6,9,15-tetraazabicyclo[9.3.1]pentadeca-1(15),11,13-triene 6.0 g (15.67 mmol) of the title compound from example 5a is dissolved in 300 ml of ethanol. 1 ml of concentrated hydrochloric acid is added and it is hydrogenated on Pd/C. After hydrogen absorption is finished, it is filtered from the catalyst and concentrated by evaporation in a vacuum. The residue is taken up with 100 ml of 3% sodium carbonate solution and extracted twice with 100 ml of chloroform. The organic phases are dried on magnesium sulfate and concentrated by evaporation in a vacuum. Crystallization of the residue from ether/acetic acid yields 5.34 g (93% of theory) of the title compound as a colorless powder. Analysis: Calculated: C 55.66 H 6.32 N 15.27 O 13.08 Cl 9.66 Found: C 55.57 H 6.38 N 15.31 Cl 9.59 c)
13-chloro-3,6,9,15-tetraazabicyclo[9.3.1]pentadeca-1(15),11,13-triene 5.1 g (13.9 mmol) of the title compound from example 5b is dissolved in 50 ml of dioxane under nitrogen. 6.24 g (55.6 mmol) of potassium tert.-butylate is added and it is refluxed overnight. It is worked up as described in example 4d.

Yield: 3.01 g (90% of theory) of a slightly yellowish oil, which crystallizes after a short time. Analysis: Calculated: C 54.88 H 7.12 N 23.28 Cl 14.73 Found: C 54.93 H 7.06 N 23.41 Cl 14.81 d)
13-chloro-3,6,9-tris(carboxymethyl)-3,6,9,15-tetraazabicyclo[9.3.1]pentadeca-1(15),11,13-triene 2.38 g (11.65 mmol) of the title compound from example 5c is dissolved in 30 ml of water and 4.4 g (46.6 mmol) of chloroacetic acid is added. It is adjusted to pH 9.5 with 6 n potassium hydroxide solution. It is stirred for 12 hours at 45° C. and the pH is maintained between 9.5–10 by addition of 6 n potassium hydroxide solution. After working up as described in example 1d and crystallization from methanol/acetone, 3.23 g (67% of theory) of the title compound is obtained as a solid that melts in air. Analysis: Calculated: C 49.22 H 5.59 N 13.51 O 23.14 Cl 8.55 Found: C 49.31 H 5.65 N 13.60 Cl 8.49 e) Gadolinium complex of 13-chloro-3,6,9-tris(carboxymethyl)-3,6,9,15-tetraazabicyclo[9.3.1]pentadeca-1(15),11,13-triene 3.23 g (7.78 mmol) of the title compound from example 5d is dissolved in 20 ml of deionized water and 1.41 g (3.89 mmol) of gadolinium oxide is added. It is stirred for 3 hours at 90° C. The solution is filtered and the filtrate is freeze-dried.

Yield: 4.9 g (100% of theory) of a white amorphous powder, which according to analysis contains 11.9% water. Analysis: Calculated: C 35.88 H 3.54 N 9.85 O 16.87 Cl 6.23 Gd 27.63 Found: C 35.94 H 3.57 N 10.01 Cl 6.17 Gd 27.56

$T_1$ relaxivity (L/mmol-sec), 40° C., water 20 MHz: 5.44

Example 6 a)
3,6,9,15-tetraazabicyclo[9.3.1]pentadeca-1(15),11,13-triene-15-N-oxide 4.5 g (12.9 mmol) of the title compound from example 3b is dissolved in 40 ml of dioxane under nitrogen. 5.8 g (51.7 mmol) of potassium tert.-butylate is added and it is refluxed overnight. After working up as described in example 3f, 2.61 g (91% of theory) of a slightly yellow oil is obtained which crystallizes when allowed to stand. Analysis: Calculated: C 59.43 H 8.16 N 25.20 O 7.20 Found: C 59.37 H 8.21 N 25.13 b)
3,6,9-tris(carboxymethyl)-3,6,9,15-tetraazabicyclo[9.3.1]pentadeca-1(15),11,13-triene-15-N-oxide 2.4 g (10.77 mmol) of the title compound from example 6a is dissolved in 30 ml of water and 4.1 g (43.4 mmol) of chloroacetic acid is added. It is adjusted to pH 9.5 with 6 n potassium hydroxide solution. It is stirred for 12 hours at 45° C. and the pH-value is maintained between 9.5–10 with addition of 6 n potassium hydroxide solution. After working up as described in example 1d, the crystallization from ethanol/acetone yields 2.7 g (63% of theory) of a strongly hygroscopic powder. Analysis: Calculated: C 51.51 H 6.10 N 14.14 O 28.26 Found: C 51.63 H 6.01 N 14.08 c) Gadolinium complex of 3,6,9-tris(carboxymethyl)-3,6,9,15-tetraazabicyclo[9.3.1]pentadeca-1(15),11,13-triene-15-N-oxide 2.1 g (5.3 mmol) of the title compound from example 6b is dissolved in 15 ml of deionized water and 935 mg (2.65 mmol) of gadolinium oxide is added. It is stirred for 3 hours at 90° C. The solution is filtered and the filtrate is freeze-dried.

Yield: 3.2 g (100% of theory) of an amorphous powder, which according to analysis contains 10.7% water. Analysis: Calculated: C 37.08 H 3.84 N 10.18 O 20.34 Gd 28.56 Found: C 37.18 H 3.79 N 10.21 Gd 28.48

Example 7 a)
3,6,9-tris(p-tolylsulfonyl)-3,6,9-triaza-14-oxabicyclo[9.2.1]tetradeca-1-(13),11-diene A solution of 33 g (200 mmol) of 2,5-bis(chloromethyl)-furan in 700 ml of dimethylformamide is instilled into 121.9 g (200 mmol) of N,N',N"-tris(p-tolylsulfonyl)diethylenetriamine-N,N"-disodium salt in 1600 ml dimethylformamide at 100° C. within 3 hours. It is stirred overnight at 100° C. Into the hot solution 2 liters of water is instilled. It is cooled to 0° C. The precipitate is washed with much water and dried in a vacuum (60° C.). After crystallization from acetonitrile 88.14 g (67% of theory) of a white powder is obtained. Analysis: Calculated: C 56.60 H 5.36 N 6.39 O 17.03 S 14.62 Found: C 56.52 H 5.42 N 6.30 S 14.60 b)
3.6.9-triaza-14-oxa-bicyclo[9.2.1]tetradeca-1(13),11-diene 30 g (45.61 mmol) of the title compound from example 7a is suspended in 500 ml of liquid ammonia at −40° C. Then within 30 minutes, 10.49 g (456.1 mmol) of sodium is added and it is stirred for 3 hours at −40° C. The excess of sodium is destroyed by careful addition of ethanol (discoloration) and ammonia is allowed to evaporate. The residue is taken up with 100 ml of water and is adjusted to pH 11 with 6 n sodium hydroxide solution. Then it is extracted six times with 150 ml of methylene chloride, the organic phase is dried on magnesium sulfate and concentrated by evaporation in a vacuum. The residue is chromatographed on silica gel (mobile solvent: acetonitrile/water/32% ammonia solution=10/3/1).

Yield: 3.95 g (45% of theory) of a pale yellow oil. Analysis: Calculated: C 61.51 H 8.78 N 21.52 O 8.19 Found: C 61.43 H 8.85 N 21.47 c)
3,6,9-tris(ethoxycarbonylmethyl)-3,6,9-triaza-14-oxabicyclo[9.2.1]tetradeca-1(13),11-diene 7 ml (62.5 mmol) of bromoacetic acid ethyl ester is slowly instilled at 50° C. within 10 minutes into a mixture of 3.7 g (18.95 mmol) of the title compound from example 7b and 6.03 g (56.85 mmol) of anhydrous sodium carbonate in 150 ml of dimethylformamide. It is stirred for 4 hours at 50° C. The solvent is removed in a vacuum and the residue is absorptively precipitated in 200 ml of methylene chloride. It is filtered from the solid and the filtrate is concentrated by evaporation. The remaining oil is chromatographed on silica gel (mobile solvent: methylene chloride/ethanol=12/1).

Yield: 6.1 g (71% of theory) of a yellowish oil, which slowly congeals. Analysis: Calculated: C 58.26 H 7.78 N 9.27 O 24.69 Found: C 58.17 H 7.88 N 9.19 d) Gadolinium complex of 3,6,9-tris(carboxymethyl)-3,6,9-triaza-14-oxa-bicyclo[9.2.1]tetradeca-1(13),11-diene 5.0 g (11.02 mmol) of the title compound from example 7c is dissolved in 80 ml of ethanol and at 60° C. 36 ml of 1 n sodium hydroxide solution is slowly instilled. It is refluxed for 30 minutes. It is evaporated to dryness, taken up with 20 ml of water and is carefully brought to pH 6.5 with 2 n hydrochloric acid. After addition of 2.0 g (5.57 mmol) of gadolinium oxide it is stirred for 3 hours at 90° C. The solution is filtered and the filtrate is first poured onto a short cation exchanger column (IR-120), then it is poured onto a short anion exchanger column (IRA-67). The eluate is freeze-dried.

Yield: 4.9 g (78% of theory) of an amorphous powder which according to analysis contains 9.7% water. Analysis: Calculated: C 36.70 H 3.85 N 8.03 O 21.39 Gd 30.03 Found: C 36.51 H 3.81 N 8.11 Gd 29.91

Example 8

Gadolinium complex of 3,6,9-tris(carboxymethyl)-3,6,9,14-tetraaza-bicyclo-[9.2.1]tetradeca-1(13),11-diene 10.0 g (22.04 mmol) of the title compound from example 7c is dissolved in 150 ml of ethanol and at 60° C. 80 ml of 1 n sodium hydroxide solution is instilled. It is refluxed for one hour and then evaporated to dryness. The residue is conveyed into a shaker autoclave and 3.54 g (66.12 mmol) of ammonium chloride is added. After addition of vanadium oxide catalyst (US Patent 2 478 456, Chem. Abstr. 44, 665(1950)) 100 ml of ammonia is condensed in. It is heated for 12 hours to 200° C. After evaporation of the ammonia the residue is chromatographed on silica gel (mobile solvent: dioxane/water/32% aqueous ammonia solution=6/2/1). Concentration by evaporation yields approximately 5.19 g (56% of theory) of the extremely hygroscopic ammonium salt, which is immediately reacted again. It is dissolved in 25 ml of deionized water and adjusted to pH 6.5 with 2 n hydrochloric acid. 2.24 g (6.17 mmol) of gadolinium oxide is added and it is stirred for 3 hours at 90° C. under nitrogen. 1 g of activated carbon is added and it is stirred an additional hour at 90° C. The solution is filtered and the filtrate is poured first onto a short cation exchanger column (IR-120), then onto a short anion exchanger column (IRA-67). The eluate is freeze-dried.

Yield: 6.0 g (47% of theory relative to the title compound from example 7c) of an amorphous powder which according to analysis contains 11.1% water. Analysis: Calculated: C 36.84 H 3.87 N 10.74 O 18.40 Gd 30.15 Found: C 36.75 H 3.91 N 10.68 Gd 30.04

Example 9 a)
15-methoxy-3,6,9-tris(p-tolylsulfonyl)-3,6,9-triazabicyclo[9.3.1]pentadeca-1 (15),11,13-triene 182.85 g (300 mmol) of N,N',N"-tris(p-tolylsulfonyl)-diethylenetriamine-N,N"-disodium salt is dissolved in 2.4 liters of dimethylformamide and heated to 100° C. To it a solution of 88.2 g (300 mmol) of 2,6-bis(bromomethyl)phenolmethyl ether in 1 liter of dimethylformamide is instilled within 3 hours. It is stirred overnight at 100° C. Into the hot solution 3 liters of water is instilled and it is cooled to 0° C. The precipitate is washed with much water and dried in a vacuum (60° C.). Crystallization from acetonitrile yields 119.3 g (57% of theory) of the title compound as a slightly cream-colored powder. Analysis: Calculated: C 58.51 H 5.63 N 6.02 O 16.05 S 13.78 Found: C 58.41 H 5.68 N 6.13 S 13.70 b)
15-hydroxy-3,6,9-triazabicyclo[9.3.1]-pentadeca-1(15),11,13-triene 21.75 g (573.2 mmol) of lithium aluminum hydride is carefully added to 100 g (143.3 mmol) of the title compound from example 9a in 2 liters of dibutyl ether and refluxed overnight. It is cooled in an ice bath and excess lithium aluminum hydride is destroyed with ethanol and then with water. It is evaporated to dryness, the residue is taken up with 1 liter of 2 n sodium hydroxide solution and is extracted ten times with 200 ml of chloroform. After drying on magnesium sulfate it is concentrated by evaporation in a vacuum and the residue is chromatographed on silica gel (mobile solvent: methanol/32% aqueous ammonia solution=10/1).

Yield: 8.56 g (27% of theory) of a yellowish oil. Analysis: Calculated: C 65.13 H 8.65 N 18.99 O 7.23 Found: C 65.18 H 8.60 N 19.10 c)
15-hydroxy-3,6,9-tris(tert.-butoxycarbonymethyl)-3,6,9-triazabicyclo[9.3.1]pentadeca-1(15),11,13-triene 8.3 g (37.50 mmol) of the title compound from example 9b is dissolved in 250 ml of dimethylformamide and 15.55 g (112.5 mmol) of anhydrous potassium carbonate is added. To this 16.3 ml (112.5 mmol) of bromoacetic-acid tert.-butyl ester is instilled within 30 minutes and is stirred overnight at room temperature. The solvent is evaporated to dryness, it is taken up with 300 ml of water and extracted three times with 150 ml of methylene chloride. The organic phases are dried on magnesium sulfate and concentrated by evaporation in a vacuum. The remaining oil is chromatographed on silica gel (mobile solvent: methylene chloride/methanol=15/1).

Yield: 13.32 g (63% of theory) of the title compound as colorless oil. Analysis: Calculated: C 63.91 H 8.75 N 7.45 O 19.87 Found: C 63.83 H 8.85 N 7.49 d)
15-hydroxy-3,6,9-tris-(carboxymethyl)-3,6,9,-triazabicyclo[9.3.1]pentadeca-1(15),11,13-triene 13.0 g (23.06 mmol) of the title compound from example 9c is dissolved in 150 ml of trifluoroacetic acid and stirred overnight at room temperature. It is concentrated by evaporation in a vacuum. The residue is taken up with a little water and is purified on ion exchangers as described in example 1d. Crystallization from methanol/acetone yields 6.5 g (71% of theory) of the title compound as a powder that melts in the air. Analysis: Calculated: C 54.67 H 6.37 N 10.63 O 28.33 Found: C 54.51 H 6.30 N 10.57 e) Gadolinium complex of 15-hydroxy-3,6,9-tris(carboxymethyl)-3,6,9-triazabicyclo[9.3.1]pentadeca-1(15),11,13-triene 4.0 g (10.1 mmol) of the title compound from example 9d is dissolved in 25 ml of deionized water and 1.84 g (5.05 mmol) of gadolinium oxide is added. It is stirred for 3 hours at 90° C., 1 g of activated carbon is added and it is stirred an additional hour at this temperature. The solution is filtered and the filtrate is freeze-dried. 6.04 g (96% of theory) of an amorphous powder is obtained, which according to analysis contains 13.5% water. Analysis: Calculated: C 39.33 H 4.04 N 7.65 O 20.38 Gd 28.61 Found: C 39.41 H 4.10 N 7.58 Gd 28.51

Example 10 a)
6-benzyl-3,9-bis(p-tolylsulfonyl)-3,6,9,15-tetraazabicyclo[9.3.1]-pentadeca-1(15),11,13-triene A solution of 35.2 g (200 mmol) of 2,6-bis(chloromethyl)pyridine (dissolved in 700 ml of dimethylformamide) is instilled into 109.12 g (200 mmol) of N,N''-bis(p-tolylsulfonyl)-N'-benzyl-diethylenetriamine-N,N''-disodium salt in 1500 ml of dimethylformamide, at 100° C. within 3 hours. It continues to be stirred overnight at 100° C. Into the hot solution 2 liters of water is instilled and it is cooled to 0° C. The precipitate is washed with water several times and dried in a vacuum (60° C.). Crystallization from acetonitrile/ether yields 78.6 g (65% of theory) of a cream-colored powder. Analysis: Calculated: C 63.55 H 6.00 N 9.26 O 10.58 S 10.60 Found: C 63.48 H 5.94 N 9.18 S 10.63 b)
6-benzyl-3,6,9,15-tetraazabicyclo[9.3.1]pentadeca-1(15),11,13-triene 9.41 g (248 mmol) of lithium aluminum hydride is carefully added to 75 g (124 mmol) of the title compound from example 10a in 1.5 liters of dibutyl ether, and it is refluxed overnight. After cooling in an ice bath the excess lithium aluminum hydride is destroyed with ethanol and water. It is evaporated to dryness, taken up with 500 ml of water and adjusted to pH 11 with 6 n potassium hydroxide solution. It is extracted six times with 100 ml of chloroform, dried on magnesium sulfate and concentrated by evaporation in a vacuum. Chromatography on silica gel (mobile solvent: ethanol/32% aqueous ammonia solution=12/1) yields 22.4 g (61% of theory) of a yellowish oil, which congeals in a glassy manner. Analysis: Calculated: C 72.94 H 8.16 N 18.90 Found: C 72.75 H 8.23 N 18.81 c)
6-benzyl-3,9-bis(ethoxycarbonylmethyl)-3,6,9,15tetraazabicyclo[9.3.1]pentadeca-1(15),11,13-triene 10 g (33.74 mmol) of the title compound from example 10b is dissolved in 300 ml of dimethylformamide. 7.13 g (67.48 mmol) of anhydrous sodium carbonate is added and it is heated to 50° C. Then within 15 minutes 8.3 ml (74.2 mmol) of bromoacetic acid ethyl ester is instilled and it continues to be stirred overnight at 50° C. The solvent is evaporated in a vacuum, the residue is absorptively precipitated twice with 350 ml of methylene chloride, filtered and concentrated by evaporation. The remaining oil is chromatographed on silica gel (mobile solvent: methylene chloride/ethanol=10/1).

Yield: 13.12 g (83% of theory) of the title compound as colorless oil. Analysis: Calculated: C 66.64 H 7.74 N 11.96 O 13.66 Found: C 66.51 H 7.81 N 11.88 d)
3,9-bis(carboxymethyl)-3,6,9,15-tetraazabicyclo[9.3.1-]pentadeca-1(15),11,13-triene 12 g (25.6 mmol) of the title compound from example 10c is dissolved in 100 ml of ethanol and heated to 60° C. To this solution 32 ml of 2n sodium hydroxide solution is instilled and it is refluxed for one hour. It is evaporated to dryness and the residue is dissolved in 200 ml of 5% acetic acid. It is hydrogenated on Pd/C. After hydrogen absorption is finished, it is filtered from the catalyst, concentrated by evaporation in a vacuum and purified as described in example 1d on ion exchangers. Crystallization from ethanol/acetone yields 6.52 g (79% of theory) of a strongly hygroscopic solid. Analysis: Calculated: C 55.88 H 6.88 N 17.38 O 19.85 Found: C 55.79 H 6.94 N 17.27 e) Manganese (II) complex of 3,9-bis(carboxymethyl)-3,6,9,15-tetraazabicyclo[9.3.1-]pentadeca-1(15),11,13-triene 4 g (12.4 mmol) of the title compound from example 10d is dissolved in 20 ml of deionized water and 1.43 g (12.4 mmol) of manganese (II) carbonate is added. It is heated for 2 hours to 80° C. The solution is first poured onto a short cation exchanger column (IR-120), then onto a short anion exchanger column (IRA-67). The eluate is refluxed with 1 g of activated carbon for an hour and filtered. The filtrate is freeze-dried. 4.4 g (87% of theory) of a slightly pink shiny amorphous powder is obtained. Analysis: Calculated: C 48.00 H 5.37 N 14.93 O 17.05 Mn 14.64 Found: C 47.93 H 5.41 N 14.87 Mn 14.58

Example 11 a) 3,6-bis-(p-tolylsulfonyl)-3,6,12-triazabicyclo[6.3.1]-dodeca-1(12),8,10-triene A solution of 35.2 g (0.2 mol) of 2,6-bis(chloromethyl)-pyridine (dissolved in 700 ml of dimethylformamide) is instilled into 82.48 g (0.2 mol) of N,N'-bis(p-tolylsulfonyl)-ethylenediamine-di-sodium salt in 1600 ml of dimethylformamide, at 100° C. within 3 hours. It continues to be stirred overnight at 110° C. Into the hot solution 2 liters of water is instilled, the precipitate is suctioned off and washed with much water. After drying in a vacuum (60° C.) it is recrystallized from acetonitrile.

Yield: 67.9 g (72% of theory) of a cream-colored powder. Analysis: Calculated: C 58.58 H 5.34 N 8.91 O 13.57 S 13.60 Found: C 58.41 H 5.37 N 8.85 S 13.53 b) 3,6,12-triazabicyclo[6.3.1]dodeca-1(12),8,10-triene trihydrosulfate 67.0 g (142 mmol) of the title compound from example 11a is added to 200 ml of concentrated sulfuric acid and stirred for 48 hours at 100° C. It is cooled to 0° C. and 1 liter of absolute ether is instilled. The precipitate is suctioned off and is absorptively precipitated in 600 ml of methanol. It is filtered and then evaporated to dryness. Drying in a vacuum (60° C.) yields 44.17 g (68% of theory) of the title compound as crystalline solid. Analysis: Calculated: C 23.63 H 4.19 N 9.19 O 41.97 S 21.03 Found: C 23.57 H 4.24 N 9.11 S 20.96 c) 3,6,12-triazabicyclo[6.3.1]dodeca-1(12),8,10-triene 42.0 g (91.8 mmol) of the title compound from example 11b is dissolved in 100 ml of water and adjusted to pH 11 with 32% sodium hydroxide solution. It is extracted six times with 200 ml of methylene chloride and the combined phases are dried on magnesium sulfate. After concentration by evaporation in a vacuum, 11.24 g (75% of theory) of a slightly yellow oil is obtained. Analysis: Calculated: C 66.23 H 8.03 N 25.74 Found: C 66.17 H 8.09 N 25.67 d) 3,6-bis(carboxymethyl)-3,6,12-triazabicyclo[6.3.1]-dodeca-1(12),8,10-triene 10 g (61.27 mmol) of the title compound from example 11c is dissolved in 100 ml of water and 17.37 g (183.8 mmol) of chloroacetic acid is added. It is adjusted to pH 9.5 by addition of 6 n potassium hydroxide solution and heated to 45° C. It is stirred at this temperature for 12 hours, and the pH is maintained between 9.5–10 by addition of 6 n potassium hydroxide solution. It is cooled and purified as described in example 1d on ion exchangers. Crystallization from ethanol/acetone yields 11.47 g (67% of theory) of the title compound as crystalline solid. Analysis: Calculated: C 55.90 H 6.14 N 15.05 O 22.92 Found: C 55.81 H 6.19 N 14.94 e) Manganese complex of 3,6-bis(carboxymethyl)-3,6,12-triazabicyclo[6.3.1-]dodeca-1(12),8,10-triene 10.0 g (35.8 mmol) of the title compound from example 11d is dissolved in 40 ml of deionized water and 4.12 g (35.8 mmol) of manganese (II) carbonate is added. It is stirred for 2 hours at 80° C. The solution is poured onto a short anion and cation exchanger column and the eluate is stirred with 1 g of activated carbon for 1 hour at 80° C. It is filtered and the filtrate is freeze-dried.

Yield: 12.7 g (96% of theory) of the title compound as amorphous powder, which according to analysis contains 11.3% water. Analysis: Calculated: C 47.00 H 4.55 N 12.65 O 19.26 Mn 16.54 Found: C 46.95 H 4.61 N 12.58 Mn 16.48

Example 12

Production of a solution of gadolinium complex of 3,6,9-tris(carboxymethyl)-3,6,9,15-tetraazabicyclo[9.3.1]-pentadeca-1(15),11,13-triene 534.63 g (1 mol) of the compound described in example 1e was dissolved in 1200 ml of water pro injectione (p.i.). After addition of 24.62 g (50 mmol) of monohydrate of calcium trisodium salt of DTPA, CaNa₃DTPA, it is filled with water p.i. up to 2000 ml. The solution is then ultra-filtered, put into ampules and sterilized by heat and is ready for use for parenteral application.

Example 13

Production of a solution of the meglumine salt of manganese (II) complex of 3,6,9-tris(carboxymethyl)-3,6,9,15-tetraazabicyclo[9.3.1]pentadeca-1(15),11,13-triene 34.92 g (50 mmol) of the compound described in example 1h (water content 12.29%) is dissolved in 65 ml of water (p.i.). After addition of 492 mg (1 mmol) of monohydrate of the calcium trisodium salt of DTPA, CaNa₃DTPA, it is filled with water p.i. to 100 ml. The solution is finally ultra-filtered, put into ampules and sterilized by heat and is ready for use for parenteral application.

Example 14

Composition of a powder for the production of a suspension for oral application:

4,000 g of the gadolinium complex described in example 1e
3,895 g of mannitol
0.100 g of polyoxyethylenepolyoxypropylene polymer
0.005 g of aromatic substances
8.000 g

Example 15

Production of a solution of indium(III) complex of 3,6,9-tris(carboxymethyl)-3,6,9,15-tetraazabicyclo[9.3.1]-pentadecane A solution of 100 micrograms of the compound described in example 2a in 5 ml of a mixture of a 150 mmolar sodium chloride and a 150 mmolar sodium acetate solution (pH 5.8) is mixed with a solution of 5 ml of indium(III) chloride in 1 ml of n-hydrochloric acid. It is brought to pH 7.2 by addition of 0.1 n-sodium hydroxide solution, the sterilely filtered solution is filled into multivials and lyophilized. The residue is taken up in physiological saline solution and then represents a preparation suitable for radiodiagnosis.

In a similar way a preparation suitable for radiotherapy is obtained with yttrium 90 chloride.

Example 16 a) 3,6,9-tris(p-tolylsulfonyl)-14-oxa-3,6,9-triazabicyclo[9.2.1]tetradecane 39.01 g (64 mmol) of N,N',N''-tris(p-tolylsulfonyl)-diethylenetriamine-N,N''-disodium salt dissolved in 210 ml of dimethylformamide is instilled into a solution of 28.19 g (64 mmol) of 2,5-bis(p-tosyloxymethyl)-tetrahydrofuran in 500 ml of dimethylformamide within 2 hours at 100° C. and is stirred for 5 hours at 120° C. Into the hot solution 700 ml of water is instilled and it is cooled to 0° C. The precipitate is suctioned off, washed with water and dried in a vacuum at 50° C. After recrystalization from acetone 33.5 g of the title compound is obtained as white powder, melting point 175°–178° C. Analysis: Calculated: C 56.26 H 5.94 N 6.35 S 14.53 Found: C 56.01 H 5.99 N 6.28 S 14.29 b) 14-oxa-3,6,9-triazabicyclo[9.2.1]tetradecane 30 g (45.3 mmol) of the title compound from example 16a is added into 90 ml of concentrated sulfuric acid and stirred for 24 hours at 90° C. It is then cooled to 0° C. and 350 ml of dry ether is instilled. The precipitate formed is suctioned off and is dissolved in 50 ml of 40% sodium hydroxide solution and the solution is extracted 10 times with 50 ml of dichloromethane each. The organic phase is dried on magnesium sulfate and concentrated by evaporation in a vacuum. 6.23 g (69% of theory) of the title compound is obtained as white powder. Analysis: Calculated: C 60.27 H 10.62 N 21.08 Found: C 60.03 H 10.75 N 20.95 c) 3,6,9-tris-(carboxymethyl)-14-oxa-3,6,9,-tetraazabicyclo[9.2.1]tetradecane 6 g (30.1 mmol) of the title compound from example 16b is dissolved in 35 ml of water, mixed with 11.38 g (120.4 mmol) of chloroacetic acid and this solution is adjusted to pH 9.5 with 6N potassium hydroxide solution. It is heated for 12 hours to 45° C. and during this time the pH is maintained at 9.5–10 by addition of more potassium hydroxide solution. Then it is cooled to room temperature, mixed slowly with concentrated hydrochloric acid until reaching pH 2 and then concentrated by evaporation in a vacuum. The residue is dissolved in 100 ml of water and this solution is poured onto a cation exchanger column (IR 120). First the column is washed with much water. Then the desired substance is eluted with 0.5N ammonia solution, the solution is concentrated by evaporation, the residue is dissolved in 100 ml of water and the solution is poured onto a anion exchanger column (IRA 67). First of all it is washed with water, then it is eluted with 0.5N formic acid. The acid fractions are concentrated by evaporation, the residue is dissolved in methanol. After addition of acetone, the title compound (5.74 g, 51% of theory) crystallizes out.

Analysis: Calculated: C 51.47 H 7.29 N 11.25 Found: C 51.60 H 7.21 N 11.38 d) Gadolinium complex of 3,6,9-tris-(carboxymethyl)-14 oxa-3,6,9-triazabicyclo[9.2.1]tertradecane 3.73 g (10 mmol) of the title compound from example 16c is dissolved in 15 ml of water and stirred for 3 hours with 1.81 g (5 mmol) of gadolinium oxide at 80° C. The solution obtained is filtered and successively absorptively precipitated with 0.5 g of cation exchanger (IR 120) and 0.5 g of anion exchanger (IRA 67), the solution is again filtered and subjected to freeze-drying. 5.07 g (91% of theory) of the title compound is obtained as white amorphous power with a water content of 5.4%. Analysis: Calculated: C 36.42 H 4.59 N 7.96 Gd 29.80 Found: C 36.30 H 4.61 N 7.82 Gd 29.59 (water content taken into account)

Example 17 a) 3,6,9-tris(p-tolylsulfonyl)-14-thia-3,6,9-triazabicyclo[9.2.1]tetradeca-1(13),11-diene 60.97 g (100 mmol) of N,N',N''-tris(p-tolylsulfonyl)-diethylenetriamine-N,N''-disodium salt is dissolved in 800 ml of dimethylformamide and 19.9 g (110 mmol) of 2,5-bis-chloromethylthiophene, dissolved in 330 ml of dimethylformamide, is instilled at 50° C. within 90 minutes. It is stirred another 90 minutes at 50° C., then 1 liter of water is instilled and the precipitate formed is suctioned off, it is washed with water and the residue is dried at 50° C. in a vacuum drying chamber and recrystallized from dioxane. 47.1 g (70% of theory) of the title compound is obtained as a light yellow powder, melting point 265°–268° C. Analysis: Calculated: C 55.25 H 5.24 N 6.24 S 19.03 Found: C 55.38 H 5.44 N 6.10 S 19.01 b) 14-thia-3,6,9-triazabicyclo[9.2.1]tetradeca-1(13),11-diene 45 g (66.8 mmol) of the title compound from example 17a is added to 130 ml of concentrated sulfuric acid and stirred for 24 hours at 90°–95° C. After cooling to 0° C., 500 ml of ether is instilled, it is suctioned off from the precipitate formed and the precipitate is dissolved in 70 ml of 40% sodium hydroxide solution. The solution is extracted five times with 100 ml of dichloromethane each time, dried on magnesium sulfate and concentrated by evaporation in a vacuum. The residue is recrystallized from ether/hexane (3:1) and 7.8 g (55% of theory) of the title compound is obtained as white powder. Analysis: Calculated: C 56.83 H 8.11 N 19.88 S 15.17 Found: C 56.59 H 8.02 N 20.12 S 15.00 c) 3,6,9-tris-(carboxymethyl)-14-thia-3,6,9-triazabicyclo[9.2.1]tetradeca-1(13),11-diene 7.5 g (35.5 mmol) of the title compound from example 17b is dissolved in 45 ml of water, mixed with 13.42 g (142 mmol) of chloroacetic acid and the pH is adjusted to 9.5 with 6N potassium hydroxide solution. Then it is heated for 12 hours to 45°–50° C. and the pH is maintained at 9.5–10 by addition of more potassium hydroxide solution. After cooling to 10° C. it is mixed with concentrated hydrochloric acid until reaching pH 2. The precipitate thus formed is isolated by suctioning off, it is dissolved in 100 ml of water and the solution is adsorbed on a cation exchanger column (IR 120), the column is washed with 2 l of water, then with 0.5N ammonia solution. The ammonia fraction is concentrated by evaporation in a vacuum, the residue is dissolved in 100 ml of water and the solution is bonded on an anion exchanger (IRA 67). The exchanger column is eluted with water and 0.5N formic acid. From the acid fraction the title compound is obtained by concentration by evaporation in a vacuum. For additional purification methanol is dissolved and precisely enough acetone is added until a precipitate forms. It is cooled to 0° C., it is suctioned off from the precipitate and 7.7 g (56.3% of theory) of the title compound is obtained as light yellow powder. Analysis: Calculated: C 49.86 H 6.01 N 10.90 S 8.32 Found: C 49.71 H 5.85 N 10.80 S 8.07 d) Gadolinium complex of 3,6,9-tris-(carboxymethyl)-14-thia-3,6,9-triazabicyclo[9.2.1]tetradeca-1(13),11-diene 2 g (5.19 mmol) of the title compound from example 17c is heated with 941 mg (2.60 mmol) of gadolinium oxide in 20 ml of water for 4 hours to 85°–90° C. The solution obtained is filtered and successively absorptively precipitated with 0.26 g of cation exchanger (IR 120) and 0.25 g of anion exchanger (IRA 67), the solution is again filtered and freeze-dried. 2.66 g (95% of theory) of the title compound is obtained as white amorphous power, water content 5.7%. Analysis: Calculated: C 35.61 H 3.74 Gd 29.14 N 7.79 S 5.94 Found: C 35.50 H 3.51 Gd 29.02 N 7.98 S 6.18 (water content taken into account in the calculation)

Example 18 a) 13-methoxy-3,6,9-tris(p-tolylsulfonyl)-3,6,9,15-tetraazabicyclo[9.2.1]-pentadeca-1(15),11,13-triene 60.97 g (100 mmol) of N,N',N"-tris(p-tolylsulfonyl)-diethylenetriamine-N,N"-disodium salt is dissolved in 800 ml of dimethylformamide and 47.76 g (100 mmol) of 2.6-bis-(p-tolylsulfonyloxymethyl)-4-methoxy-pyridine, dissolved in 400 ml of dimethylformamide, is instilled at 50° C. within 90 minutes. It is stirred for 5 hours more at 90° C., then 1.1 liter of water is instilled, the precipitate formed is suctioned off, washed with water, the product is dried in a vacuum shelf dryer and recrystallized from isopropyl alcohol. 43.3 g (62% of theory) of the title compound is obtained as white powder. Analysis: Calculated: C 56.71 H 5.48 N 8.016 S 13.76 Found: C 56.90 H 5.31 N 8.00 S 13.59 b) 13-methoxy-3,6,9,15-tetraazabicyclo[9.3.1]pentadeca-1(15),11,13-triene 30 g (42.9 mmol) of the title compound from example 18a is stirred with 100 ml of concentrated sulfuric acid for 24 hours at 95 ° C. After cooling to 0° C., 400 ml of ether is instilled, it is suctioned from the precipitate formed and dissolved in 60 ml of 40% sodium hydroxide solution. The solution is extracted five times with 75 ml of dichloromethane each, dried on magnesium sulfate and concentrated by evaporation in a vacuum. The residue is recrystallized from diisopropyl ether and 6.59 g (65% of theory) of the title compound is obtained as white powder. Analysis: Calculated: C 60.99 H 8.53 N 23.71 Found: C 61.15 H 8.40 N 23.52 c) 13-methoxy-3,6,9-tris-(carboxymethyl)-3,6,9,15-tetraazabicyclo[9.3.1]pentadeca-1(15),11,13-triene 6.2 g (26.2 mmol) of the title compound from example 18b is dissolved in 40 ml of water, mixed with 9.90 g (104.8 mmol) of chloroacetic acid. By addition of 6N potassium hydroxide solution a pH of 9.5 is adjusted and it is heated for 8 hours to 45°–50° C. During this time the pH is maintained at 9.5–10 by addition of further potassium hydroxide solution. It is then cooled in an ice bath, mixed with concentrated hydrochloric acid up to a pH of 2. A precipitate is formed, suctioned off, the residue is dissolved in 80 ml of water under low heat and the solution is adsorbed on a cation exchanger column (IR 120). The column is first eluted with abundant water, then with 0.5N ammonia solution. The basic eluate is gathered and concentrated by evaporation in a vacuum. The residue is dissolved in 80 ml of water and the solution is adsorbed on an anion exchanger column (IRA 67). At first it is eluted with water, then with 0.5N formic acid. The acid fraction is concentrated by evaporation in a vacuum, the residue is dissolved in methanol and by addition of acetone the title compound precipitates. 7.42 g (69% of theory) is obtained as white powder. Analysis: Calculated: C 52.68 H 6.39 N 13.65 Found: C 52.81 H 6.22 N 13.80 d) Gadolinium complex of 13-methoxy-3,6,9-tris(carboxymethyl)-3,6,9,15-tetraazabicyclo[9.3.1]pentadeca-1(15),11,13-triene 5 g (12.18 mmol) of the title compound from example 18c is heated with 2.21 g (6.09 mmol) of gadolinium oxide in 60 ml of water for 4 hours to 85°–90° C. The solution is filtered and freeze-dried. 6.74 g (98% of theory) of the title compound is obtained as white amorphous powder. Water content 4.7%. Analysis: Calculated: C 38.29 H 4.10 Gd 27.85 N 9.92 Found: C 38.41 H 3.92 Gd 27.60 N 9.99 (water content taken into account in the calculation)

Example 19 a) 13-chloro-3,6,9-tris-(tert.-butoxycarbonylmethyl)-3,6,9,15-tetraazabicyclo[9.3.1]pentadeca-1(15),11,13-triene 18.72 g (95.96 mmol) of bromoacetic acid-tert.-butylester is added to 7 g (29.08 mmol) of the title compound from example 5c and 10.17 g (95.96 mmol) of sodium carbonate in 200 ml of acetonitrile, and is stirred for 24 hours at room temperature.

It is concentrated by evaporation in a vacuum, the residue is taken up with 300 ml of water and is extracted three times with 200 ml of methylene chloride. After drying of the organic phases on magnesium sulfate, it is concentrated by evaporation in a vacuum and the remaining oil is chromatographed on silica gel (mobile solvent: methylene chloride/ethanol=15/1).

Yield: 14.08 g (83% of theory) of a colorless oil. Analysis: Calculated: C 59.73 H 8.12 N 9.61 O 16.46 Cl 6.08 Found: C 59.67 H 8.25 N 9.58 Cl 6.01 b) 13-(N-pyrrolidino)-3,6,9-tris-(tert.-butoxycarboxymethyl)-3,6,9,15-tetraazabicyclo[9.3.1]pentadeca-1(15),11,13-triene 1.11 g (46.3 mmol) of sodium hydride (previously washed with pentane) is carefully added to 13.5 g (23.15 mmol) of the title compound from example 19a and 3.94 g (46.3 mmol) of pyrrolidinone and 612 mg (2.32 mmol) of 18-crown-6 in 200 ml of anhydrous dimethylformamide. It is stirred for 72 hours at 70° C. under nitrogen. The solution is cooled to room temperature and poured into 1.2 l of ice water. Then it is extracted three times with 250 ml of ethyl acetate. The organic phase is dried on magnesium sulfate and concentrated by evaporation in a vacuum. The residue is chromatographed on silica gel (mobile solvent: methylene chloride/methanol: 13/1).

Yield: 5.7 g (39% of theory) of a colorless oil, which crystallizes when allowed to stand. Analysis: Calculated: C 62.73 H 8.45 N 11.09 O 17.73 Found: C 63.68 H 8.54 N 11.01 c) 13-(N-pyrrolidino)-3,6,9-tris-(carboxymethyl)-3,6,9,15-tetraazabicyclo[9.3.1]pentadeca-1(15),11,13-triene 5.1 g (8.07 mmol) of the title compound from example 19b is dissolved in 50 ml of trifluoroacetic acid and stirred for 6 hours at room temperature. The solvent is removed in a vacuum and is purified, as described in example, 1d on an anion exchanger.

Crystallization from MeOH/acetone yields 2.88 g (77% of theory) of a strongly hygroscopic substance. Analysis: Calculated: C 54.42 H 6.31 N 15.11 O 24.17 Found: C 54.37 H 6.42 N 15.05 d) Gadolinium complex of 13-(N-pyrrolidino)-3,6,9-tris-(carboxymethyl)-3,6,9,15-tetraazabicyclo[9.3.1]pentadeca-1(15),11,13-triene 2.5 g (5.4 mmol) of the title compound from example 19c is dissolved in 20 ml of deionized water and 978 mg (2.7 mmol) of gadolinium oxide is added. It is stirred for 3 hours at 90° C. The solution is filtered and the filtrate is freeze-dried.

Yield: 3.32 g (100% of theory) of an amorphous powder, which according to analysis contains 13.2% water. Analysis: Calculated: C 40.83 H 4.24 N 11.34 O 18.13 Gd 25.46 Found: C 40.74 H 4.37 N 11.28 Gd 25.41

Example 20 a) 13-azido-3,6,9-tris-(tert.-butoxycarbonylmethyl)-3,6,9,15-tetraazabicyclo[9.3.1]pentadeca-1(15),11,13-triene 21 g (36.01 mmol) of the title compound from example 19a is dissolved in 200 ml of dimethylformamide and 7.02 g (108 mmol) of sodium azide as well as 951 mg (3.6 mmol) 18-crown-6 is added. It is stirred for 24 hours at 90° C.

After cooling to room temperature it is poured into 1.5 l of ice water and extracted three times with 200 ml of ethyl acetate. After drying of the organic phase on magnesium sulfate, it is concentrated by evaporation and the remaining oil is chromatographed on silica gel (mobile solvent: methylene chloride/ethanol=15/1).

Yield: 10.83 g (51% of theory) of a pale yellow oil. Analysis: Calculated: C 59.06 H 8.03 N 16.63 O 16.28 Found: C 59.17 H 8.05 N 16.51 b) 13-amino-3,6,9-tris-(tert.-butoxycarboxymethyl)-3,6,9,15-tetraazabicyclo[9.3.1]pentadeca-1(15),11,13-triene 10 g (16.96 mmol) of the title compound from example 20a is dissolved in 400 ml of ethanol and 1 g of Pearlman catalyst (20% palladium hydroxide on carbon) is added. After 24 hour hydrogenation at normal pressure the catalyst is suctioned off and concentrated by evaporation in a vacuum. The remaining oil is chromatographed on silica gel (mobile solvent: methylene chloride/methanol/triethylamine=10/1/0.05). 8.89 g (93% of theory) of a slightly yellowish oil is obtained. Analysis: Calculated: C 61.78 H 8.76 N 12.42 O 17.03 Found: C 61.67 H 8.91 N 12.35 c) 13-amino-3,6,9-tris-(carboxymethyl)-3,6,9,15-tetraazabicyclo[9.3.1]pentadeca-1(15),11,13-triene 8.2 g (14.55 mmol) of the title compound from example 20b is dissolved in 100 ml of trifluoroacetic acid and stirred for 6 hours at room temperature. After evaporation of the solvent in a vacuum the residue is dissolved in 100 ml of water and poured onto a column filled with poly(4-vinyl-pyridine). After concentration by evaporation in a vacuum and crystallization from methanol/acetone, 5.24 g (91% of theory) of a strongly hygroscopic solid is obtained. Analysis: Calculated: C 51.64 H 6.37 N 17.71 O 24.28 Found: C 51.74 H 6.31 N 17.63 d) Gadolinium complex of 13-amino-3,6,9-tris-(carboxymethyl)-3,6,9,15-tetraazabicyclo[9.3.1]pentadeca-1(15),11,13-triene 4.8 g (12.14 mmol) of the title compound from example 20c is dissolved in 35 ml of deionized water and 2.2 g (6.07 mmol) of gadolinium oxide is added. It is stirred for 3 hours at 90° C. and the pH is maintained at 5.5 by addition of acetic acid. The solution is filtered and poured onto a column filled with poly(4-vinyl-pyridine). After treatment with activated carbon it is again filtered and freeze-dried.

Yield: 6.07 g (91% of theory) of an amorphous powder, which according to analysis contains 12.1% water. Analysis: Calculated: C 37.15 H 4.06 N 12.74 O 17.47 Gd 28.61 Found: C 37.08 H 4.17 N 12.68 Gd 28.54

Example 21 a) 13-(hydroxyacetamido)-3,6,9-tris-(tert.-butoxycarbonylmethyl)-3,6,9,15-tetraazabicyclo[9.3.1]pentadeca-1(15),11,13-triene 5.8 g (10.28 mmol) of the title compound from example 20b, 861 mg (11.32 mmol) of glycolic acid and 1.53 g (11.32 mmol) of 1-hydroxy-1H-benzotriazol hydrate are dissolved in 20 ml of absolute dimethylformamide and cooled to 0° C. 2.36 g (11.32 mmol) of dicyclohexylcarbodiimide is added and it is stirred for 1 hour at 0° C.; then overnight at room temperature. The solution is poured into 150 ml of ice water and extracted three times with 150 ml of ethyl acetate. After drying of the organic phase on magnesium sulfate, it is concentrated by evaporation in a vacuum. The residue is chromatographed on silica gel (mobile solvent: methylene chloride/methanol=10/1).

Yield: 2.88 g (45% of theory) of a colorless solid.
Analysis: Calculated: C 59.88 H 8.27 N 11.26 O 20.59
Found: C 59.76 H 8.35 N 11.31 b)
13-(hydroxyacetamido)-3,6,9-tris-(carboxymethyl)-3,6,9,15-tetraazabicyclo[9.3.1]pentadeca-1(15),11,13-triene 2.7 g (4.34 mmol) of the title compound from example 21a is dissolved in 40 ml of trifluoroacetic acid and stirred for 6 hours at room temperature. It is concentrated by evaporation in a vacuum and the residue is purified as described in example 1d on an anion exchanger.

Crystallization from isopropanol yields 1.56 (79% of theory) of a white powder. Analysis: Calculated: C 50.32 H 6.00 N 15.45 O 28.23 Found: C 50.24 H 6.07 N 15.49 c) Gadolinium complex of 13-(hydroxyacetamido)-3,6,9-tris-(carboxymethyl)-3,6,9,15-tetraazabicyclo[9.3.1]pentadeca-1(15),11,13-triene 1.45 g (3.2 mmol) of the title compound from example 21 b is dissolved in 10 ml of deionized water and 580 mg (1.6 mmol) of gadolinium oxide is added. It is stirred for 3 hours at 90° C. The solution is filtered and the filtrate is freeze-dried.

Yield: 1.94 g (100% of theory) of an amorphous powder, which according to analysis contains 11.5% water.
Analysis: Calculated: C 37.55 H 3.98 N 11.53 O 21.06 Gd 25.88 Found: C 37.48 H 4.11 N 11.48 Gd 25.79

Example 22 a)
13-chloro-3,6,9-tris-(p-tolylsulfonyl)-3,6,9-triazabicyclo[9.3.1]pentadeca-1(15),11,13-triene 182.85 g (300 mmol) of N,N',N''-tris(p-tolylsulfonyl)-diethylenetriamine-N,N''-disodium salt is dissolved in 2.4 l of dimethylformamide and heated to 100° C. To this a solution of 63.15 g (300 mmol) of 4-chloro-2,6-bis(chloromethl)pyridine in 1 liter of dimethylformamide is instilled. It is stirred overnight at 100° C.

Into the still hot solution 3 l of water is instilled and it is cooled to room temperature. The precipitate is washed with much water and dried in a vacuum (60° C.). Crystallization from acetonitrile yields 128.7 g (61% of theory) of the title compound as a colorless powder. Analysis: Calculated: C 54.65 H 5.02 N 7.97 O 13.65 S 13.68 Cl 5.04 Found: C 54.61 H 5.13 N 7.91 S 13.65 Cl 5.09 b)
13-(N-morpholino)-3,6,9-tris-(p-tolylsulfonyl)-3,6,9triazabicyclo[9.3.1]pentadeca-1(15),11,13-triene 126 g (179 mmol) of the title compound from example 22a is dissolved in 500 ml of dimethyl sulfoxide and 87.12 g (1 mol) of morpholine is added. The solution is stirred in an autoclave for 48 hours at 140° C. and 10 bars. It is cooled off, poured on 3 liters of ice water and the precipitate is suctioned off. After drying in a vacuum at 60° C., it is recrystallized from acetone. 87.72 g (65% of theory) is obtained as cream-colored powder.
Analysis: Calculated: C 57.32 H 5.75 N 9.29 O 14.86S 12.76 Found: C 57.32 H 5.84 N 9.18 S 12.82 c)
13-(N-morpholino)-3,6,9,15-tetraazabicyclo[9.3.1]pentadeca-1(15),11,13-triene 86 g (114 mmol) of the title compound from example 22b is added into 270 ml of concentrated sulfuric acid and stirred for 48 hours at 100° C. It is cooled to 0° C. and 1.35 l of absolute ether is instilled. The precipitate is suctioned off and suspended in 100 ml of aqueous sodium hydroxide solution (pH 12). It is extracted 7 times with 150 ml of chloroform and the combined organic phases are dried on magnesium sulfate. After concentration by evaporation in a vacuum 22.26 g (67% of theory) of a yellowish oil is obtained, which crystallizes when allowed to stand. Analysis: Calculated: C 61.82 H 8.65 N 24.04 O 5.49 Found: C 61.89 H 8.59 N 24.13 d)
13-(N-morpholino)-3,6,9-tris-(carboxymethyl)-3,6,9,15tetraazabicyclo[9.3.1]pentadeca-1(15),11,13-triene 10 g (34.3 mmol) of the title compound from example 22c is dissolved in 150 ml of water and 12.85 g (136 mmol) of chloroacetic acid is added. It is adjusted to pH 9.5 with 6 n potassium hydroxide solution. It is stirred for 12 hours at 45° C. and the pH is maintained between 9.5–10 by addition of 6 n potassium hydroxide solution. It is adjusted to pH 2 with concentrated hydrochloric acid and is purified on ion exchangers as described in example 1d. Crystallization from methanol/acetone yields 9.9 g (62% of theory) of the title compound as a strongly hygroscopic solid. Analysis: Calculated: C 54.18 H 6.71 N 15.05 O 24.06 Found: C 54.09 H 6.82 N 15.01 e) Gadolinium complex of 13-(N-morpholino)-3,6,9-tris-(carboxymethyl)-3,6,9,15-tetraazabicyclo[9.3.1]pentadeca-1(15),11,13-triene 9 g (19.33 mmol) of the title compound from example 22d is dissolved in 60 ml of deionized water and 3.5 g (9.67 mmol) of gadolinium oxide is added. It is stirred for 3 hours at 90° C. and the pH is maintained at 5.5 by addition of acetic acid. The solution is filtered and poured onto a column filled with poly) 4-vinyl-pyridine). After treatment with activated carbon it is again filtered and freeze-dried.

Yield: 10.9 g (91% of theory) of an amorphous powder, which according to analysis contains 9.87 % water.
Analysis: Calculated: C 40.70 H 4.55 N 11.30 O 18.07 Gd 25.37 Found: C 40.63 H 4.64 N 11.25 Gd 25.28

Example 23 a)
13-chloro-3,6,9-tris-(benzyl)-3,6,9,15-tetraazabicyclo[9.3.1]pentadeca-1(15),11,13-triene 9.3 g (38.62 mmol) of the title compound from example 5c and 21.36 g (154.5 mmol) of potassium carbonate is dissolved in 200 ml of dimethylformamide and heated to 70° C. Within 30 minutes 26.43 g (154.5 mmol) of benzyl bromide is instilled and stirred for 24 hours at 70° C.

The solvent is removed in a vacuum and the residue is taken up in 250 ml of 3 n potassium hydroxide solution. It is extracted 5 times with 150 ml of methylene chloride and the organic phases are dried on magnesium sulfate. After concentration by evaporation in a vacuum it is chromatographed on silica gel (mobile solvent: isopropanol/triethylamine=20/1).

Yield: 17.97 g (91% of theory) of a slightly yellow oil. Analysis: Calculated: C 75.20 H 6.90 N 10.97 Cl 6.93 Found: C 75.11 H 6.98 N 10.85 Cl 7.06 b)
13-carboxy-3,6,9-tris-(benzyl)-3,6,9,15-tetraazabicyclo[9.3.1]pentadeca-1(15),11,13-triene A solution of 17.5 g (34.24 mmol) of the title compound from example 23a in 80 ml of 1,2-dimethoxyethane is instilled into 1.95 g (79.44 mmol) of magnesium chips and heated to boiling. To this a solution of 6.43 g (34.24 mmol) of 1,2-dibromoethane in 40 ml of 1,2-dimethoxyethane is instilled over a period of 12 hours.

It is cooled in an ice bath and the solution is carefully poured on 10 g of dry ice. After 3 hours stirring at room temperature 200 ml of water is carefully added and it is brought to pH 4 with hydrochloric acid. It is evaporated to dryness and the residue is boiled out with 200 ml of ethanol. After filtering out the magnesium salts, it is again evaporated to dryness and the residue is again chromatographed on silica gel (mobile solvent: chloroform/methanol/triethylamine=20/15/1).

Yield: 5.16 g (29% of theory) of a slightly yellow solid. Analysis: Calculated: C 76.27 H 6.79 N 10.78 O 6.16 Found: C 76.19 H 6.88 N 10.71 c)
13-(morpholinocarbonyl)-3,6,9-tris-(benzyl)-3,6,9,15tetraazabicyclo[9.3.1]pentadeca-1(15),11,13-triene 5.0 g (9.62 mmol) of the title compound from example 23b, 922 mg (10.58 mmol) of morpholine and 1.43 g (10.58 mmol) of 1-hydroxy-1H-benzotriazol hydrate are dissolved in 10 ml of absolute dimethylformamide and cooled to 0° C. 2.18 g (10.58 mmol) of dicyclohexylcarbodiimide it is added and it is stirred for 1 hour at 0° C.; then overnight at room temperature.

The solution is poured in 180 ml of ice water and extracted 3 times with 150 ml of chloroform. After drying of the organic phase on magnesium sulfate it is concentrated by evaporation in a vacuum. The residue is chromatographed on silica gel (mobile solvent: chloroform/methanol/triethylamine=20/5/1).

4.22 g (88% of theory) of the title compound is obtained as colorless oil. Analysis: Calculated: C 75.48 H 7.19 N 11.90 O 5.44 Found: C 75.37 H 7.27 N 11.83 d)
13-(morpholinocarbonyl)-3,6,9,15-tetraazabicyclo[9.3.1]pentadeca-1(15),11,13-triene 4.1 g (6.96 mmol) of the title compound from example 23c is dissolved in 250 ml of ethanol and 0.5 g of Pearlman catalyst (20% palladium hydroxide on carbon) is added. After 24 hour hydrogenation in the autoclave (50° C. and 3 bars of hydrogen pressure) it is suctioned off from catalyst and concentrated by evaporation in a vacuum. The residue is recrystallized from 30 ml of tetrahydrofuran.

Yield: 1.85 g (83% of theory) of the title compound as white crystalline powder. Analysis: Calculated: C 60.16 H 7.89 N 21.93 O 10.02 Found: C 60.08 H 7.97 N 21.81 e)
13-(morpholinocarbonyl)-3,6,9-tris-(carboxymethyl)-3,6,9,15-tetraazabicyclo[9.3.1]pentadeca-1(15),11,13-triene 1.5 g (5.0 mmol) of the title compound from example 23d is dissolved in 25 ml of water and 1.89 g (20 mmol) of chloroacetic acid is added. It is adjusted to pH 9.5 with 6 n potassium hydroxide solution. It is stirred for 12 hours at 45° C. and the pH is maintained between 9.5-10 by addition of 6 n potassium hydroxide solution.

After working up an ion exchangers as described in example 1d, after crystallization from methanol/acetone 1.66 g (67% of theory) of a strongly hygroscopic solid is obtained. Analysis: Calculated: C 53.54 H 6.33 N 14.19 O 25.94 Found: C 53.41 H 6.47 N 14.08 f) Gadolinium complex of 13-(morpholinocarbonyl)-3,6,9-tris(carboxymethyl)-3,6,9,15-tetraazabicyclo[9.3.1]pentadeca-1(15),11,13-triene 1.5 g (3.04 mmol) of the title compound from example 23e is dissolved in 10 ml of deionized water and 551 mg (1.52 mmol) of gadolinium oxide is added. It is stirred for 3 hours at 90° C. The solution is filtered and the filtrate is freeze-dried.

Yield: 1.97 g (100% of theory) of a white amorphous powder which according to analysis contains 10.1% water. Analysis: Calculated: C 40.79 H 4.36 N 10.81 O 19.76 Gd 24.28 Found: C 40.71 H 4.44 N 10.89 Gd 24.17

Example 24: NMR diagnosis in vivo

To a naked mouse Balb/c nu/nu, female, 20 g, with subcutaneous HT 29 colon carcinoma, after previous shots in the nuclear spin tomograph (producer: General Electric, 2 tesla) 0.1 mmol of gadolinium complex of 3,6,9-tris(carboxymethyl)-3,6,9,15-tetraazabicyclo[9.3.1]pentadeca-1(15),11,13-triene [example 1e] per kg is applied i.v. in a caudal vein. The substance was dissolved in bi-distilled water (pH 7.2). Shots were taken in spin-echo-sequence $T_R=400$ msec., $T_E=30$ msec.

The shots were taken before and also 1, 23 and 43 minutes after application of the contrast medium in the area of the liver and of the tumor.

It was possible to show that the signal intensity in the tumor increased and did not fall again over the observed period.

Example 25

(a) 3,6,9-Tris[dihydro,2 (3H)-furanon-3-yl]-3,6,9,15-tetraazabicyclo [9.3.1]pentadeca-1(15),11,13-triene 40 g (242.38 millimoles) of α-bromo-γ-butyrolactone is added to 10 g (48.48 mmol) of 3,6,9,15-tetraazabicyclo [9.3.1]pentadeca-1(15),11,13-triene, 33.5 g (242.38 mmol) of potassium carbonate and 805 mg (4.85 mmol) of potassium iodide in 200 ml of acetonitrile. This mixture is heated under reflux for 48 hours, evaporated to dryness under vacuum, and the residue is taken up in 500 ml of methylene chloride and extracted three times with 150 ml of water. The organic phase is dried over magnesium sulfate and evaporated under vacuum. The residue is purified by chromatography, on silica gel. (Mobile phase: methylene chloride/methanol=15:1)

Yield: 7.11 g (32% of theory) of a slightly yellow-colored oil which solidifies when allowed to stand. Analysis: C 60.25 H 6.59 N 12.22 (Calcd.) C 60.18 H 6.64 N 12.17 (Found)

(b) Gadolinium Complex of 3,6,9,15-Tetraazabicyclo]9.3.1]pentadeca-1(15),11,13-triene-3,6,9-tris-[α-(2-hydroxyethyl)acetic Acid]

6.7 g (14.61 mmol) of the title compound of Example 25(a) is dissolved in 50 ml of deionized water, and the pit is brought to 5.5 by adding 1-normal hydrochloric acid. To this mixture is added 2.65 g (7.3 mmol) of gadolinium oxide and the mixture is refluxed for 3 hours. The cooled solution is stirred for one hour with respectively 10 ml of acidic ion exchanger (IR 120) and 10 ml of alkaline ion exchanger (IRA 410). The mixture is filtered off from the exchanger, and the filtrate is boiled for one hour with active carbon. After filtration and freeze-drying, 9.25 g (95% of theory) of an amorphous, colorless powder is obtained (containing 8.3% of water per analysis).

Analysis (corrected for water): C 41.43 H 4.99 N 8.40 Gd 23.58 (Calcd.) C 41.35 H 5.09 N 8.34 Gd 23.50 (Found)

(c) Europium Complex of 3,6,9,15-Tetraazabicyclo[9.3.1]pentadeca-1(15),11,13-triene-3,6,9-tris[α-(2-hydroxyethyl)acetic Acid]

Analogously, the corresponding Europium complex is obtained with $^{151}Eu_2O_3$.

Analysis (corrected for water): C 41.76 H 5.03 N 8.47 Eu 22.97 (Calcd.) C 41.68 H 5.12 N 8.39 Eu 22.88 (Found)

Example 26

(a) 3,6,9,15-Tetraazabicyclo[9.3.1]pentadeca-1(15),11,13-triene-3,6,9-tris[α-(benzyloxymethyl)acetic Acid]

10 g (48.48 mmol) of 3,6,9,15-tetraazabicyclo[9.3.1-]pentadeca-1(15),11,13-triene and 114.71 g (484.8 mmol) of the sodium salt of 2-chloro-3-benzyloxypropionic acid in 200 ml of water are heated to 70° C. for 48 hours. The solution is diluted with 400 ml of water and 300 ml of 2N hydrochloric acid is added thereto. The mixture is extracted 5 times with respectively 200 ml of methylene chloride. The aqueous phase is evaporated under vacuum. The residue is dissolved in 300 ml of ethanol and filtered off from the sodium chloride. Then the mixture is evaporated under vacuum and the remaining oil is chromatographed on silica gel (mobile phase: ethanol/water=20:1). The main fractions are evaporated under vacuum and dissolved in 50 ml of 5% strength hydrochloric acid. The solution is passed over a column, filled with "Reillex" (=poly-4-vinylpyridine), and the product is eluted with a mixture of water/methanol 3:1. After evaporation of the main fractions, 12.93 g (36% of theory) of a strongly hygroscopic solid is obtained (9.1% water per analysis).

Analysis (corrected for water): C 66.47 H 6.53 N 7.56 (Calcd.) C 66.38 H 6.60 N 7.48 (Found)

(b) 3,6,9,15-Tetraazabicyclo[9.3.1]pentadeca-1(15),11,13-triene-3,6,9-tris[α-(hydroxymethyl)acetic Acid]

12.6 g (17.01 mmol) of the title compound of Example 26(a) is dissolved in a mixture of 200 ml of methanol/100 ml of water, and 4 g of palladium catalyst is added (10% Pd on active carbon). The mixture is hydrogenated for 5 hours at 50° C., filtered off from the catalyst, and evaporated under vacuum. Yield: 7.84 g (98% of theory) of a vitreous solid (6.9% water per analysis). Analysis (corrected for water): C 51.06 H 6.43 N 11.91 (Calcd.) C 50.97 H 6.51 N 11.81 (Found )

(c) Gadolinium Complex of 3,6,9,15-Tetraazabicyclo-[9.3.1]pentadeca-1(15),11,13-triene-3,6,9-tris[α-(hydroxymethyl)acetic Acid]

7.5 g (15.94 mmol) of the title compound of Example 26(b) is dissolved in 50 ml of deionized water, and 2.89 g (7.97 mol) of gadolinium oxide is added. The mixture is heated for 3 hours at 90° C. The cooled solution is stirred for one hour at room temperature with respectively 2 ml of acidic ion exchanger (IR 120) and 2 ml of alkaline exchanger (IRA 410), filtered off from the exchanger, and the filtrate is briefly boiled with active carbon. After filtration and freeze-drying, 9.56 g (96% of theory) of a colorless, amorphous powder is obtained (8.1% water per analysis). Analysis (corrected for water): C 38.45 H 4.36 N 8.97 Gd 25.17 (Calcd.) C 38.37 H 4.43 N 8.89 Gd 25.06 (Found)

Example 27

(a) 3,6,9,15-Tetraazabicyclo[9.3.1]pentadeca-1(15),11,13-triene-3,6,9-tris[α-(1,2-O-isopropylidene-1,2-dihydroxyethyl)acetic Acid Ethyl Ester]

A mixture of 15 g (72.71 mmol) of 3,6,9,15-tetraazabicyclo[9.3.1]pentadeca-1(15),11,13-triene, 156.38 g (426.28 mmol) of 3,4-O-isopropylidene-2-(p-tolylsulfonyl)-3,4-dihydroxybutyric acid ethyl ester, 60.3 g (436.28 mmol) of potassium carbonate, and 2.41 g (14.54 mmol) of potassium iodide in 400 ml of acetonitrile is heated under reflux for 48 hours. The mixture is evaporated under vacuum and the residue taken up in 500 ml of methylene chloride. The mixture is extracted 3 times with 200 ml of water and the organic phase is dried over magnesium sulfate. After evaporation, the remaining oil is chromatographed on silica gel (mobile phase: methylene chloride/hexane/methanol=20:4:1).

Yield: 17.24 g (31% of theory) of a yellow, viscous oil. Analysis: C 59.67 H 7.91 N 7.32 (Calcd.) C 59.59 H 7.98 N 7.27 (Found)

3,6,9,15-Tetraazabicyclo[9.3.1]pentadeca-1(15),11,13-triene-3,6,9-tris[α-(1,2-dihydroxyethyl)acetic Acid]

16.5 g (21.57 mmol) of the title compound of Example 27(a) is dissolved in 100 ml of ethanol, and 50 ml of 5N sodium hydroxide solution is added thereto. The mixture is heated under reflux for 10 hours and evaporated under vacuum. The residue is dissolved in 250 ml of methanol and filtered off from the sodium chloride. The filtrate is evaporated under vacuum and the residue purified on an ion exchanger as follows: The product is dissolved in 50 ml of water, and the solution is introduced into a cation exchange column (IR 120). After flushing with water, the ligand is eluted with 0.5N aqueous ammonia solution. The main fractions are evaporated, taken up in a small amount of water and passed over an ion exchange column (IRA 67). The product is first washed with water and then eluted with 0.5N formic acid. The mixture is evaporated under vacuum and the residue dissolved in a small quantity of hot methanol. By the gentle addition of acetone and cooling in an ice bath, the title compound is obtained in crystalline form.

Yield: 8.22 g (68% of theory) of a vitreous solid (9.2% water per analysis). Analysis (corrected for water): C 49.28 H 6.47 N 9.99 (Calcd.) C 49.17 H 6.56 N 9.88 (Found )

(c) Gadolinium Complex of 3,6,9,15-Tetraazabicyclo-[9.3.1]pentadeca-1(15),11,13-triene-3,6,9-tris-[α-(1,2-dihydroxyethyl)acetic Acid]

8 g (14.27 mmol) of the title compound of Example 27(b) is dissolved in 60 ml of deionized water, and 2.58 g (7.135 mmol) of gadolinium oxide is added. The mixture is heated for 3 hours at 90° C. The cooled solution is stirred for one hour at room temperature with respectively 2 ml of acidic ion exchanger (IR 120) and 2 ml of alkaline exchanger (IRA 410). The mixture is removed from the exchanger by filtration and the filtrate boiled with active carbon. After filtration and freeze-drying, 9.89 g (97% of theory) of a colorless, amorphous powder is obtained (containing 7.3% water per analysis).

Analysis (corrected for water): C 38.65 H 4.65 N 7.84 Gd 22.00 (Calcd.) C 38.54 H 4.74 N 7.78 Gd 21.92 (Found)

Example 28

(a) 2,2',6,6'-Tetra(hydroxymethyl)-4,4'-bipyridine 50 g (128.77 mmol) of 2,2',6,6'-tetra(methoxycarbonyl)-4,4'-bipyridine is dissolved in a mixture of 400 ml of dioxane/400 ml of water and, in portions, 48.71 g (1.28 mol) of sodium borohydride is added thereto. The mixture is stirred overnight at room temperature. The solution is acidified with 5N hydrochloric acid and evaporated to dryness. The residue is suspended in 1 liter of 1N sodium hydroxide solution and extracted three times with 250 ml of chloroform. The organic phases are dried over magnesium sulfate and evaporated under vacuum. The residue is recrystallized from ethanol/ether.

Yield: 29.53 g (83% of theory) of colorless crystals.
Analysis: C 60.86 H 5.84 N 10.14 (Calcd.) C 60.77 H 5.93 N 10.06 (Found)

(b) 2,2',6,6'-Tetra(chloromethyl)-4,4'-bipyridine 29 g (104.96 mmol) of the title compound of Example 28(a) is heated under reflux for 5 hours in 250 g (2.1 mol) of thionyl chloride. The mixture is evaporated to dryness and the residue taken up in 200 ml of concentrated soda solution. The mixture is extracted twice with 150 ml of methylene chloride. The organic phase is dried over magnesium sulfate and evaporated under vacuum. The residue is crystallized from ether/hexane.

Yield: 35.54 g (94% of theory) of colorless crystals.
Analysis: C 48.03 H 3.45 N 8.08 Gd 40.51 (Calcd.) C 48.10 H 3.40 N 7.96 Gd 40.59 (Found)

13,13'-Bis[3,6,9-tris(p-tolylsulfonyl)-3,6,9,15-tetraazabicyclo[9.3.1]pentadeca-1(15),11,13-triene]

At 100° C., a solution of 34 g (97.12 mmol) of the title compound of Example 28 (b) (dissolved in 700 ml of dimethylformamide) is adddded dropwise within 4 hours to 118.43 g (194.25 mmol) of N,N',N''-tris(p-tolylsulfonyl) diethylenetriamine-N,N''-disodium salt in 1600 ml of dimethylformamide. The mixture is stirred overnight at 100° C. Two liters of water are added dropwise to the hot solution, and the latter is allowed to cool down to 0° C. The precipitate is suctioned off and washed with water. After drying under vacuum (60° C.), the product is recrystallized from acetonitrile, thus obtaining 79.13 g (61% of theory) of a cream-colored powder.

Analysis: C 57.55 H 5.28 N 8.39 S 14.40 (Calcd.) C 57.47 H 5.35 N 8.13 S 14.32 (Found)

(d) 13,13'-Bis[3,6,9,15-tetraazabicyclo[9.3.1]pentadeca-1(15),11,13-triene] Octahydrosulfate 79 g (59.15 mmol) of the title compound of Example 28(c) is introduced into 270 ml of concentrated sulfuric acid and stirred for 48 hours at 100° C., then cooled to 0° C., and 1.35 l of absolute either is added dropwise. The precipitate is suctioned off and extracted by stirring in 500 ml of methanol. After the product has been filtered off and dried under vacuum, 65.74 g (93% of theory of a solid is obtained which deliquesces in the air.

Analysis: C 22.11 H 4.22 N 9.38 S 21.46 (Calcd.) C 22.04 H 4.33 N 9.29 S 21.38 (Found)

(e) 13,13'-Bis[3,6,9,15-tetraazabicyclo[9.3.1]pentadeca-1(15),11,13-triene]

65.5 g (54.80 mmol) of the title compound of Example 28(d) is dissolved in 100 ml of water and the pH is adjusted to 13 with 32% strength sodium hydroxide solution. The mixture is extracted three times with 250 ml of hot toluene. The combined toluene phases are heated under reflux for one hour with 20 g of finely pulverized sodium hydroxide. The mixture is filtered and the filtrate evaporated to dryness.

Yield: 21.6 g (96% of theory) of a solid having a slightly yellow color. Analysis: C 64.36 H 8.35 N 27.29 (Calcd.) C 64.27 H 8.44 N 27.22 (Found)

(f) 13,13'-Bis[3,6,9,15-tetraazabicyclo[9.3.1]pentadeca-1(15),11,13-triene-3,6,9-tris[α-(benzyloxymethyl)acetic Acid]]

21.5 g (52.37 mmol) of the title compound of Example 28(e) and 247.8 g (1.05 mol) of the sodium salt of 2-chloro-3-benzyloxypropionic acid in 400 ml of water are heated for 48 hours to 70° C. The solution is diluted with 800 ml of water and combined with 600 ml of 2N hydrochloric acid, then extracted 5 times with respectively 300 ml of methylene chloride, and the aqueous phase is evaporated under vacuum. The residue is dissolved in 500 ml of ethanol and filtered off from the sodium chloride. The mixture is evaporated under vacuum and the residue chromatographed on silica gel (mobile phase: ethanol/water=20:1). The main fractions are evaporated under vacuum and dissolved in 100 ml of 5% strength hydrochloric acid. The solution is passed over a column filled with "Reillex" (=poly-4-vinylpyridine), and the product is eluted with a mixture of water/methanol 2:1. After evaporation of the main fractions, 20.92 g (27% of theory) of a strongly hygroscopic solid is obtained (8.1% water per analysis).

Analysis (corrected for water): C 66.56 H 6.40 N 7.57 (Calcd.) C 66.47 H 6.51 N 7.48 (Found)

(g) 13,13'-Bis[3,6,9,15-tetraazabicyclo[9.3.1]pentadeca-1(15),11,13-triene-3,6,9-tris[α-(hydroxymethyl)acetic Acid]]

20.5 g (13.85 mmol) of the title compound of Example 28(f) is dissolved in a mixture of 300 ml of methanol/150 ml of water, and 7 g of palladium catalyst (10% Pd on active carbon) is added thereto. The mixture is hydrogenated for 5 hours at 50° C. The product is removed from the catalyst by filtration and evaporated under vacuum.

Yield: 12.62 g (97% of theory) of a vitreous solid (8.5% water per analysis). Analysis (corrected for water): C 51.17 H 6.23 N 11.93 (Calcd.) C 51.07 H 6.31 N 11.87 (Found)

(h) Gadolinium Complex of 13,13'-Bis[3,6,9,15-tetraazabicyclo[9.3.1]pentadeca-1(15),11,13-triene-3,6,9-tris [α-(hydroxymethyl) acetic Acid]]

12 g (12.78 mmol) of the title compound of Example 28(g) is dissolved in 80 ml of deionized water, and 4.63 g (12.78 mmol) of gadolinium oxide is added. The mixture is heated for 3 hours at 90° C. The drawn-off solution is stirred for one hour at room temperature with respectively 5 ml of acidic ion exchanger (IR 120) and 5 ml of alkaline exchanger (IRA 410). The product is filtered off from the exchanger, and the filtrate is briefly boiled with active carbon. After filtration and freeze-drying, 15.3 g (96% of theory) of a colorless, amorphous powder is obtained (containing 9.3% of water per analysis).

Analysis (corrected for water): C 38.52 H 4.20 N 8.98 Gd 25.21 (Calcd.) C 38.46 H 4.28 N 8.91 Gd 25.14 (Found)

Example 29

(a) Trans-5-(p-tolylsulfonyl)amino-6-(p-tolylsulfonyloxy)-2,2-dimethyl-1,3-dioxepane Under agitation, 295.67 g of p-toluenesulfochloride is added in portions at −5° to 0° C. to a solution of 100 g of trans-6-amino-2,3-dimethyl-1,3-dioxepan-5-ol in 903 ml of pyridine. The mixture is allowed to stand for 72 hours at +4° C. and then stirred into 10 l of ice water. After the precipitate has been suctioned off and washed with water, the residue is dried in a drying cabinet at 50° C. and 200 torr for 48 hours. For purposes of purification, the crude product is recrystallized from 5 l of dioxane, thus obtaining 196 g of the title compound as a white powder, mp 200°–202° C.

(b) Monosodium Salt of N-[2-(N-Tolylsulfonylamino)ethyl]-p-tolylsulfonamide 150 g of N-[2-(N-tolylsulfonylamino)ethyl]-p-tolylsulfonylamide is suspended in 1.25 l of ethanol, heated under reflux, and a solution of 10.3 g of sodium in 300 ml of ethanol is added dropwise thereto, thus forming a solution. During cooling, the title compound is precipitated, suctioned off, the precipitate washed with ethanol and dried at 50° C. and 200 torr. Yield: 119 g of the title compound as a white powder.

(c) cis-2,2-Dimethyl-5-[N-(p-tolylsulfonyl)amino]-6-N-(p-tolylsulfonyl)-N-(N'-2-p-tolylsulfonylaminomethyl)]-1,3-dioxepane 116 g of the monosodium salt of Example 29(b) is suspended in 2.66 l of dimethylformamide. At 100° C., a solution of 141 g of trans-5-(p-tolylsulfonyl)amino-6-(p-tolylsulfonyloxy) -2,2-dimethyl-1,3-dioxepane in 1.5 l of dimethylformamide is added dropwise thereto and the mixture is stirred for 5 hours at a bath temperature of 120° C. The reaction solution is then concentrated under vacuum to 1 liter and diluted with 10 l of ice water, suctioned off, the precipitate is washed with water and dried at 50° C. and 200 torr, and the product is 182 g of the crude title compound. For purification, the product is extracted by boiling with 1.85 l of ethanol. After suctioning off and drying, 125 g of the title compound is obtained as a white powder, mp 190°–194° C.

(d) Disodium Salt of cis-2,2-Dimethyl-5-[N-(p-tolylsulfonyl)amino]-6-[N-(p-tolylsulfonyl)-N-(N'-2-p-tolylsulfonylaminomethyl)]-1,3-dioxepane 87.8 g of the compound obtained according to Example 29(c) is suspended in 410 ml of ethanol, heated to boiling, and a solution of 6.67 g of sodium in 200 ml of ethanol is added dropwise thereto. The mixture is cooled in an ice bath, combined with 450 ml of ether, and suctioned off from the precipitate, which latter is dried at 80° C. and 200 torr, thus producing 91 g of the title compound as a white powder.

(e) Acetonide of 4,5-Bis(hydroxymethyl)-3,6,9-tritosylsulfonyl-3,5,9,15-tetraazabicyclo[9.3.1]pentadeca-1(15),11,13-triene 78.75 g of the disodium salt of Example 29(d) is dissolved in 880 ml of dimethylformamide, heated to 100° C., and a solution of 19.53 g of his (2,6-chloromethyl)-pyridine in 360 ml of dimethylformamide is added dropwise thereto; the mxiture is heated for 5 hours to 120° C. and concentrated under vacuum to 300 ml. The solution is stirred into 5 l of ice water, the precipitate is suctioned off, washed with water, and dried. The crude product is recrystallized from 700 ml of dioxane, thus obtaining 45 g of the title compound as a white powder, mp 244°–250° C.

(f) Acetonide of 4,5-Bis(hydroxymethyl)-3,6,9,15-tetraazabicyclo[9.3.1]pentadeca-1(15),11,13-triene A suspension of 20 g of the compound obtained according to Example 29(e) in 140 ml of tetrahydrofuran is added to 260 ml of liquid ammonia; the mixture is stirred in a refrigerating bath at −50° C., and a total of 14.4 g of sodium is introduced in portions. The mixture is stirred for another 5 hours at −60° C., then the refrigerating bath is removed, and 50 ml of ethanol is added dropwise. The ammonia is allowed to evaporate, the mixture is evaporated to dryness under vacuum, and the residue is purified by chromatography on silica gel. Elution with chloroform/ethanol/concentrated ammonia solution (3/1/0.5) yields 5.30 g of the title compound as an oil.

Analysis: C 62.72 H 8.55 N 18.29 (Calcd.) C 62.51 H 8.41 N 18.45 (Found)

(g) Acetonide of 4,5-Bis(hydroxymethyl)-3,6,9,15-tetraazabicyclo[9.3.1]pentadeca-1(15),11,13-triene-3,6,9-tris(acetic Acid tert-Butyl Ester)

5.51 g of anhydrous sodium carbonate and 10.2 g of bromoacetic acid tert-butyl ester are added to a solution of 4 g of the compound produced according to Example 29(f) in 100 ml of tetrahydrofuran and 10 ml of water and the mixture is stirred for 5 hours at 50° C. The mixture is filtered, evaporated under vacuum, and the oily residue is stirred with 50 ml of hexane and decanted. The residue is purified by chromatography on 100 g of silica gel with dichloromethane (1–10% ethanol), thus obtaining 5.7 g of the title compound as a light-yellow oil.

(h) 4,5-Bis(hydroxymethyl)-3,6,9,15-tetraazabicyclo[9.3.1]pentadeca-1(15),11,13-triene-3,6,9-tris-acetic Acid A mixture of 5.3 g of the ester prepared according to Example 29(g) and 50 ml of trifluoroacetic acid is stirred for 3 hours at 50° C. Then 10 ml of water is added, the mixture is stirred for another 2 hours at 50° C., and thereafter evaporated to dryness under vacuum. The residue is dissolved in 20 ml of water, and the solution is allowed to pass through a column with 100 ml of "Reillex" (poly-4-vinylpyridine), eluted with 100 ml of water, and the eluate is evaporated under vacuum, thus obtaining an amorphous powder which still contains 8.5% water.

Yield: 2.90 g. Analysis: C 51.81 H 6.41 N 12.72 (Calcd.) C 51.63 H 6.70 N 12.51 (Found)

(i) Gadolinium Complex of 4,5-Bis(hydroxymethyl)-3,6,9,15-tetraazabicyclo[9.3.19 pentadeca-1(15),11,13-triene-3,6,9-tris-acetic Acid 2 g (water content 8.5%, corresponding to 1.83 g=4.29 mmol) of 4,5-bis(hydroxymethyl)-3,6,9,15-tetraazabicyclo[9.3.1]pentadeca-1(15),11,13-triene-3,6,9-tris-acetic acid (production see Example 29(h) and 778 mg of gadolinium oxide are stirred for 5 hours with 50 ml of water at 90° C. After cooling, the mixture is stirred in succession with respectively 10 ml of anion exchanger IRA 410 and cation exchanger IRC 50, filtered, and the solution is subjected to freeze-drying, thus obtaining 2.35 g of the title compound as a loose white powder, water content, according to K.-Fischer titration: 7.3%.

Analysis (after correction for water content): $C_{19}H_{25}GdN_4O_8$ C 38.38 H 4.24 N 9.42 Gd 26.44 (Calcd.) C 38.51 H 4.31 N 9.36 Gd 26.19 (Found)

Example 30

(a) Acetonide of 4,5-Bis(hydroxymethyl)-3,6,9-tris-[dihydro-2-(3H)-furanon-3-yl]-3,6,9,15-tetraazabicyclo[9.3.1]pentadeca-1(15),11,13-triene A solution of 5 g (16.34 mmol) of acetonide of 4,5-bis(hydroxymethyl)-3,6,9,15-tetraazabicyclo[9.3.1]-pentadeca-1(15),11,13-triene in 100 ml of acetonitrile is combined with 12 g of potassium carbonate, 260 mg of potassium iodide and 13.50 g of α-bromo-γ-butyrolactone and heated for 48 hours to boiling. The mixture is then evaporated under vacuum, the residue is dissolved in methylene chloride, shaken several times with water, the organic phase is dried over sodium sulfate, and evaporated to dryness. The oily residue is chromatographed with methylene chloride/methanol (15:1) on 150 g of silica gel, thus obtaining 5.3 g of the title compound as a light-yellow, viscous oil.

(b) 4,5-Bis(hydroxymethyl)-3,6,9,15-tetraazabicyclo[9.3.1]pentadeca-1(15),11,13-triene-3,6,9-tris [α-(2-hydroxyethyl)]acetic Acid 5 g of the compound produced according to Example 30 (a) is dissolved in 50 ml of water and adjusted to a pH of 2 by addition of hydrochloric acid. The mixture is heated for 5 hours under reflux, cooled to room temperature, and the solution is allowed to pass over a column with 10 g of "Reillex" (poly-4-vinylpyridine). The column is rinsed with 20 ml of water and the combined eluates are subjected to freeze-drying, thus obtaining 4.05 g of the title compound as a loose powder with a water content of 7.2%.

Analysis (after correction for the water content): $C_{25}H_{40}N_4O_{11}$ C 52.44 H 7.04 N 9.78 (Calcd.) C 52.61 H 7.33 N 9.62 (Found )

(c) Gadolinium Complex of 4,5-Bis(hydroxymethyl)-3,6,9,15-tetraazabicyclo[9.3.1]pentadeca-1(15),11,13-triene-3,6,9-tris[α-(2-hydroxyethyl)]acetic Acid 1.50 g (2.68 mmol) of 4,5-bis(hydroxymethyl)-3,6,9,15-tetraazabicyclo[9.3.1]pentadeca-1(15),11,13-triene-3,6,9-tris[α-(2-hydroxyethyl)]acetic acid is stirred in 25 ml of water with 487 mg of gadolinium oxide for 4 hours at 90° C. After cooling, the solution is stirred in succession with 5 mol of anion exchanger IRA 410 and 5 ml of cation exchanger INC 50, filtered, and subjected to freeze-drying, thus obtaining 1.69 g of the title compound as a white powder with a water content of 4.3%.

Analysis (after correction for the water content): $C_{25}H_{37}GdN_4O_{11}$ C 41.31 H 5.13 N 7.71 Gd 21.63 (Calcd.) C 41.07 H 5.33 N 7.61 Gd 21.89 (Found)

Example 31

(a) 4-Hydroxymethyl-3,6,9-tritosyl-3,6,9,15-tetraazabicyclo[9.3.1]pentadeca-1(15),11,13-triene A solution of 59.57 g of 3-aza-1-hydroxymethyl-1,3,5-tritosylpentadiamine (preparation see International Patent Application PCT/DE 88/00200, WO 88/08422, page 45) in 500 ml of dimethylformamide is combined, in portions, with 9.60 g of a 50% strength suspension of sodium hydride in mineral oil, and the mixture is heated for one hour to 80° C. To this solution is added dropwise 17.61 g of 2,6-bis(chloromethyl)pyridine dissolved in 150 ml of dimethylformamide, and the mixture is heated for 6 hours to 110° C. The mixture is concentrated under vacuum to about 220 ml, and 1 liter of water is added dropwise. The precipitate is suctioned off, washed with water, and dried overnight at 50° C. and 200 mbar. The crude product is recrystallized from 500 ml of ethanol and yields 45 g of the title compound as a yellow solid.

(b) 4-Hydroxymethyl-3,6,9,15-tetraazabicyclo[9.3.1]-pentadeca-1(15),11,13-triene 42 g of the compound obtained according to Example 31(a) is heated with 120 ml of concentrated sulfuric acid for 48 hours to 100° C. The mixture is cooled to 0° C., and 350 ml of diethyl ether is added dropwise. The salt of the title compound is thus precipitated. The mixture is suctioned off, the residue is dissolved in 100 ml of water and combined with 40 g of sodium hydroxide and extracted repeatedly with dichloromethane. The combined organic phases are dried over sodium sulfate and evaporated under vacuum, thus obtaining 13.3 g of the title compound as a viscous oil.

(c) 4-Hydroxymethyl-3,6,9,15-tetraazabicyclo[9.3.1]-pentadeca-1(15),11,13-triene-3,6,9-triacetic Acid 10 g of the amine prepared according to Example 31(b) is dissolved in 100 ml of water and combined with 13.21 g of chloroacetic acid. The mixture is stirred for 5 hours at 60° C., maintaining the pH during this time at 9.0 by addition of 10N sodium hydroxide solution. The mixture is cooled to 0° C., combined with 100 ml of ethanol, and acidified with concentrated hydrochloric acid to pH 1. The thus-formed precipitate is suctioned off, dissolved in 50 ml of water, and the solution is passed over a column with 30 ml of "Reillex" (poly-4-vinylpyridine), rinsed with 50 ml of water, the eluates are combined and subjected to freeze-drying. Yield: 16.8 g of the title compound as an amorphous powder with a water content of 9.3%. Analysis (after correction for the water content): $C_{18}H_{26}N_4O_7$ C 52.68 H 6.39 N 13.65 (Calcd.) C 52.49 H 6.54 N 13.81 (Found)

(d) Gadolinium Complex of 4-Hydroxymethyl-3,6,9,15-tetraazabicyclo[9.3.1]pentadeca-1(15),11,13-triene-3,6,9-triacetic Acid A solution of 2.3 g of 4-hydroxymethyl-3,6,9,15-tetraazabicyclo[9.3.1]pentadeca-1(15),11,13-triene in 30 ml of water is combined with 1.015 g of gadolinium oxide and heated for one hour to 90° C. The product is removed from a small amount of unreacted oxide by filtration, and the solution is allowed to run in succession over respectively 10 ml of anion exchanger IRA 410 and cation exchanger IRC 50, rinsed with 30 ml of water, and the combined eluates are subjected to freeze-drying. Yield: 3.05 g of the title compound as a powder with a water content of 7.5%. Analysis (after correction for the water content): C 38.29 H 4.11 N 9.92 Gd 27.85 (Calcd.) C 38.44 H 4.32 N 9.68 Gd 27.71 (Found)

Example 32

(a) 4-Benzyloxymethyl-3,6,9,15-tetraazabicyclo[9.3.1]-pentadeca-1(15),11,13-triene-3,6,9-triacetic Acid A solution of 10 g (=24.36 mmol) of 4-hydroxymethyl-3,6,9,15-tetraazabicyclo[9.3.1]pentadeca-1(15),11,13-triene-3,6,9-triacetic acid (prepared according to Example 7b) in 150 ml of dimethylformamide is combined with 0.5 g of potassium iodide, 4.17 g of benzyl bromide, and 5 g of sodium carbonate. The mixture is heated for 20 hours to 60° C., concentrated under vacuum, combined with 100 ml of water and 300 ml of ethanol, and the pH is set at 2 by addition of concentrated hydrochloric acid. The mixture is suctioned off from the precipitate, the precipitate is dissolved in 100 ml of water, and the solution is passed over a column with 50 g of "Reillex" (poly-4-vinylpyridine). The column is washed with 50 ml of water and the combined aqueous phases are subjected to freeze-drying, thus obtaining 8 g of the title compound as an amorphous powder.

Analysis: C 59.99 6.44 N 11.19 (Calcd.) C 59.71 6.49 N 11.38 (Found)

(b) Gadolinium Complex of 4-Benzyloxymethyl-3,6,9,15-tetraazabicyclo[9.3.1]pentadeca-1(15),11,13-triene-3,6,9-triacetic Acid 1.81 g of gadolinium oxide is added to a solution of 5 g of 4-benzyloxymethyl-3,6,9,15-tetraazabicyclo[9.3.1]pentadeca-1(15),11,13-triene-3,6,9-triacetic acid in 100 ml of water; the mixture is heated for 3 hours to 80°-90° C., filtered, and the solution is allowed to pass in succession over columns with respectively 15 ml of anion exchanger IRA 410 and cation exchanger IRC 50. The columns are rinsed with 75 ml of water, and the combined aqueous phases are subjected to freeze-drying, thus obtaining 5.85 g of the title compound as an amorphous powder, water content 7.4%.

Analysis (after correction for water content): C 45.86 H 4.46 N 8.56 Gd 24.02 (Calcd.) C 45.69 H 4.71 N 8.72 Gd 23.81 (Found)

Example 33

Gadolinium Complex of 3,6,9-Tetraazabicyclo[9.3.1]-pentadecane-3,6,9-tris [α-(hydroxymethyl) acetic Acid]

4.5 g (7.2 mmol) of the title compound of Example 26(c) is dissolved in 150 ml of deionized water and hydrogenated in an autoclave over a rhodium catalyst (5% Rh/C) at 30 bar and 40° C. After 12 hours, the product is filtered off from the catalyst and the filtrate is stirred with respectively 3 ml of cation exchanger (IR 120) and 3 ml of anion exchanger (IRA 410) for one hour. The product is removed from the exchanger by filtration and freeze-dried.

Yield: 4.18 g (92% of theory) of a colorless, amorphous powder (containing 6.7% water per analysis). Analysis (corrected for water): C 30.08 H 5.27 N 8.88 Gd 24.93 (Calcd.) C 30.01 H 5.34 N 8.78 Gd 24.83 (Found)

Example 34

Preparation of a Solution of the Gadolinium(III) Complex of 3,6,9,15-Tetraazabicyclo[9.3.1]pentadeca-1(15),11,13-triene-3,6,9-tris [α-(2-hydroxyethyl)acetic Acid]

(a) 361 g (0.5 mole) of the complex obtained according to Example 25(b) (water content: 8.3%) is dissolved in 500 ml of water pro injectione (p.i.) with slight heating. After adding 0.8 g of tromethamine, the solution is filled up with water p.i. to 1000 ml. The solution is subjected to ultrafiltration and dispensed into bottles. After heat-sterilization, the solution is ready for use for diagnostic purposes by parenteral administration.

(b) The solution obtained by ultrafiltration according to Example 25(a) is filled under sterile conditions into multivials and lyophilized. After adding the desired amount of water p.i., the administration dose suitable for intrastitial injection for radiation therapy is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed:

1. A macrocyclic compound of general formula I

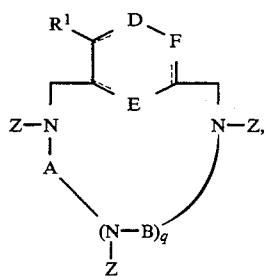

wherein represents a single bond or double bond;

q is 1 or 2;

A and B, being the same or different, are each a straight-chain or branched $C_{2-6}$-alkylene group;

D is N, =C=O, =NR$^2$, —CHR$^3$—, or =CR$^3$;

E is N, S, O,

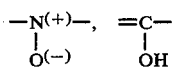

or NR$^4$;

F is (—CHR$^8$—)$_n$ or (=CR$^8$—)$_n$;

Z is H or —CH$_2$COOY;

Y is in each case H or a metal ion equivalent of an element with atomic numbers 21–29, 31, 32, 37–39, 42–44, 49 or 57–83;

R$^1$ is H, a halogen atom, or $C_1$-$C_6$-alkyl;

R$^2$ is H or $C_1$-$C_6$-alkyl;

R$^3$ is H, a halogen atom, phenyl, $C_1$-$C_6$-alkyl optionally substituted by one or more phenyl and/or hydroxy group(s), OR$^5$,

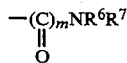

or G;

R$^4$ is a hydroxy group, H or $C_1$-$C_6$-alkyl, or $C_1$-$C_4$-alkyl optionally hydroxylated or carboxylated;

R$^5$ is $C_1$-$C_6$-alkyl optionally substituted by 1 to 3 hydroxy groups;

R$^6$ and R$^7$, independently from one another, are H, $C_1$-$C_4$-alkyl or $C_1$-$C_6$-alkyl substituted by 1 to 3 hydroxy groups, phenyl optionally substituted by 1 to 3 hydroxy groups, or benzyl optionally substituted by 1 to 3 hydroxy groups, or R$^6$ and R$^7$ together with the nitrogen atom form a saturated or unsaturated 5 or 6 member ring optionally containing an additional N atom, O atom, S atom or a carbonyl group, said 5 or 6 member ring being optionally substituted by 1 to 3 $C_1$-$C_6$-alkyl or $C_1$-$C_4$-alkyl substituted by 1 to 3 hydroxy groups, or one of the substituents R$^6$ or R$^7$ is

R$^8$ is H, a halogen atom, $C_1$-$C_4$-alkyl or G;

m is 0 or 1;

n is 0 or 1;

G is a second macrocycle of general formula II bonded by a direct bond, a bis(carbonylamino) group or by a $C_1$-$C_{20}$-alkylene group optionally having carbonyl groups, carbonylamino groups, or O atoms on the ends thereof and optionally containing one or more oxygen atom(s), Z—, $C_{1\text{-}10}$-acyl groups, $C_{1\text{-}10}$-hydroxyacyl substituted imino groups, one to two C—C double bonds and/or one to two C—C triple bonds

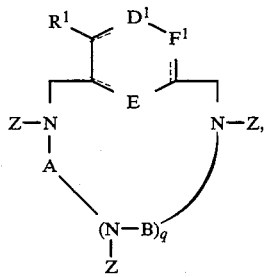

D$^1$ has the same meaning as D, with the exception that D$^1$ does not contain the substituent G, or stands for the radical

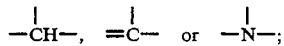

and

F$^1$ has the same meaning as F, with the exception that F$^1$ does not contain the substituent G, or stands for the radical

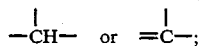

as well as the salts thereof formed with inorganic and-/or organic bases, amino acids or amino acid amides;

with the provisos that at least two of substituents Z are each —CH$_2$COOY, the macrocyclic compound of general formula I contains not more than one radical G, and said compound is not 3,6,9-tris-(carboxymethyl)-3,6,9,15tetraazabicyclo[9.3.1]pentadeca-1(15),11,13-triene or the Cu, Pb, Co and Sr complexes thereof.

2. A compound according to claim 1, wherein Y is H.

3. A compound according to claim 1, wherein at least two of the Y groups are metal ion equivalents of at least one element with atomic numbers 21–29, 42, 44 or, 58–83, or of at least of one radionuclide of an element with atomic numbers 27, 29, 31, 32, 37–39, 43, 49, 62, 64, 70 or 77.

4. A method according to claim 1, wherein G is a macrocycle of general formula II bonded by

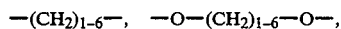
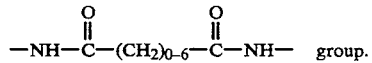

5. A pharmaceutical composition comprising at least one physiologically acceptable compound according to claim 1, and at least one galenical additive.

6. A pharmaceutical composition comprising at least one physiologically acceptable compound according to claim 2, and at least one galenical additive.

7. A pharmaceutical composition comprising at least one physiologically acceptable compound according to claim 3, and at least one galenical additive.

8. A pharmaceutical composition comprising at least one physiologically acceptable compound according to claim 4, and at least one galenical additive.

9. A compound according to claim 1, wherein said compound is a chelate complex of:
3,6,9-tris-(carboxymethyl)-3,6,9,15-tetraazabicyclo-[9.3.1]pentadec-1(15), 11,13-triene, and
at least one element of atomic number 21-29, 42, 44 or 58-70.

10. A compound according to claim 1, wherein D is —CHR$^3$— or =CR$^3$—, F is (—CHR$^1$)$_n$ or (=CR$^1$)$_n$ and q is 1 or 2.

11. A compound according to claim 1, wherein R$^3$ is H, a halogen atom, phenyl, C$_1$-C$_6$-alkyl optionally substituted by one or more phenyl and/or hydroxy group(s), OR$^5$ or

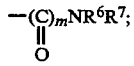

and R$^8$ is H, a halogen atom, or C$_1$-C$_6$-alkyl.

12. A compound according to claim 1, wherein G is a second macrocycle of general formula II which is bonded to a macrocycle of general formula I by

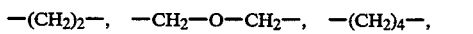
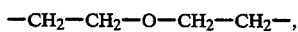
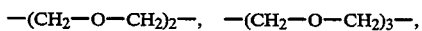
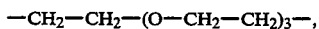
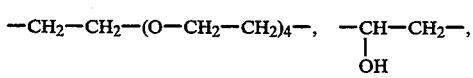
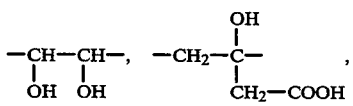
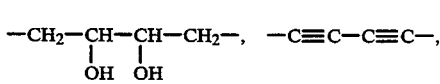
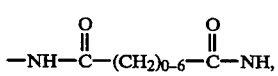
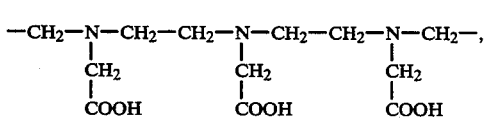
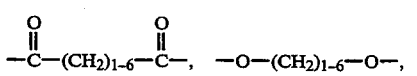
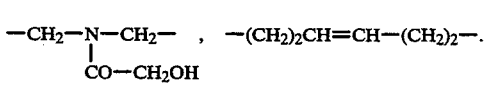

13. A compound according to claim 1, wherein said element is Gd, Dy, Mn, Yb.

14. A compound according to claim 1, wherein said element is Gd.

15. A compound according to claim 1, wherein Z is —CH$_2$COOY.

16. A compound according to claim 1, wherein Q is 1.

17. A compound according to claim 1, wherein A is ethylene and B is ethylene.

18. A compound according to claim 1, wherein A is ethylene, methylethylene or propylene.

19. A compound according to claim 1, wherein B is ethylene, methyethylene or propylene.

20. A compound according to claim 18, wherein B is ethylene, methyethylene or propylene.

21. A compound according to claim 1, wherein D is N, =C=O, =NR$^2$, —CHR$^3$— or =CR$^3$— and q is 1 or 2.

22. A compound according to claim 1, wherein D is O, =C=O, —CHR$^3$— or =CR$^3$— and q is 1 or 2.

23. A macrocyclic compound of formula IV

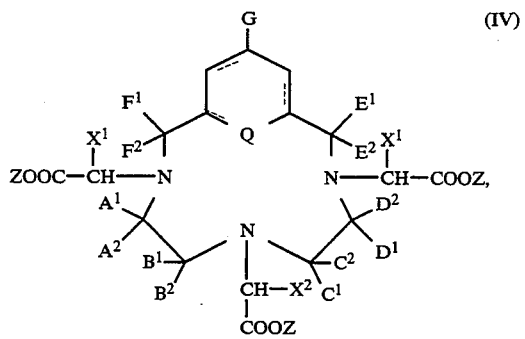

wherein is a single or double bond;
Q is N or NH,
X$^1$ is H, —(CH$_2$)$_n$—R$^1$ or

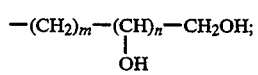

n is 1, 2, 3, 4, or 5;
m is 0, 1 or 2;
R$^1$ is H or OH;
X$^2$ is H, —(CH$_2$)$_n$—R$^1$ or

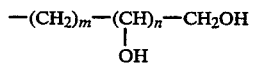

or
—(CH$_2$)$_n$—(O)$_l$—(CH$_2$)$_k$—(C$_6$H$_4$)$_q$—R$^2$;
k is 0, 1, 2, 3 or 4;
l and q are each independently 0 or 1;
R$^2$ is H, C$_1$-C$_4$-alkoxy, a functional group capable of binding to a bio- or macromolecule, or a bio- or macromolecule bound via a functional group;
A$^1$, A$^2$, B$^1$, B$^2$, C$^1$, C$^2$, D$^1$, D$^2$, E$^1$, E$^2$, F$^1$ and F$^2$ are each independently H, —(CH$_2$)$_n$—R$^1$ or

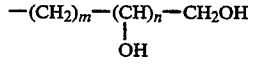

or —(CH$_2$)$_n$—(O)$_l$—(CH$_2$)$_k$—(C$_6$H$_4$)$_q$—R$^2$;

G is H, $C_1$–$C_4$-alkoxy, a functional group capable of binding to a bio- or macromolecule, or a bio- or macromolecule bound via a functional group, or a second macrocycle, bound via K, of general formula V

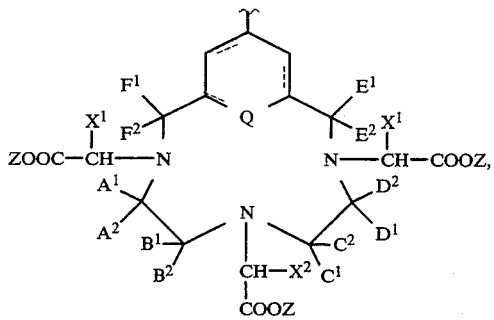

(V)

K is a direct bond, a bis(carbonyl-amino) group or a $C_1$–$C_4$-alkylene group which optionally carries at the ends carbonyl groups, carbonylamino groups or oxygen atoms, and which optionally contains one or several oxygen atom(s), hydroxymethylene, $CH(X^2)COOZ$-substituted imino, acyl-substituted imino and/or hydroxy-acyl-substituted imino groups, and/or one to two C—C-double bond and/or C—C-triple bonds; and Z is in each case H or a metal ion equivalent of an element of atomic number 21–29, 31, 32, 37–39, 42–44, 49 or 57–83;
wherein any or all remaining $CO_2H$ groups can each optionally be present as an ester or amide; or
a physiologically acceptable salt thereof with inorganic and/or organic bases, amino acids or amino acid amides;
with the provisos that:
(a) at least 8 of the 12 ring substituents $A^1$ through $F^2$ stand for a hydrogen atom,
(b) $X^1$ and $X^2$ stand simultaneously for hydrogen only if at least one of the ring substituents $A^1$ through $F^2$ is is not H, and
(c) the macrocycle of general formula I contains no more than one bio- or macromolecule.

24. A macrocyclic compound of claim 23, wherein said compound is of the formula VI

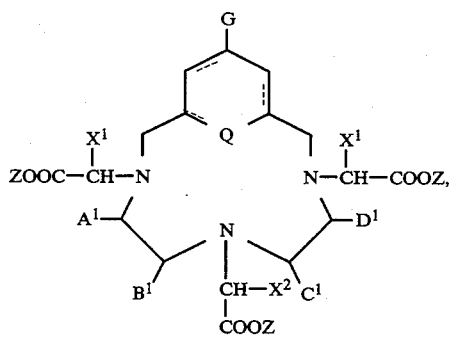

(VI)

wherein
 is a single or double bond;
Q is N or NH,
$X^1$ is H, —$(CH_2)_n$—$R^1$ or

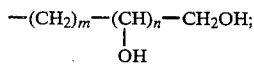

n is 1, 2, 3, 4, or 5;
m is 0, 1 or 2;
$R^1$ is H or OH;
$X^2$ is H, —$(CH_2)_n$—$R^1$ or

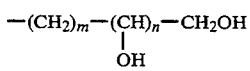

—$(CH_2)_n$—$(O)_l$—$(CH_2)_k$—$(C_6H_4)_q$—$R^2$;
k is 0, 1, 2, 3 or 4;
l and q are each independently 0 or 1;
$R^2$ is H, $C_1$–$C_4$-alkoxy, a functional group capable of binding to a bio- or macromolecule, or a bio- or macromolecule bound via a functional group;
$A^1$, $B^1$, $C^1$ and $D^1$ are each independently H, —$(CH_2)_n$—$R^1$,

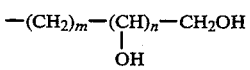

or —$(CH_2)_n$—$(O)_l$—$(CH_2)_k$—$(C_6H_4)_q$—$R^2$;
G is H, $C_1$–$C_4$-alkoxy, a functional group capable of binding to a bio- or macromolecule, or a bio- or macromolecule bound via a functional group, or a second macrocycle, bound via K, of general formula VII

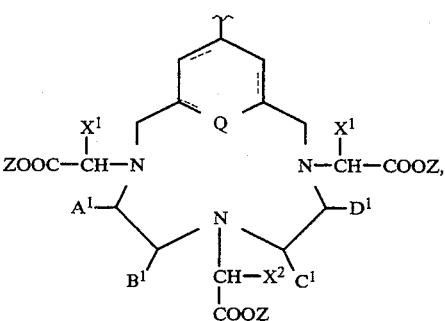

(VII)

K is a direct bond, a bis(carbonyl-amino) group or a $C_1$–$C_4$-alkylene group which optionally carries at the ends carbonyl groups, carbonylamino groups or oxygen atoms, and which optionally contains one or several oxygen atom(s), hydroxymethylene, $CH(X^2)COOZ$-substituted imino, acyl-substituted imino and/or hydroxy-acyl-substituted imino groups, and/or one to two C—C-double bond and/or C—C-triple bonds; and Z is in each case H or a metal ion equivalent of an element of atomic number 21–29, 31, 32, 37–39, 42–44, 49 or 57–83;
wherein any or all remaining $CO_2H$ groups can optionally be present as an ester or amide; or
a physiologically acceptable salt thereof with inorganic and/or organic bases, amino acids or amino acid amides;
with the provisos that:

$X^1$ and $X^2$ stand simultaneously for hydrogen only if at least one of the ring substituents $A^1$ through $D^1$ is is not H.

25. A compound according to claim 24, wherein Z in each case is H.

26. A compound according to claim 23, wherein at least 2 of the groups are metal ion equivalents of at least one element of atomic numbers 21–29, 42, 44 or 58–83, or of at least one radionuclide of an element of atomic numbers 27, 29, 31, 32, 37–39, 43, 49, 62, 64, 70 or 77.

27. A compound according to claim 23, wherein K is

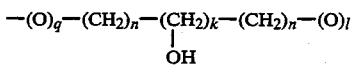

or a direct bond.

28. A compound according to claim 23, wherein $R^2$ is a functional group and said functional group is NCS, $NO_2$, OH, $NHNH_2$, $NH_2$, $NHCOCH_2Br$, $NHCOCH_2Cl$, $CO_2H$, or $CON_3$.

29. A compound according to claim 23, wherein $R^2$ contains a bio- or macromolecule and said bio- or macromolecule is an antibody or antibody fragment.

30. A compound according to claim 23, wherein $R^2$ contains a bio- or macromolecule and said bio- or macromolecule is a protein.

31. A compound according to claim 30, wherein said protein is albumin, globulin or lectin.

32. A compound according to claim 23, wherein $R^2$ contains a bio- or macromolecule and said bio- or macromolecule is a polysaccharide.

33. A compound according to claim 32, wherein said polysaccharide is amylose, dextran or dextrin.

34. A compound according to claim 23, wherein $X^1$ is $CH_2OH$, $CH_2CH_2OH$, or $CHOHCH_2OH$.

35. A compound according to claim 24, wherein $X^2$, $A^1$, $B^1$, $C^1$ and/or $D^1$ each independently are $CH_2OH$, $CH_2CH_2OH$, $CH_2OCH_2C_6H_5$, $CHOHCH_2OH$, $CH_2C_6H_4OCH_3$, $CH_2C_6H_5$, $CH_2H_6H_4O(OCH_2)_3COOH$, or $CH_2C_6H_4NCS$.

36. A pharmaceutical agent comprising at least one compound according to claim 23 and a pharmaceutically acceptable carrier.

37. An agent according to claim 36, further comprising at least one additive customary in galenic pharmacy.

38. A pharmaceutical agent according to claim 36, wherein said at least one compound is in the form of liposomes.

39. A macrocyclic compound according to claim 26, wherein at least two of the Z groups are metal ion equivalents of at least one element of atomic numbers 21–29, 42, 44 or 58–70.

40. A macrocyclic compound according to claim 23, wherein G is H.

41. A macrocyclic compound according to claim 23, wherein three of the Z groups together represent a Gd(III) ion.

42. A macrocyclic compound according to claim 23, wherein said compound is the gadolinium complex of 3,6,9,15-tetraazabicyclo-[9.3.1]pentadeca-1(15),11,13-triene-3,6,9-tris-[α-(2-hydroxyethyl)acetic acid].

43. A macrocyclic compound according to claim 23, wherein G is a second macrocycle, bound via K, of general formula II.

44. A macrocyclic compound according to claim 23, wherein at least three of the Z groups together represent a Gd(III), Eu(III), Dy(III), Ho(III), or Cr(III) ion.

45. A macrocyclic compound according to claim 23, wherein at least two of the Z groups together represent a Fe(II) or Mn(II) ion.

46. A macrocyclic compound according to claim 43, wherein K is a direct bond.

47. A macrocyclic compound according to claim 43, wherein K is a direct bond, a bis(carbonyl-amino) group (—NH—CO—CO—NH—), or a $C_1$-$C_{14}$-alkylene group which optionally carries at the ends carbonyl (—CO—) groups, carbonylamino (—NH—CO—) groups or oxygen atoms, and which optionally contains one or several oxygen atom(s), hydroxymethylene (—CHOH—), $CH(X^2)COOZ$-substituted imino, acyl-substituted imino, and/or hydroxy-acyl-substituted imino groups, and/or one to two C—C-double bonds.

48. A macrocyclic compound according to claim 23, wherein $X^1$ and $X^2$ are each hydroxymethyl.

49. A macrocyclic compound according to claim 23, wherein $X^2$ is benzyloxymethyl.

50. A macrocyclic compound according to claim 23, wherein $X^1$ and $X^2$ are each hydroxyethyl.

51. A macrocyclic compound according to claim 23, wherein $S^1$ and $X^2$ are each dihydroxyethyl.

52. A macrocyclic compound according to claim 23, wherein $X^1$ and $X^2$ are each H and at least one of $A^1$ through $F^2$ is hydroxymethyl.

53. A macrocyclic compound according to claim 23, wherein $X^1$ and $X^2$ are each H and at least one of $A^1$ through $F^2$ is benzyloxymethyl.

54. A macrocyclic compound according to claim 23, wherein $A^1$ through $F^2$ are each H.

55. A macrocyclic compound according to claim 54, wherein three of the Z groups together represent a Gd(III) ion.

56. A macrocyclic compound according to claim 23, wherein $X^1$ is —$(CH_2)_n$—OH and $X^2$ is —$(CH_2)_n$—OH or —$(CH_2)_n$—O—$(CH_2)_x$—$C_6H_4$—$R^2$.

57. A macrocyclic compound according to claim 55, wherein $X^1$ is —$(CH_2)_n$—OH and $X^2$ is —$(CH_2)_n$—OH or —$(CH_2)_n$—O—$(CH_2)_x$—$C_6H_4$—$R^2$.

58. A macrocyclic compound according to claim 23, wherein $R^2$ is H or $C_1$-$C_4$-alkoxy.

59. A macrocyclic compound of Formula I

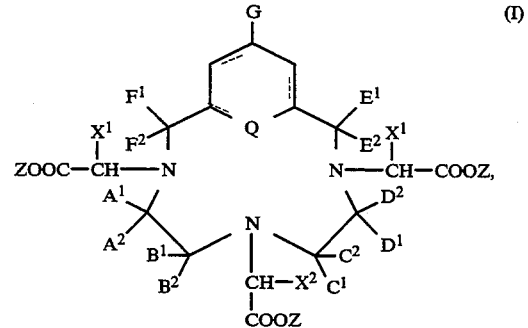

wherein
 is a single or double bond;
Q is a N atom or NH;
$X^1$ is —$(CH_2)_n$—O—$(CH_2)_k$—$C_6H_4$—$R^2$;
$X^2$ is —$(CH_2)_n$—O—$(CH_2)_k$—$C_6H_4$—$R^2$;
n is 1, 2, 3, 4, or 5;
k is 0, 1, 2, 3 or 4;

$R^2$ is H, $C_1-C_4$-alkoxy, a functional group capable of binding to a bio- or macromolecule, or a bio- or macromolecule bound via a functional group;

$A^1$, $A^2$, $B^1$, $B^2$, $C^1$, $C^2$, $D^1$, $D^2$, $E^1$, $E^2$, $F^1$ and $F^2$ are each independently H, $-(CH_2)_n-R^1$,

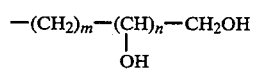

or $-(CH_2)_n-(O)_l-(CH_2)_k-(C_6H_4)_q-R^2$;

m is 0, 1 or 2;

$R^1$ is H or OH;

l and q are each independently 0 or 1;

G is H, $C_1-C_4$-alkoxy, a functional group capable of binding to a bio- or macromolecule, or a bio- or macromolecule bound via a functional group, or a second macrocycle, bound via K, of general formula II

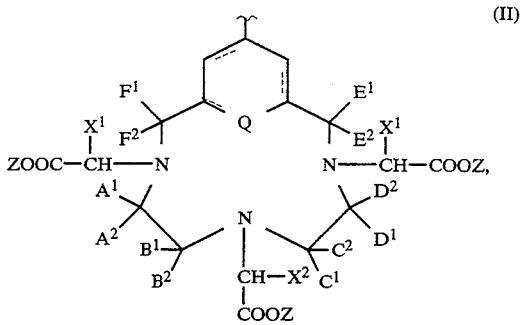

K is a direct bond, a bis(carbonyl-amino) group (—NH—CO—CO—NH—), or a $C_1-C_{14}$-alkylene group which optionally carries at the ends carbonyl (—CO—) groups, carbonylamino (—NH—CO—) groups or oxygen atoms, and which optionally contains one or several oxygen atom(s), hydroxymethylene (—CHOH—), $CH(X^2)COOZ$-substituted imino, acyl-substituted imino, and/or hydroxy-acyl-substituted imino groups, and/or one to two C—C-double and/or C—C-triple bonds; and in each case is H or a metal ion equivalent of an element of atomic number 21-29, 31, 32, 37-39, 42-44, 49 or 57-83;

wherein any or all remaining $CO_2H$ groups can each optionally be present as an ester or amide; and physiologically acceptable salts thereof with inorganic and/or organic bases, amino acids or amino acid amides;

with the provisos that:

(a) at least 8 of the 12 ring substituents $A^1$ through $F^2$ each stand for a hydrogen atom, and (b) the macrocycle of general Formula I contains no more than one bio- or macromolecule.

60. A macrocyclic compound according to claim 59, wherein $X^1$ and $X^2$ are each benzyloxymethyl.

* * * * *

UNITED STATES PATENT AND TRADEMARK OFFICE
CERTIFICATE OF CORRECTION

PATENT NO. : 5,403,572
DATED : April 4, 1995
INVENTOR(S) : Heinz GRIES et al.

It is certified that error appears in the above-indentified patent and that said Letters Patent is hereby corrected as shown below:

Claim 1; column 63, line 15: Insert -- --- -- before "represents".

Claim 1; column 63, line 19: Change "—CHR$_3$—," to read -- —CHR$^3$—, --.

Claim 1; column 63, line 42: Change "C$_4$-" to -- C$_6$- --.

Claim 1; column 63, line 47: Change "C$_4$-" to -- C$_6$- --.

Claim 1; column 63, line 56: Change "C$_4$-" to -- C$_6$- --.

Claim 1; column 63, line 63: Change "C$_4$-" to -- C$_6$- --.

Claim 1; column 64, line 44: Change "15tetraazabicyclo" to read -- 15 tetraazabicyclo --.

Claim 3; column 64, line 51: Change "58" to -- 57 --.

Claim 4; column 64, line 54: Change "method" to -- compound --.

UNITED STATES PATENT AND TRADEMARK OFFICE
CERTIFICATE OF CORRECTION

PATENT NO. : 5,403,572
DATED : April 4, 1995
INVENTOR(S) : Heinz GRIES et al.

It is certified that error appears in the above-indentified patent and that said Letters Patent is hereby corrected as shown below:

Claim 23; column 66, line 37: Insert -- --- -- before "is".

Claim 23; column 67, line 21: Change "$C_1$–$C_4$-" to read -- $C_1$–$C_{14}$- --.

Claim 23; column 66, line 57: Change "1" to -- $\ell$ --.

Claim 23; column 67, line 45: Delete "is" second occurance.

Claim 24; column 67, line 66: Before "is" insert -- --- --.

Claim 24; column 68, line 11: After "—$CH_2OH$", insert -- or --.

UNITED STATES PATENT AND TRADEMARK OFFICE
CERTIFICATE OF CORRECTION

PATENT NO. : 5,403,572
DATED : April 4, 1995
INVENTOR(S) : Heinz GRIES et al.

It is certified that error appears in the above-indentified patent and that said Letters Patent is hereby corrected as shown below:

Claim 24; column 68, line 17: Replace "1" with -- $\ell$ --.

Claim 24; column 68, line 51: Change "$C_4$" to read -- $C_{14}$ --.

Claim 26; column 69, line 7: Insert -- Z -- before "groups".

Claim 26, column 69, line 8: Delete "58" and insert -- 57 --.

Signed and Sealed this

Twenty-sixth Day of September, 1995

Attest:

BRUCE LEHMAN

Attesting Officer    Commissioner of Patents and Trademarks